US012606749B2

(12) United States Patent
Simons et al.

(10) Patent No.: US 12,606,749 B2
(45) Date of Patent: Apr. 21, 2026

(54) BIO-LPG PRODUCTION PROCESS

(71) Applicant: Calor Gas Limited, Warwick (GB)

(72) Inventors: Keith Simons, Warwick (GB);
Hendrick Van Rensburg, Warwick
(GB)

(73) Assignee: Calor Gas Limited, Warwick (GB)

( * ) Notice: Subject to any disclaimer, the term of this
patent is extended or adjusted under 35
U.S.C. 154(b) by 57 days.

(21) Appl. No.: 18/266,186

(22) PCT Filed: Dec. 9, 2021

(86) PCT No.: PCT/EP2021/085074
§ 371 (c)(1),
(2) Date: Jun. 8, 2023

(87) PCT Pub. No.: WO2022/122969
PCT Pub. Date: Jun. 16, 2022

(65) Prior Publication Data
US 2024/0043754 A1 Feb. 8, 2024

(30) Foreign Application Priority Data
Dec. 9, 2020 (GB) ...................................... 2019432

(51) Int. Cl.
*C10G 3/00* (2006.01)
*B01J 29/40* (2006.01)
(Continued)

(52) U.S. Cl.
CPC ............... *C10G 3/49* (2013.01); *B01J 29/40*
(2013.01); *B01J 29/7038* (2013.01);
(Continued)

(58) Field of Classification Search
CPC .... C10G 3/49; C10G 3/62; C10G 2300/4006;
B01J 29/40; B01J 29/7038; B01J 35/615;
(Continued)

(56) References Cited

U.S. PATENT DOCUMENTS

| | | | |
|---|---|---|---|
| 4,621,164 A | 11/1986 | Chang et al. | |
| 5,965,754 A | 10/1999 | Clark et al. | |
| (Continued) | | | |

FOREIGN PATENT DOCUMENTS

| | | |
|---|---|---|
| CN | 1557554 A | 12/2004 |
| CN | 102992931 A | 3/2013 |
| (Continued) | | |

OTHER PUBLICATIONS

Sousa et al. ("Bioethanol conversion into hydrocarbons on HZSM-5
and HMCM-22 zeolites: Use of in situ DRIFTS to elucidate the role
of the acidity and of the pore structure over the coke formation and
product distribution", Catalysis Today 234 (2014) 182-191). (Year:
2014).*
(Continued)

*Primary Examiner* — Ali Z Fadhel
(74) *Attorney, Agent, or Firm* — Ryan T. Grace; Advent,
LLP

(57) ABSTRACT

The present invention is in the field of processes for the
production of BioLPG, and catalysts for use in said pro-
cesses.

22 Claims, 34 Drawing Sheets

(51) Int. Cl.

| | |
|---|---|
| *B01J 29/70* | (2006.01) |
| *B01J 35/61* | (2024.01) |
| *B01J 35/63* | (2024.01) |
| *B01J 35/64* | (2024.01) |
| *B01J 37/02* | (2006.01) |
| *B01J 37/28* | (2006.01) |
| *B01J 38/12* | (2006.01) |
| *C07C 1/20* | (2006.01) |
| *C07C 1/24* | (2006.01) |

(52) U.S. Cl.
CPC ........... *B01J 35/615* (2024.01); *B01J 35/633* (2024.01); *B01J 35/647* (2024.01); *B01J 37/0201* (2013.01); *B01J 37/024* (2013.01); *B01J 37/28* (2013.01); *B01J 38/12* (2013.01); *C07C 1/24* (2013.01); *C10G 3/62* (2013.01); *B01J 2229/12* (2013.01); *B01J 2229/186* (2013.01); *C07C 1/20* (2013.01); *C07C 2529/40* (2013.01); *C10G 2300/4006* (2013.01)

(58) Field of Classification Search
CPC .... B01J 35/633; B01J 35/647; B01J 37/0201; B01J 37/024; B01J 37/28; B01J 38/12; B01J 2229/12; B01J 2229/186; B01J 29/7015; B01J 29/041; B01J 29/80; C07C 1/24; C07C 1/20; C07C 2529/40; C07C 2529/04; C07C 2529/70; C07C 1/22; C07C 2529/06; C07C 2529/80; C10L 3/12; C10L 2200/0415; C10L 2200/0469; C10L 2290/12; Y02E 50/10; Y02P 30/20
See application file for complete search history.

(56) References Cited

U.S. PATENT DOCUMENTS

| | | |
|---|---|---|
| 2010/0174127 A1 | 7/2010 | Chang |
| 2011/0137096 A1* | 6/2011 | Minoux .................... C07C 1/20<br>585/324 |
| 2013/0217943 A1* | 8/2013 | Minoux .................... C07C 1/24<br>585/639 |
| 2014/0081063 A1* | 3/2014 | Viswanadham ......... B01J 35/45<br>585/408 |
| 2014/0171691 A1 | 6/2014 | Kortan et al. |

FOREIGN PATENT DOCUMENTS

| | | |
|---|---|---|
| EP | 2060550 A1 | 5/2009 |
| EP | 3495455 A1 | 6/2019 |
| WO | 2008109877 A1 | 9/2008 |
| WO | 2009091336 A1 | 7/2009 |
| WO | 2019084518 A1 | 5/2019 |

OTHER PUBLICATIONS

Inoue, K. et al., "Metal modification effects on ethanol conversion to propylene by H-ZSM-5 with Si/Al2 ratio of 150," National Institute of Advanced Industrial Science and Technology (AIST), Reaction Kinetics, Mechanisms and Catalysis, vol. 101(2), Published Sep. 2010, pp. 477-489, ISSN: 1878-5190.

International Search Report for Application No. PCT/EP2021/085074, dated Jul. 8, 2022.

Losch, et al., "Phosphorous Modified ZSM-5 Zeolites: Impact on Methanol Conversion into Olefins," Topics in Catalysis, vol. 58, No. 14, Aug. 2015, pp. 826-832, XP035553453, ISSN: 1022-5528.

Machado, N. et al., "Hydrocarbons from ethanol using [Fe, Al]ZSM-5 zeolites obtained by direct synthesis," Applied Catalysis A: General, vol. 311, Sep. 2006, pp. 193-198, ISSN: 0926-860X.

Proscanu, R. et al., "Metal impregnated catalysts for bioethanol conversion tested by n-hexane cracking," Ovidius University Annals of Chemistry, vol. 23, No. 2, Dec. 2012, pp. 137-142, 10.2478/v10310-012-0023-4.

Sadeghpour, P., "High-temperature efficient isomorphous substitution of boron into ZSM-5 nanostructure for selective and stable production of ethylene and propylene from methanol," Materials Chemistry and Physics, vol. 217, Sep. 2018, pp. 133-150, XP055814235, ISSN: 0254-0584.

Search Report for Application No. GB2019432.0, dated May 17, 2021.

Search Report for Application No. GB2019432.0, dated Nov. 5, 2021.

Sousa, Z. et al., "Bioethanol conversion into hydrocarbons on HZSM-5 and HMCM-22 zeolites: Use of in situ Drifts to elucidate the role of the acidity and of the pore structure over the coke formation and product distribution," Catalysis Today, vol. 234, Oct. 2014, pp. 182-191, ISSN: 0920-5861.

Examination Report from European Application No. 21834794.6, dated Apr. 1, 2025.

\* cited by examiner

Table of BET results

| | | Surface Area (m²/g) | Pore Volume (cm³/g) | Pore Size (Å) |
|---|---|---|---|---|
| ZSM5-30 | | 393 | 0.239 | 24 |
| DRS151/1 | B1/ZSM5-30 | 328 | 0.209 | 25 |
| DRS151/2 | B3/ZSM5-30 | 271 | 0.174 | 26 |
| DRS151/11 | P1/ZSM5-30 | 303 | 0.191 | 24 |
| DRS151/12 | P3/ZSM5-30 | 284 | 0.184 | 25 |
| DRS151/19 | P2/ZSM5-30 | 288 | 0.188 | 26 |
| DRS151/21 | Ga1/ZSM5-30 | 347 | 0.215 | 25 |
| DRS151/22 | Ga3/ZSM5-30 | 316 | 0.204 | 26 |
| DRS151/25 | Mg1/ZSM5-30 | 322 | 0.209 | 26 |
| DRS151/26 | Zn1/ZSM5-30 | 350 | 0.220 | 25 |
| DRS151/27 | K1/ZSM5-30 | 307 | 0.189 | 25 |
| DRS151/28 | K3/ZSM5-30 | 336 | 0.199 | 24 |
| ZSM5-80 | | 437 | 0.257 | 23 |
| DRS151/3 | B1/ZSM5-80 | 334 | 0.201 | 24 |
| DRS151/4 | B3/ZSM5-80 | 274 | 0.174 | 25 |
| DRS151/13 | P1/ZSM5-80 | 311 | 0.187 | 24 |
| DRS151/14 | P3/ZSM5-80 | 332 | 0.206 | 25 |
| DRS151/20 | P2/ZSM5-80 | 323 | 0.198 | 25 |
| DRS151/23 | Ga1/ZSM5-80 | 368 | 0.227 | |
| DRS151/24 | Ga3/ZSM5-80 | 323 | 0.197 | |
| ZSM5-200 | | 613 | 0.353 | 23 |
| DRS151/10 | B1/ZSM5-200 | 319 | 0.192 | 25 |
| DRS151/18 | P1/ZSM5-200 | 334 | 0.197 | 24 |

Figure 47

Table of BET results

| | | Surface Area (m²/g) | Pore Volume (cm³/g) | Pore Size (Å) |
|---|---|---|---|---|
| SAPO 11 | | 178 | 0.145 | 33 |
| DRS151/9 | B1/SAPO11 | 20 | 0.074 | 147 |
| DRS151/17 | P1/SAPO11 | 93 | 0.076 | 33 |
| SAPO 34 | | 537 | 0.248 | 19 |
| DRS151/5 | B1/SAPO34 | 378 | 0.177 | 19 |
| DRS151/6 | B3/SAPO34 | 1 | 0.003 | 75 |
| DRS151/15 | P1/SAPO34 | 454 | 0.214 | 19 |
| DRS151/16 | P3/ SAPO34 | 106 | 0.054 | 21 |
| MCM22 | | 484 | 0.568 | 47 |
| DRS151/7 | B1/MCM22 | 378 | 0.523 | 59 |
| DRS151/8 | B3/MCM22 | 1 | 0.405 | 66 |
| DRS151/29 | Ni1/MCM22 | 465 | 0.652 | 56 |
| DRS151/30 | Ni3/MCM22 | 461 | 0.571 | 50 |

Figure 48

Isotherm Linear Plot HZSM5-30 Materials

Isotherm Linear Plot HZSM5-80 Materials

Reaction Temperature

Ar flow rates

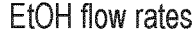
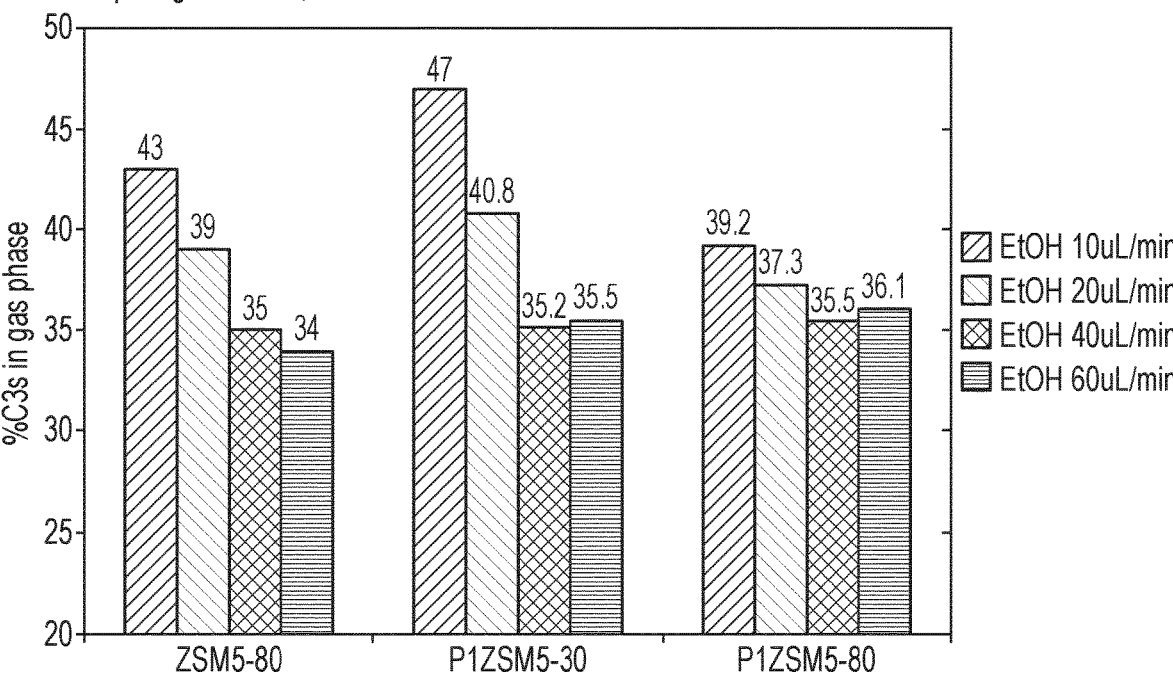
Figure 59
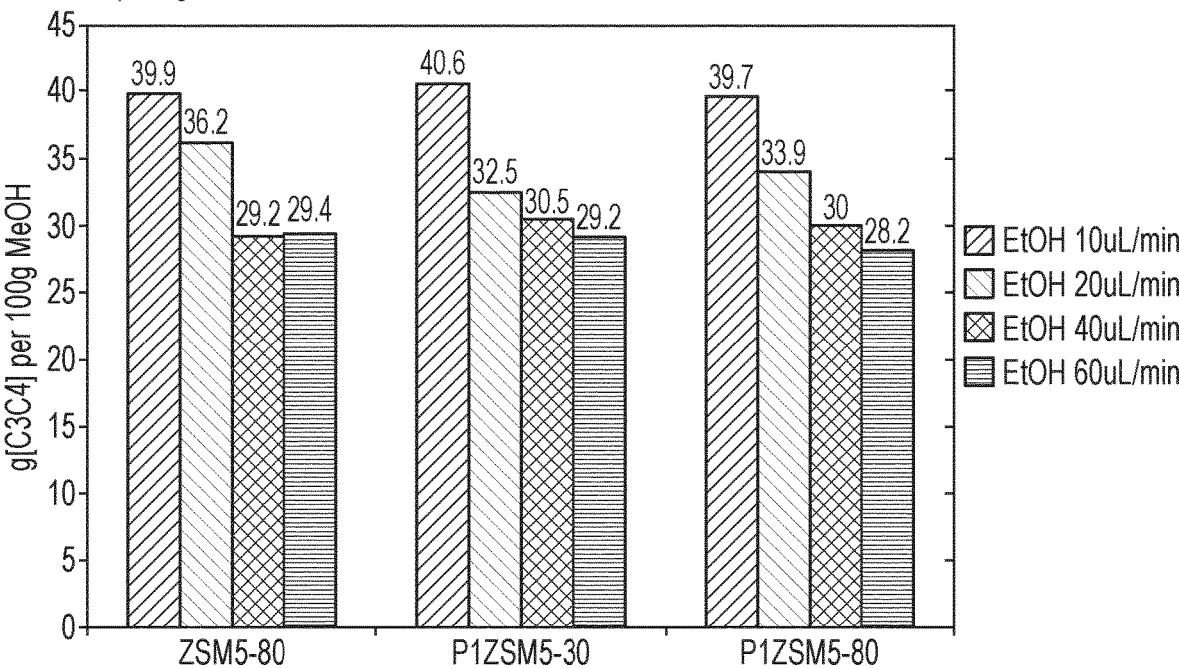
Figure 60

Reaction Pressure

BIO-LPG PRODUCTION PROCESS

FIELD OF THE INVENTION

The present invention is in the field of processes for the production of BioLPG, and catalysts for use in said processes.

BACKGROUND OF THE INVENTION

Liquefied petroleum gas (LPG) typically comprises propane, butane, or a mixture of the two. LPG may also contain other hydrocarbons in small quantities such as propylene and butylene. At the end of 2018, LPG was estimated to be consumed in an amount of around 300 million tonnes per year. LPG is used in a variety of applications such as fuel for heating appliances, cooking equipment such as outdoor stoves and gas barbeques and certain vehicles.

Historically, LPG has been derived from fossil fuel sources. For example, LPG can be extracted or manufactured during the refining of petroleum or wet natural gas, or extracted from petroleum and natural gas streams as they emerge from the ground. Since conventionally manufactured LPG is a fossil fuel, in order to reduce net carbon emissions, there has recently been increased interest in replacing LPG derived from fossil fuel sources with LPG derived from biological sources (BioLPG). BioLPG (also known as renewable LPG, renewable propane, renewable butane, biopropane or biobutane) has a much lower carbon footprint than conventionally derived LPG. There is thus great interest from the LPG industry and decarbonisation-proponents to expand production volumes of BioLPG.

The following seven general classes of process have been suggested for BioLPG production: i) hydrotreating of bio-oils such as waste vegetable oils; (ii) dehydrogenation of bio-oils and glycerine; iii) fermentation of sugars; iv) hydrolysis and fermentation of cellulosic biomass; v) digestion such as anaerobic digestion by bacteria of wet organic wastes; vi) gaseous conversion and synthesis of cellulosic biomass or organic waste; and vii) liquid conversion and synthesis of cellulosic biomass and organic waste. Many of these processes manufacture BioLPG in low yield as a by-product only, and are principally directed to the manufacture of different products.

Additionally, many of these suggested processes have only been successfully demonstrated in the laboratory or remain at the concept stage, and have not been successfully commercialised. Of the processes discussed above, only hydrotreating of bio-oils has been successfully commercialised. Hydrotreatment is thus the only significant source of BioLPG production. Hydrotreating of bio-oils produces BioLPG as a by-product, and is principally directed to the production of HVO (hydrogenated vegetable oil) biodiesel. In such hydrotreatment processes, the ratio of biodiesel to biopropane produced is typically around 9:1 to 10:1. Some of these hydrotreatment processes involve the hydrotreatment of a purely bio-oil feedstock. However, many processes involve mixing bio-oil with petroleum intermediates to form a blend and hydrotreating the blend to form a mixture of diesel and biodiesel, and a small amount of BioLPG by-product. An in-depth discussion of the various processes known for or suggested for BioLPG production is provided in Process Technologies and Projects for BioLPG, Eric Johnson, Energies, 2019, 12, 250.

There is thus a need for new commercially viable routes for the production of BioLPG. In particular, there is a need for BioLPG production processes that produce BioLPG in high yield.

It is known to use ethanol as a feedstock in various processes for the production of longer chain hydrocarbons such as gasoline and olefins, in which small amounts of LPG are produced as a by-product.

US20140081063 discloses a process for the preparation of high-octane gasoline from bioethanol using a ZSM-5 catalyst. LPG is produced as a by-product of this process in low yields of less than 25%.

Johansson et al., The Hydrocarbon Pool in Ethanol-to-Gasoline over ZSM-5 catalysts, Catalysis Letters, (2009), 127:1-6 discloses a process in which ethanol is converted to gasoline with a ZSM5 catalyst.

Costa et al., Synthesis of Propylene from Ethanol using Phosphorus-modified HZSM-5, Brazilian Journal of Chemical Engineering, Vol. 33, No. 3, pages 503-513 discloses a process for converting ethanol to propylene using a phosphorus-promoted HZSM-5 catalyst. Propane is produced as a minor by-product of the process in yields of less than 10%.

The processes described above are not principally concerned with the production of LPG, but to the production of longer chain hydrocarbons or olefins. LPG is only formed in the processes as a secondary by-product in low yield. The process parameters and catalysts used in these processes are specifically adapted and tailored for the production of olefins and longer chain alkanes.

Thus there is a need for a process in which ethanol can be converted to LPG in high yield, thereby providing a high yield, economically viable LPG production process.

SUMMARY OF THE INVENTION

The present invention is based upon the surprising finding that certain aliphatic alcohols can be used as a feedstock in processes for the production of BioLPG in high yield. Using certain process conditions and certain specific zeolite catalysts, aliphatic alcohols such as ethanol or isopropyl alcohol derived from renewable biological sources can be converted to BioLPG in high yield. It has been surprisingly found that catalysts comprising a ZSM5 zeolite material or an MCM22 zeolite material can convert certain aliphatic alcohols to mixtures of biopropane and biobutane (i.e. BioLPG) in high yield under certain reaction conditions. The high yields associated with the present process have not been found to be associated with the use of different zeolite catalyst materials. The particular zeolite materials have also been found to have a longer catalyst lifetime in comparison to other zeolite catalysts when used in the process. An additional advantage of the use of ZSM5 and MCM22 zeolite materials as catalysts is that it has been found that the catalytic activity of these catalysts in the process can be rejuvenated simply after use by exposure to air. Typically, the selectivity and catalytic activity of zeolite catalysts diminishes with the use of the catalyst in a particular process. Whilst it may be possible to rejuvenate the activity of the catalyst to some extent by various methods, it is often not possible to fully rejuvenate the selectivity and activity of a catalyst, meaning that the effectiveness of the catalyst may gradually diminish over time. Surprisingly, it has been found that once diminished through use, the selectivity and catalytic activity of the ZSM5 and MCM22 catalyst materials in the process of the invention can be rejuvenated by exposure to air such that the catalytic activity and selectivity of the catalysts is rejuvenated to a great extent, and in some instances, to the original activity and selectivity of the catalyst in the process. It has additionally been found possible to optimise and tailor the ZSM5 and MCM22 zeolite materials so as to provide novel ZSM5 and MCM22 zeolite catalysts that can be used to provide even higher yields and selectivities for BioLPG in the process, and to have even higher catalyst lifetimes.

According to a first aspect of the invention, there is provided a process for the selective production of BioLPG from C2 or C3 aliphatic alcohols, wherein the process comprises:

(a) introducing a feedstream comprising one or more C2 or C3 aliphatic alcohols into a reaction vessel comprising a catalyst, wherein the catalyst comprises a ZSM5 zeolite material, an MCM22 zeolite material, or a combination thereof;

(b) contacting the feedstream and catalyst within the reaction vessel at a temperature of from 250° C. to 750° C. and a pressure of from 0.5 atm to 50 atm; and (c) recovering a product stream comprising C3 and/or C4 aliphatic hydrocarbons from the reaction vessel.

Typically, the contacting is carried out at a temperature of from 350° C. to 600° C., and preferably from 375° C. to 500° C.

Typically, the contacting is carried out at a pressure of from 1 atm to 20 atm, preferably from 1 atm to 15 atm, and more preferably from 1 atm to 10 atm.

Alternatively, the contacting is carried out at a pressure of from 3 atm to 50 atm, preferably from 3 atm to 20 atm, more preferably from 3 atm to 15 atm, and most preferably from 3 atm to 10 atm.

Preferably, the contacting is carried out at a temperature of from 350° C. to 600° C. and a pressure of from 3 atm to 10 atm. Most preferably, the contacting is carried out a temperature of from 375° C. to 500° C. and a pressure of from 3 atm to 10 atm.

The process may be carried out as a continuous process. Alternatively, the process may be carried out as a batch process. In preferable embodiments, process steps a) to c) are carried out as a continuous flow process. Preferably, the continuous flow process comprises introducing the feedstream to the reactor vessel at a flow rate of from 1 μL to 10 μL per minute per 150 mg of catalyst present in the reactor vessel; preferably, at a flow rate of from 1 μL to 7.5 μL per minute per 150 mg of catalyst present in the reactor vessel; more preferably, at a flow rate of from 1 μL to 5 μL per minute per 150 mg of catalyst present in the reactor vessel. Most preferably, the continuous flow process comprises introducing the feedstream to the reactor vessel at a flow rate of from 1 μL to 3 μL per minute per 150 mg of catalyst present in the reactor vessel. In some instances, the continuous flow process comprises introducing the feedstream to the reactor vessel at a flow rate of from 1.5 μL to 2.5 μL per minute per 150 mg of catalyst present in the reactor vessel, such as at a flow rate of from 1.75 μL to 2.25 μL per minute per 150 mg of catalyst present in the reactor vessel.

The process may further comprise passing an inert gas through the reaction vessel. Typically, the inert gas is argon. The inert gas is typically introduced into the reaction vessel at a flow rate of from 0.5 ml/min to 10 ml/min per 150 mg of catalyst, preferably from 0.5 ml/min to 5 ml/min per 150 mg of catalyst, more preferably 1.5 ml/min to 5 ml/min per 150 mg of catalyst, and most preferably from 2 ml/min to 5 ml/min per 150 mg of catalyst. In some instances, the inert gas is introduced into the reaction vessel at a flow rate of from 0.5 ml/min to 1.5 ml/min per 150 mg of catalyst, and more preferably from 0.75 ml/min to 1.25 ml/min per 150 mg of catalyst. Preferably, process steps a) to c) are carried out continuously as a continuous flow process and contacting step b) further comprises passing an inert gas through the reaction vessel during contacting step b). Preferably, the inert gas is argon, although other inert gases such as nitrogen may be used.

Preferably, the contacting is carried out at a pressure of from 1 atm to 20 atm; wherein the continuous flow process comprises introducing the feedstream to the reactor vessel at a flow rate of from 1 μL to 3 μL per minute per 150 mg of catalyst present in the reactor vessel; and wherein the process further comprises passing an inert gas such as argon through the reaction vessel during contacting step b), wherein the inert gas is introduced into the reaction vessel at a flow rate of from 0.5 ml/min to 5 ml/min per 150 mg of catalyst.

The process may further comprise contacting the catalyst with an inert diluent gas. Preferably, the inert diluent gas comprises nitrogen. Preferably, process steps a) to c) are carried out continuously as a continuous flow process and contacting step b) further comprises contacting the catalyst with an inert diluent gas such as nitrogen.

Prior to step a), the zeolite material present in the catalyst is preferably present in the H-form. The H-form of a zeolite catalyst is the form in which the zeolite comprises hydrogen cations. Accordingly, prior to step a), if the catalyst is not present in the H-form, the catalyst is treated so as to be present in the form. Accordingly, in some embodiments, the catalyst is contacted with air or oxygen under conditions suitable to provide the catalyst in the H-form. Accordingly, in preferable embodiments, prior to step a), the catalyst is contacted with air or oxygen at a temperature of from 400° C. to 650° C., and preferably from 500° C. to 600° C. More preferably, prior to step a), the catalyst is contacted with air or oxygen at a temperature of from 400° C. to 650° C. for a time period of from 1 hour to 10 hours. Most preferably, prior to step a), the catalyst is contacted with air or oxygen at a temperature of from 4 hours to 6 hours.

In the embodiments described in the paragraph directly above, in some embodiments, prior to step a), but after the catalyst has been contacted with air or oxygen at a temperature of from 400° C. to 650° C. for a time period of from 1 hour to 10 hours, the reaction vessel is heated to a temperature of from 400° C. to 500° C. under air or oxygen flow, preferably, for a time period of from 5 hours to 10 hours, before purging with an inert gas such as argon. Such a step is typically carried out to ensure that the zeolite catalysts are in the H-form.

Preferably, the one or more C2 or C3 aliphatic alcohols comprise ethanol, isopropyl alcohol, or a combination thereof.

In some embodiments one or more C2 or C3 aliphatic alcohols comprise ethanol as the sole C2 or C3 aliphatic alcohol present in the feedstream.

In other embodiments, the one or more C2 or C3 aliphatic alcohols comprise a mixture of ethanol and isopropyl alcohol. For example, in some embodiments, the one or more C2 or C3 aliphatic alcohols comprise ethanol in an amount of from 30% to 70% by weight of the feedstream, and isopropyl alcohol in an amount of from 30% to 70% by weight of the feedstream. In preferable instances, ethanol is present in an amount of from 40% to 60% by weight and isopropyl alcohol is present in an amount of from 40% to 60% by weight of the feedstream. For example, the ethanol and isopropyl alcohol can both be present in the feedstream in an amount of about 50% by weight of the feedstream.

Preferably, the one or more C2 or C3 aliphatic alcohols are derived from renewable biological resources. Thus, in some embodiments, the feedstream does not comprise C2 or C3 aliphatic alcohols derived from fossil fuels. In some embodiments, the feedstream does not comprise any organic compounds derived from fossil fuels.

In preferable embodiments, the one or more C2 or C3 aliphatic alcohols are derived from fermentation or bio-generation.

In some embodiments, the one or more C2 or C3 aliphatic alcohols are produced from fermentation of biological organic material, such as fermentation of cellulosic material. Processes for the fermentation of cellulosic material so as to provide biologically derived C2 or C3 aliphatic alcohols are known in the art.

In other embodiments, the one or more C2 or C3 aliphatic alcohols are derived from recycled carbon. For example, the one or more C2 or C3 aliphatic alcohols may be produced from fermentation of flue gases or bio-generated syngas. Flue gases are the waste product stream of many industrial processes. Flue gases and syngas comprise hydrogen, carbon monoxide and carbon dioxide. These gases can be converted by microorganisms in fermentation processes into C2 or C3 aliphatic alcohols.

The term BioLPG as used herein is to be understood in accordance with the normal meaning of the term in the art. BioLPG is LPG produced from a feedstock that is derived from a biological source instead of fossil fuels. The term derived from a biological source as used herein is used to refer to material that is directly obtained from a biological source or indirectly obtained from a biological source. For example, the term derived from a biological source as used herein encompasses materials obtained by a chemical process where the starting material of the chemical process is obtained from a biological source. For example, where a material obtained from a biological source is chemically processed into a chemical intermediate prior to conversion of the intermediate into LPG, the LPG is still considered to be BioLPG. The term BioLPG as used herein is also used to refer to LPG produced from a feedstock that has been produced by a microbial process such as fermentation. The feedstock for the microbial process such as fermentation may itself have been derived from fossil fuels, for example carbon dioxide or carbon monoxide obtained from the combustion of fossil fuels. LPG produced by such a process is considered to be BioLPG since the feedstock of the LPG production process is a product of a biological process that has a feedstock that is a gas obtained from the combustion of fossil fuels, that would otherwise be released into the atmosphere and contribute to atmospheric carbon levels.

Preferably, the feedstream comprising one or more C2 or C3 aliphatic alcohols comprises the one or more C2 or C3 aliphatic alcohols in an amount of from 70% by weight to 100% by weight, preferably from 80% to 100% by weight of the total weight of components of the feedstream.

In some embodiments, the feedstream comprising one or more C2 or C3 aliphatic alcohols further comprises water. Typically, the water is present in the feedstream in an amount of from 1% by weight to 30% by weight of the total weight of components of the feedstream. Preferably, the water is present in the feedstream in an amount of from 10% by weight to 20% by weight of the total weight of components of the feedstream. In these embodiments, the feedstream typically comprises ethanol in an amount of from 70% by weight to 99% by weight, and preferably from 80% by weight to 90% by weight of the total weight of components of the feedstream.

Surprisingly, it has been found that low levels of water (such as the amounts discussed above) in the process feedstream prolong the lifetime of the zeolite material catalysts. Where the feedstream comprises water, it has been found that the catalyst selectivity and activity for the production of BioLPG remains at a sufficiently high level without deactivation for an increased amount of time compared to where the feedstream does not comprise any water. This is surprising since it is well documented that water vapour at high temperatures often results in dealumination of zeolite catalysts leading to their concomitant deactivation. The extension of catalyst lifetime is particularly advantageous since biologically derived C2 or C3 aliphatic alcohols often comprise water left over from their production processes such as fermentation. Separation of water from biologically derived C2 or C3 aliphatic alcohols so as to provide the anhydrous alcohols is expensive and desirable to avoid if possible. Accordingly, the process of the invention is advantageous in not only does the presence of water in the feedstream not impede the activity of the catalyst, the presence of water in the feedstream actually enhances the lifetime of the catalyst. Where the process is a continuous process, the process can thus be performed continuously for longer periods of time without it being necessary to stop the process intermittently to rejuvenate the catalyst.

The process of the invention has a high selectivity for the production of C3 and/or C4 hydrocarbons over the production of C2 hydrocarbons or longer chain hydrocarbons. BioLPG comprises predominantly C3 and/or C4 hydrocarbons, such as saturated C3 and/or C4 hydrocarbons such as propane and butane.

In some embodiments, at least 90% of the one or more C2 or C3 aliphatic alcohols are converted into hydrocarbon products. In some embodiments, at least 95% of the one or more C2 or C3 aliphatic alcohols are converted into hydrocarbon products, and most preferably about 100% of the one or more C2 or C3 aliphatic alcohols are converted into hydrocarbon products.

In some embodiments, the process of the invention produces C3 and/or C4 hydrocarbons in a yield of at least 20%, at least 30%, at least 40%, at least 50%, or at least 60%. Preferably, the process produces C3 and/or C4 hydrocarbons in a yield of at least 30%.

The exact yield of C3 and/or C4 hydrocarbons will depend upon the nature of the specific process conditions used for a process, and the particular catalyst used in the process.

In some embodiments, the catalyst comprises a ZSM5 zeolite material and the process of the invention produces C3 and/or C4 hydrocarbons in a yield of from 55% to 60%. Preferably, at least 95% of the one or more C2 or C3 aliphatic alcohols are converted into hydrocarbon products, and most preferably about 100% of the one or more C2 or C3 aliphatic alcohols are converted into hydrocarbon products.

In other embodiments, the catalyst comprises an MCM22 zeolite material and the process of the invention produces C3 and/or C4 hydrocarbons in a yield of from 45% to 55%. Preferably, at least 95% of the one or more C2 or C3 aliphatic alcohols are converted into hydrocarbon products, and most preferably about 100% of the one or more C2 or C3 aliphatic alcohols are converted into hydrocarbon products.

In some embodiments, the process has a selectivity for C3 and C4 aliphatic hydrocarbons after two days of at least 30%, when the flow rate of the feedstream is from 1.75 μL to 2.25 μL per minute per 150 mg of catalyst present in the reactor vessel.

The reaction vessel can comprise the catalyst in any suitable configuration or set-up for effectively carrying out the process of the invention. For example, the reaction vessel may comprise a fixed bed reactor. Alternatively, the reaction vessel may comprise a fluidised bed reactor.

Other suitable features of the reaction vessel and means for implementing the process of the invention are those typically used in the art for a catalytic process such as the process of the invention.

In some embodiments, the catalyst comprising the zeolite material may comprise a carrier or support material. However, this is not essential and in some embodiments, the catalyst may be unsupported. Examples of suitable carrier or support materials are those commonly known in the art such as carbon, silica, alumina, or combinations thereof.

In some embodiments, the catalyst comprising the zeolite material may further comprise one or more binder materials. Examples of suitable binder materials include clay or alumina. In some embodiments, the catalyst material comprising the zeolite and the one or more binder materials may be pelleted or extruded. In other embodiments, the catalyst may be free of binder, carrier or support material.

The catalysts comprising zeolite materials for use in the process of the invention may be present as particles of any suitable size for carrying out the process of the invention.

The catalyst comprises a ZSM5 catalyst material, an MCM22 catalyst material, or a combination thereof. As discussed above, the catalysts are preferably present in the H-form of the catalyst. The term H-form of a zeolite as used herein is used in its normal manner in the art to refer to zeolite catalysts in their protonated form.

ZSM5 and MCM22 are zeolite materials known in the art. The terms ZSM5 and MCM22 refer to generic classes of zeolite materials that are defined by a particular structure. Within each class of zeolite materials as used herein (i.e. ZSM5 or MCM22), the silica to alumina ratio (Si/Al ratio) may vary.

Where the catalyst comprises a ZSM5 zeolite material, the ZSM5 zeolite material preferably has a Si/Al ratio of from 20 to 150, more preferably from 25 to 100, and most preferably from 25 to 90. In highly preferable embodiments of the invention where the catalyst comprises a ZSM5 zeolite material, the Si/Al ratio is 30 or 80.

Where the catalyst comprises an MCM22 zeolite material, the catalyst typically comprises MCM22 with a Si/Al ratio of from 10 to 70.

It has been found that zeolite materials with the Si/Al ratios discussed are better at providing BioLPG in higher yields than zeolite materials with Si/Al ratios outside of these ranges. It is known that the acidity of a zeolite material may be affected, inter alia, by the Si/Al ratio of the zeolite material. Typically, a higher Si/Al ratio means that the zeolite material has a lower acidity. Without being limited by any particular theory, it is believed that ZSM5 and MCM22 zeolite materials with the Si/Al ratios discussed above have a level of acidity that is optimum for increasing the yield of the one or more C3 and/or C4 hydrocarbons in the product stream.

Zeolite materials may be promoted by the addition of additional elements to the zeolite structures. Zeolites are typically represented by the formula $M_{2/n}O \cdot Al_2O_3 \cdot xSiO_2 \cdot yH_2O$. In said structures, M is a cation; n is the valence of the cation; x is the Si:Al ratio; and y is the number of water molecules present in the structure. The alumina and silica ($Al_2O_3$ and $SiO_2$) units are typically present in a porous framework of the zeolite structure, with the cations and water molecules present in the pores. A promoted zeolite material is one where small quantities of an additional element (other than Aluminium, Oxygen or Silicon) have been chemically introduced into the zeolite structure. A promoted zeolite material may have different properties in relation to the unpromoted zeolite material. For example, the catalytic activity in a given reaction, selectivity for certain products, acidity, and many other chemical properties of the zeolite may be tailored by the introduction of promoter elements to the zeolite structure. Often the effect of introducing a promoter element may have an unpredictable effect upon one or more properties of the zeolite material such as its effect upon the catalytic activity of said zeolite material in a given reaction. Additionally, often the effect of adding different amounts of the same promoter element to a zeolite material may have different effects upon the properties of the zeolite material.

Surprisingly, it has been found by the inventors of the present invention that when the ZSM5 and MCM22 zeolite materials for use in the process of the present invention are promoted so as to reduce the acidity of the zeolite material, the catalytic activity of the zeolite material in the process of the invention is improved. In particular, the selectivity of the process for C3 and/or C4 hydrocarbons may be improved and/or the lifetime of the catalyst before said catalyst is deactivated due to extensive use is increased. Furthermore, when said promoted zeolite materials are used as catalysts in processes where the feedstream comprises both C2 or C3 alcohol and water, the lifetime of the catalyst may be extended even further. It is believed that the presence of promoter elements in the zeolite may impede dealumination of the zeolite by the high temperature water vapour, which would otherwise lead to a reduction in catalytic activity due to coking and other catalyst deactivation mechanisms.

Accordingly, in preferred embodiments, the ZSM5 zeolite material or the MCM22 zeolite material are promoted zeolite materials that have reduced acidity as determined by temperature programmed desorption of ammonia, relative to the corresponding unpromoted zeolite material with equivalent Si/Al ratio. More preferably, the ZSM5 zeolite material or the MCM22 zeolite material have one or both of: i) a different acid site strength distribution as determined by temperature programmed desorption of ammonia, as the corresponding unpromoted zeolite material with equivalent Si/Al ratio; and ii) a different total number of acid sites as determined by temperature programmed desorption of ammonia, as the corresponding unpromoted zeolite material with equivalent Si/Al ratio.

Temperature programmed desorption of ammonia is a technique known in the art. Whether or not a given promoted zeolite material has reduced acidity; a different acid site strength distribution; and/or a different total number of acid sites can be determined simply by analysis of the temperature programmed desorption of ammonia spectrum for a given zeolite material.

In some embodiments, the ZSM5 zeolite material or the MCM22 zeolite material are promoted zeolite materials comprising one or more promoter elements selected from boron, phosphorus, gallium, magnesium, zinc, potassium and zirconium. In some embodiments, the one or more promoter elements are present in the zeolite material in an amount of from 0.5 wt % to 5 wt %, preferably from 0.75 wt % to 3.25 wt %.

Preferably, the catalyst comprises a ZSM5 zeolite material, wherein the ZSM5 zeolite material comprises a promoted ZSM5 zeolite material promoted with the elements boron or phosphorus. The boron and phosphorus may be present in any suitable amount so as to reduce the acidity of the zeolite material as discussed above. Preferably, the boron or phosphorus are present in the ZSM5 material in an amount of from 0.75% to 3.25% by weight, more preferably from 0.8% to 3.2% by weight, still more preferably from 0.9% to 3.1% by weight, and most preferably from 1% to 3% by weight. In preferable embodiments, the ZSM5 zeolite material that is promoted with boron or phosphorus has a Si/Al ratio of from 25 to 90, and most preferably from 25 to 35 or 75 to 85.

In some embodiments, the ZSM5 zeolite material has an Si/Al ratio of 75 to 85, wherein the ZSM5-zeolite material comprises from 0.75% by weight phosphorus to 1.25% by weight phosphorus, more preferably from 0.8% to 1.2% by weight phosphorus, still more preferably from 0.9% to 1.1% by weight phosphorus, and most preferably about 1% by weight phosphorus. In highly preferred embodiments, the Si/Al ratio is 80 and the ZSM5 zeolite material comprises 1% by weight phosphorus.

In some embodiments, the ZSM5 zeolite material has an Si/Al ratio of 25 to 30, wherein the ZSM5-zeolite material comprises from 0.75% by weight to 3.25% by weight phosphorus, more preferably from 0.8% to 3.2% by weight, still more preferably from 0.9% to 3.1% by weight, and most preferably from 1% to 3% by weight phosphorus. In highly preferred instances, the ZSM-5 zeolite material has an Si/Al ratio of 30 and the ZSM5-zeolite material comprises 1% by weight phosphorus, 2% by weight phosphorus, or 3% by weight phosphorus.

In some embodiments, the ZSM5 zeolite material has an Si/Al ratio of 75 to 85, wherein the ZSM5-zeolite material comprises from 0.75% by weight boron to 3.25% by weight boron, preferably from 0.8% to 3.2% by weight boron, more preferably from 0.9% to 3.1% by weight boron and most preferably from 1% to 3% by weight boron. In preferred embodiments, the Si/Al ratio of the ZSM5 zeolite material is 80. In preferred embodiments, the ZSM5-zeolite material comprises 1% by weight boron, 2% by weight boron, or 3% by weight boron. In a highly preferred embodiment, the Si/Al ratio of the ZSM5 zeolite material is 80 and the ZSM5-zeolite material comprises 1% by weight boron, 2% by weight boron, or 3% by weight boron.

In some embodiments, the ZSM5 zeolite material has an Si/Al ratio of 25 to 35, wherein the ZSM5-zeolite material comprises from 0.75% by weight boron to 3.25% by weight boron, preferably from 0.8% to 3.2% by weight boron, more preferably from 0.9% to 3.1% by weight boron and most preferably from 1% to 3% by weight boron. In preferred embodiments, the Si/Al ratio of the ZSM5 zeolite material is 80. In preferred embodiments, the ZSM5-zeolite material comprises 1% by weight boron, 2% by weight boron, or 3% by weight boron. In a highly preferred embodiment, the Si/Al ratio of the ZSM5 zeolite material is 80 and the ZSM5-zeolite material comprises 1% by weight boron, 2% by weight boron, or 3% by weight boron.

The MCM22 and ZSM5 zeolite materials are readily available from a variety of sources, or can be synthesised using methods well known in the art. The promoted zeolite materials discussed above can also be synthesised using methods known in the art, and examples of these are discussed in further detail below. In some embodiments, promoted zeolites are manufactured directly from zeolite powders. Where zeolite catalysts comprise binder, carrier or support material, in some embodiments, zeolite powders are promoted before being processed with the binder, carrier or support material, such as processed by extrusion. In other embodiments, the catalysts are processed with support, binder or carrier material, such as by extrusion, prior to being converted into the promoted form of the catalyst.

As discussed above, a surprising advantage associated with the use of MCM22 and ZSM5 zeolite materials in the process of the invention, is that the catalytic activity of the catalyst and their selectivity for the production of C3 and C4 aliphatic hydrocarbons can be rejuvenated simply and to a great extent.

Accordingly, in some embodiments, the process further comprises stopping the continuous process of steps a) to c); and contacting the catalyst with air or oxygen under conditions sufficient to rejuvenate the catalyst. In some embodiments, the catalyst is rejuvenated such that the catalyst has an activity and selectivity equivalent to an initial activity and selectivity of the catalyst. Preferably, the catalyst is rejuvenated such that the catalyst has an activity and selectivity equivalent to 70% or more, 80% or more, or 90% or more of an initial activity and selectivity of the catalyst. In highly preferable embodiments, the catalyst is rejuvenated such that the catalyst has an activity and selectivity equivalent to 100% of an initial activity and selectivity of the catalyst.

The term initial selectivity and activity of the catalyst as used herein is used to refer to the activity and selectivity of the catalyst before it has ever been used in a process for the selective production of BioLPG as disclosed herein. The term activity as used herein is used to refer to the ability of the catalyst is chemically convert a process feedstock into chemical products. The term selectivity as used herein is used to refer to the ability of the catalyst to produce a specific chemical product over an alternative chemical product. For example, a catalyst selectivity of 40% for C3 and C4 aliphatic hydrocarbons means that 40% of the chemical products produced by the catalyst are C3 and C4 aliphatic hydrocarbons.

In some embodiments, the process further comprises stopping the continuous process of steps a) to c); and contacting the catalyst with air or oxygen. Preferably, this contacting is done at a temperature of from 300° C. to 600° C., more preferably from 400° C. to 550° C. Preferably, the contacting is done for a time period of from 1 hour to 20 hours, and more preferably from 5 hours to 15 hours. In some embodiments, the contacting is done at a temperature of from 400° C. to 550° C. for a time period of from 5 hours to 15 hours. Typically, these conditions will be sufficient to rejuvenate the catalyst.

In some embodiments, the process may further comprise recovering an aromatics product stream from the reaction vessel. The aromatics product stream typically comprises benzene, toluene, ethyl benzene, p-xylene, 1-ethyl-3-methyl-benzene, 1,2,4-trimethyl-benzene, 1-methyl-2-isopropyl-benzene, or a combination thereof, although it will be understood that other similar aromatic compounds may also be present in the aromatics product stream. A surprising advantage of the process of the invention is that the process also shows high selectivity for aromatics over other hydrocarbons. In this respect, the major hydrocarbon product of the process of the invention is LPG, and the second most abundant product are aromatic hydrocarbons. Typically, the process produces C3-C4 hydrocarbons (i.e. the LPG product) and aromatic hydrocarbons in a mass ratio of from 1:1 (C3-C4 hydrocarbons/aromatics) to 2:1, preferably from 1.2 to 1 to 1.5:1. Aromatic hydrocarbons are useful in many applications. A key application is as a component of certain jet fuels. The process of the invention thus finds utility in the provision of bio-derived jet fuels or components for use in bio-derived jet fuels.

According to a second aspect of the invention, there is provided a process for the selective production of BioLPG from C2 or C3 aliphatic alcohols, wherein the process comprises:

(a) introducing a feedstream comprising one or more C2 or C3 aliphatic alcohols into a reaction vessel comprising a catalyst, wherein the catalyst comprises a ZSM5 zeolite material, an MCM22 zeolite material, or a combination thereof;

(b) contacting the feedstream and catalyst within the reaction vessel at a temperature of from 250° C. to 750° C.; and (c) recovering a product stream comprising C3 and/or C4 aliphatic hydrocarbons from the reaction vessel;

wherein the process is a continuous flow process, and wherein the process comprises introducing the feedstream to the reactor vessel at a flow rate of from 1 μL to 10 μL per minute per 150 mg of catalyst present in the reactor vessel, and wherein the process further comprises passing an inert gas such as argon through the reaction vessel during contacting step b), wherein the inert gas is introduced into the reaction vessel at a flow rate of from 0.5 ml/min per 150 mg of catalyst to 10 ml/min per 150 mg of catalyst, preferably from 0.5 ml/min per 150 mg of catalyst to 5 ml/min per 150 mg of catalyst, more preferably 1.5 ml/min to 5 ml/min per 150 ml of catalyst and more preferably from 2 ml/min to 5 ml/min per 150 mg of catalyst.

Preferably, the process comprises introducing the feedstream to the reactor vessel at a flow rate of from 1 μL to 3 μL per minute per 150 mg of catalyst present in the reactor vessel, and wherein the process further comprises passing an inert gas such as argon through the reaction vessel during contacting step b), wherein the inert gas is introduced into the reaction vessel at a flow rate of from 0.5 ml/min per 150 mg of catalyst to 5 ml/min per 150 mg of catalyst. In some instances, the inert gas is introduced into the reaction vessel at a flow rate of from 0.5 ml/min to 1.5 ml/min, per 150 ml of catalyst or from 0.75 ml/min to 1.25 ml/min per 150 mg of catalyst.

Preferably, the process is as further described above in accordance with the first aspect of the invention.

According to a third aspect of the invention, there is provided a catalyst comprising a ZSM5 zeolite material, an MCM22 zeolite material, or a combination thereof, wherein the ZSM5 zeolite material has a Si/Al ratio of from 20 to 150, and wherein the MCM22 zeolite material has a Si/Al ratio of from 10 to 70, and wherein the ZSM5 zeolite material or the MCM22 zeolite material are promoted zeolite materials that have reduced acidity as determined by temperature programmed desorption of ammonia, relative to the corresponding unpromoted zeolite material with equivalent Si/Al ratio.

Preferably, the catalyst of the third aspect of the invention is as defined above in accordance with the first aspect of the invention.

The catalyst of the third aspect of the invention is a BioLPG production catalyst.

According to a fourth aspect of the invention, there is provided the use of a catalyst according to the third aspect of the invention for the conversion of C2 or C3 aliphatic alcohols to C3 and/or C4 aliphatic hydrocarbons.

Preferably, the use comprises using the catalyst in a process according to the first or second aspects of the invention.

Preferably, the use comprises producing the C3 and/or C4 aliphatic hydrocarbons with a yield of at least 30%, preferably at least 40%, and most preferably at least 50%.

According to a fifth aspect of the invention, there is provided a process for rejuvenating a deactivated BioLPG production catalyst comprising a ZSM5 zeolite material or an MCM22 zeolite material, wherein the method comprises contacting the catalyst with air or oxygen.

Preferably, the method comprises contacting the catalyst with air or oxygen at a temperature of from 300° C. to 600° C., more preferably from 400° C. to 550° C.

Preferably, the method comprises contacting the catalyst with air or oxygen for a time period of from 1 hour to 20 hours, more preferably for a time period of from 5 hours to 15 hours.

More preferably, the method comprises contacting the catalyst with air or oxygen at a temperature of from 300° C. to 600° C. for a time period of from 1 hour to 20 hours. Most preferably, the method comprises contacting the catalyst with air or oxygen at a temperature of from 400° C. to 550° C. for a time period of from 5 hours to 15 hours.

In some embodiments, the catalyst is rejuvenated such that the catalyst has an activity and selectivity equivalent to an initial activity and selectivity of the catalyst. Preferably, the catalyst is rejuvenated such that the catalyst has an activity and selectivity equivalent to 70% or more, 80% or more, or 90% or more of an initial activity and selectivity of the catalyst. In highly preferable embodiments, the catalyst is rejuvenated such that the catalyst has an activity and selectivity equivalent to 100% of an initial activity and selectivity of the catalyst.

Preferably, the catalyst is as defined in accordance with the first and third aspects of the invention.

BRIEF DESCRIPTION OF THE DRAWINGS

FIGS. 47 and 48 show porosity data for various zeolite catalysts.

FIGS. 55 to 62 show general trends in selectivity for tested catalysts at different operating conditions.

DETAILED DESCRIPTION OF THE INVENTION

Example 1

Testing was performed with the commercially available zeolites ZSM5, MCM22 and SAPO34. The one or more C2 or C3 aliphatic alcohols used as a feedstream for the process comprised ethanol.

Reaction vessels were loaded with the amounts of catalyst and silicon carbide shown in Table 1.

TABLE 1

| Reaction Vessel | Catalyst | Mass of catalyst (mg) | Mass of SiC (mg) |
|---|---|---|---|
| 1 | Blank | 0 | 500 |
| 2 | ZSM5 | 100 | 200 |
| 3 | MCM22 | 100 | 0 |
| 4 | SAPO34 | 200 | 0 |
| 5 | SAPO34 | 100 | 100 |
| 6 | ZSM5 | 200 | 100 |

Prior to loading in the reaction vessels, all zeolites were exposed to air at 550° C. for 5 hours to make sure they were in the H-form. After loading of the reaction vessels, the reaction vessels were heated under air flow (25 ml/min/ block of eight tubes) to 460° C., and held for 7 hours. The tubes were cooled to 400° C. whilst purging with Argon and the reaction pressure set at 5 bar. Ethanol was then introduced to each reaction vessel at a rate of 2.5 µL/min at a temperature of 400° C. Argon was introduced at a rate of 0.625 ml/min per reaction vessel tube as the internal standard and nitrogen was introduced to each catalyst bed in each reaction vessel at a rate of 37.5 ml/min per reaction vessel tube as a diluent gas. The purpose of the nitrogen diluent gas is simply to increase the space velocity for subsequent gas chromatography analysis.

Figure 1:
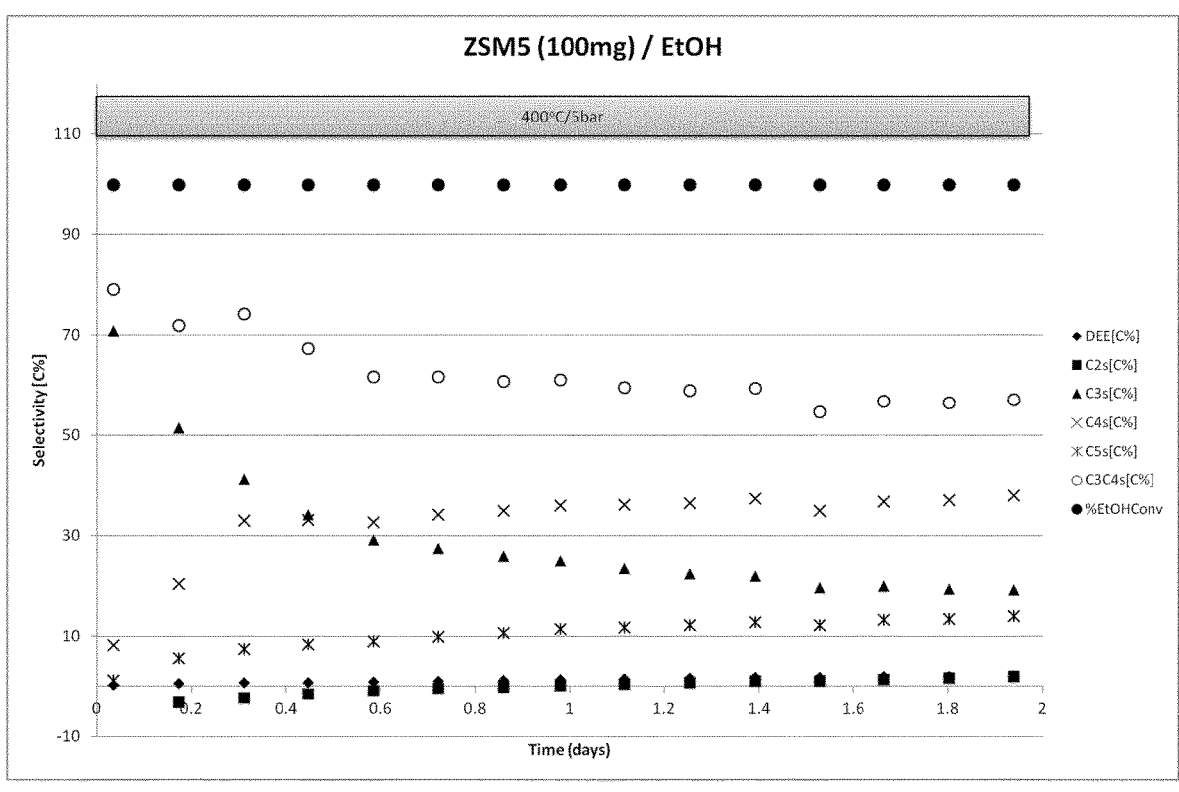
FIG. 1 shows the product selectivity of a process of the invention conducted using a 100 mg of a ZSM5 zeolite catalyst.
Figure 2:
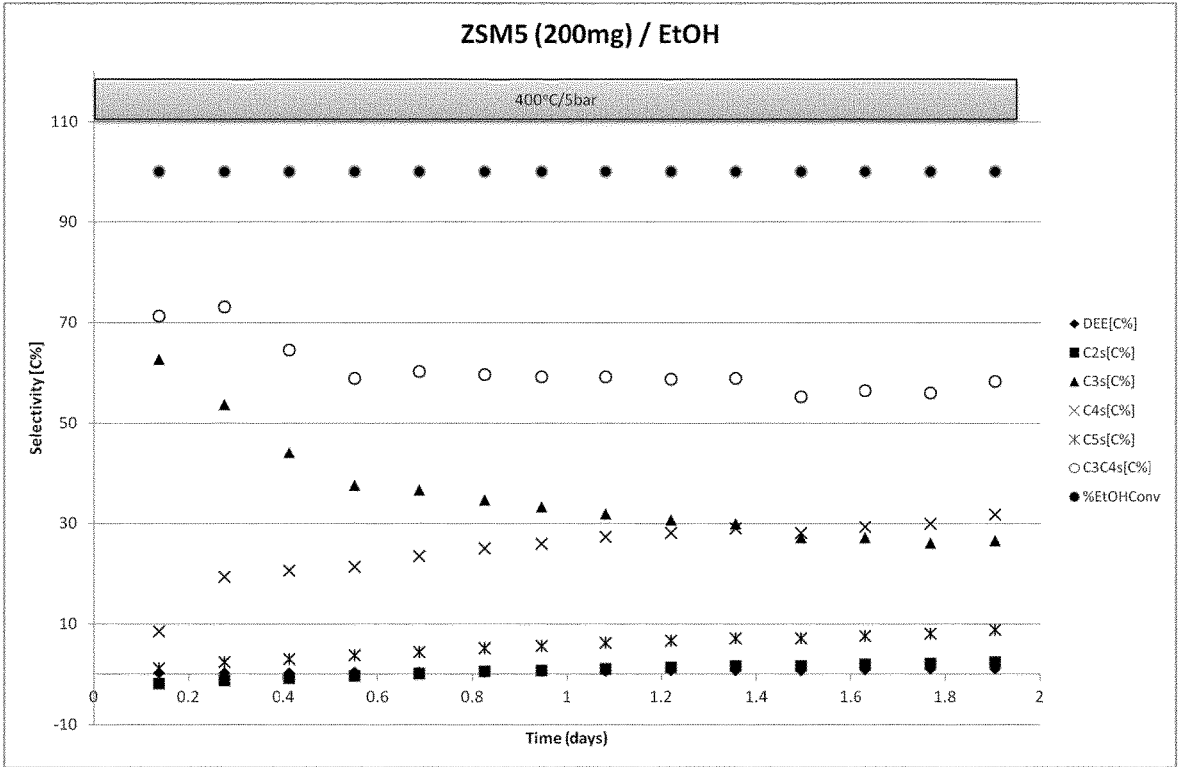
FIG. 2 shows the product selectivity of a process of the invention conducted using a 200 mg of a ZSM5 zeolite catalyst.
Figure 3:
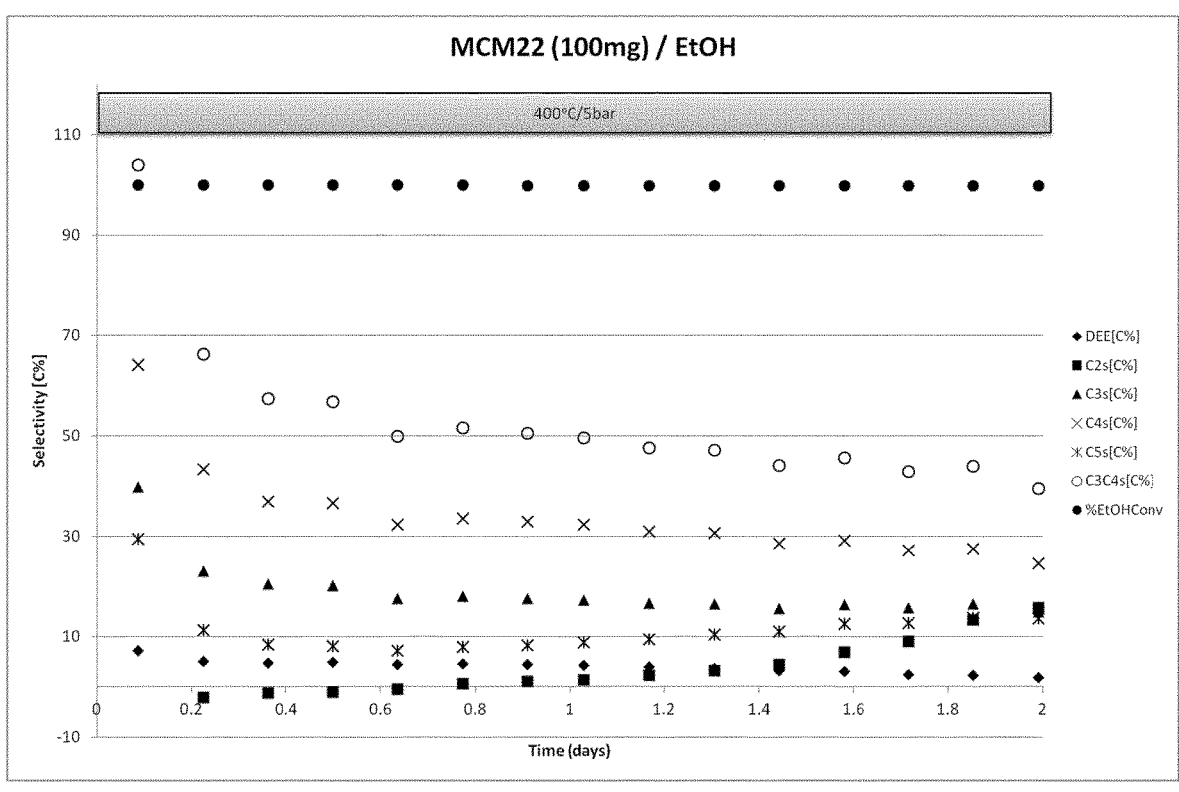
FIG. 3 shows the product selectivity of a process of the invention using 100 mg of zeolite catalyst MCM22.
Figure 4:
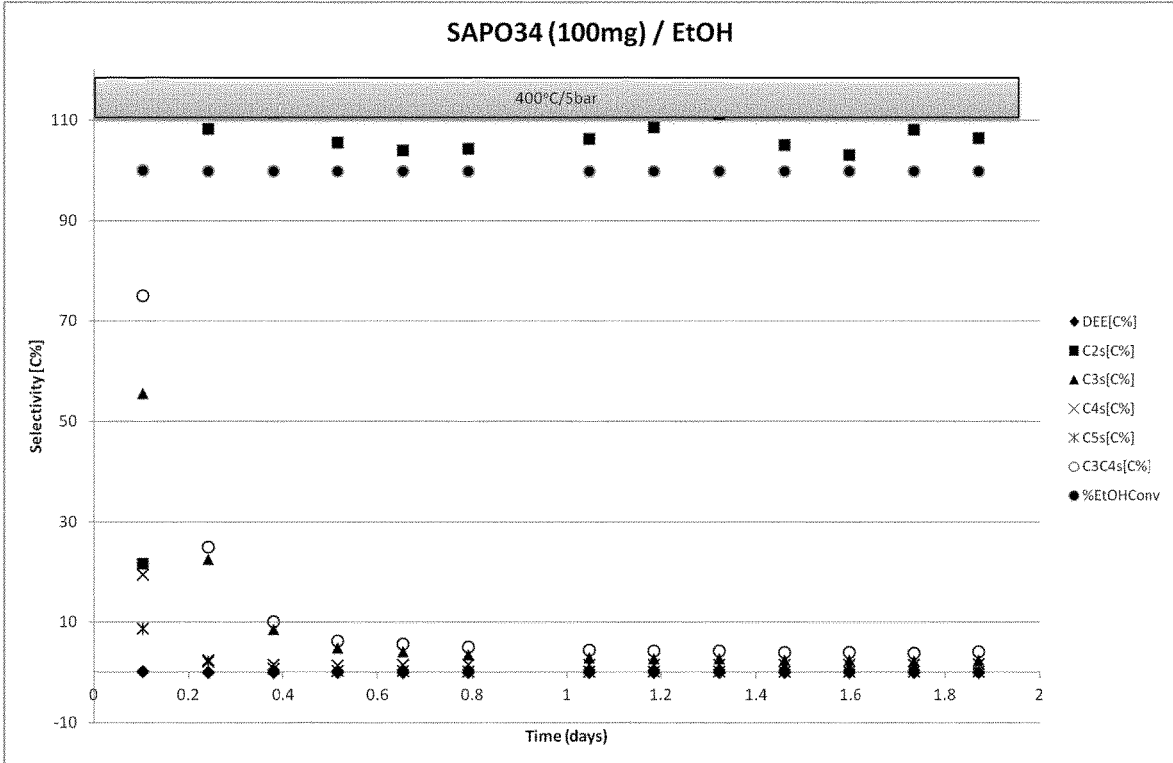
FIG. 4 shows the product selectivity of a process for converting ethanol into hydrocarbons using 100 mg of zeolite catalyst SAPO34.
Figure 5:
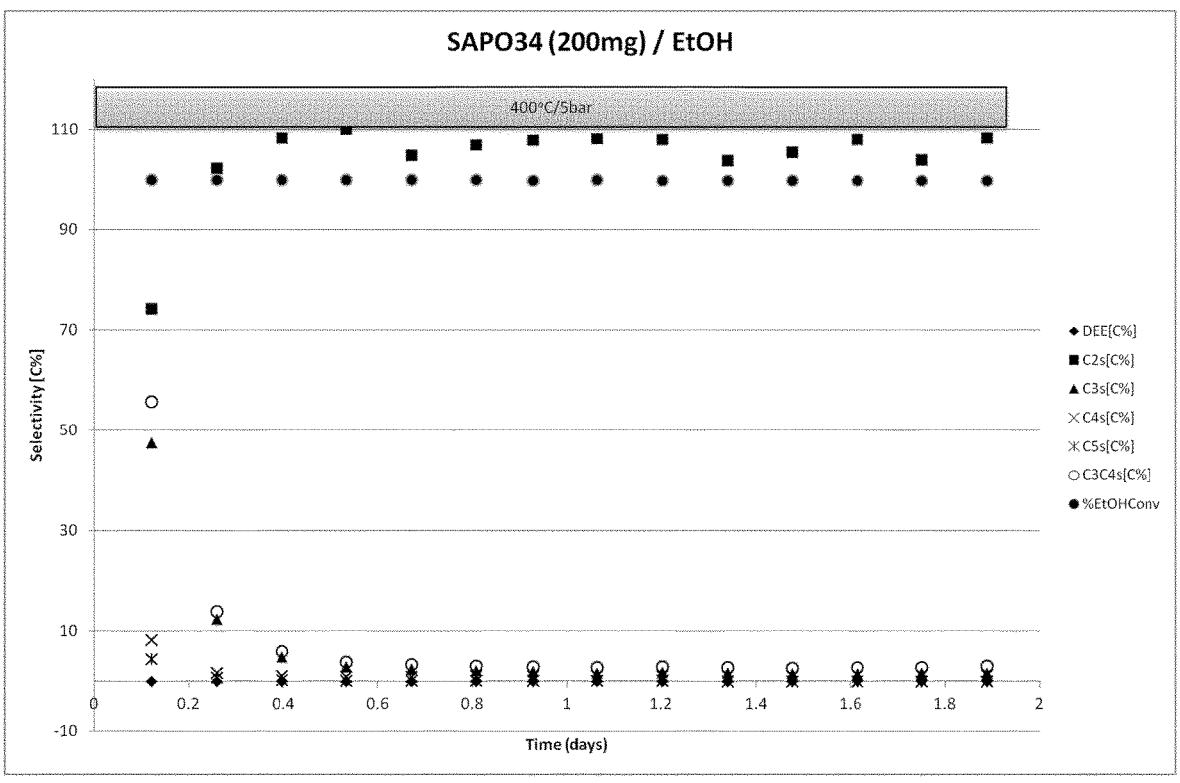
FIGS. 5 & 6 show the product selectivity for C3/C4 hydrocarbons of different zeolite catalysts in processes of converting ethanol into hydrocarbons.
Figure 6:
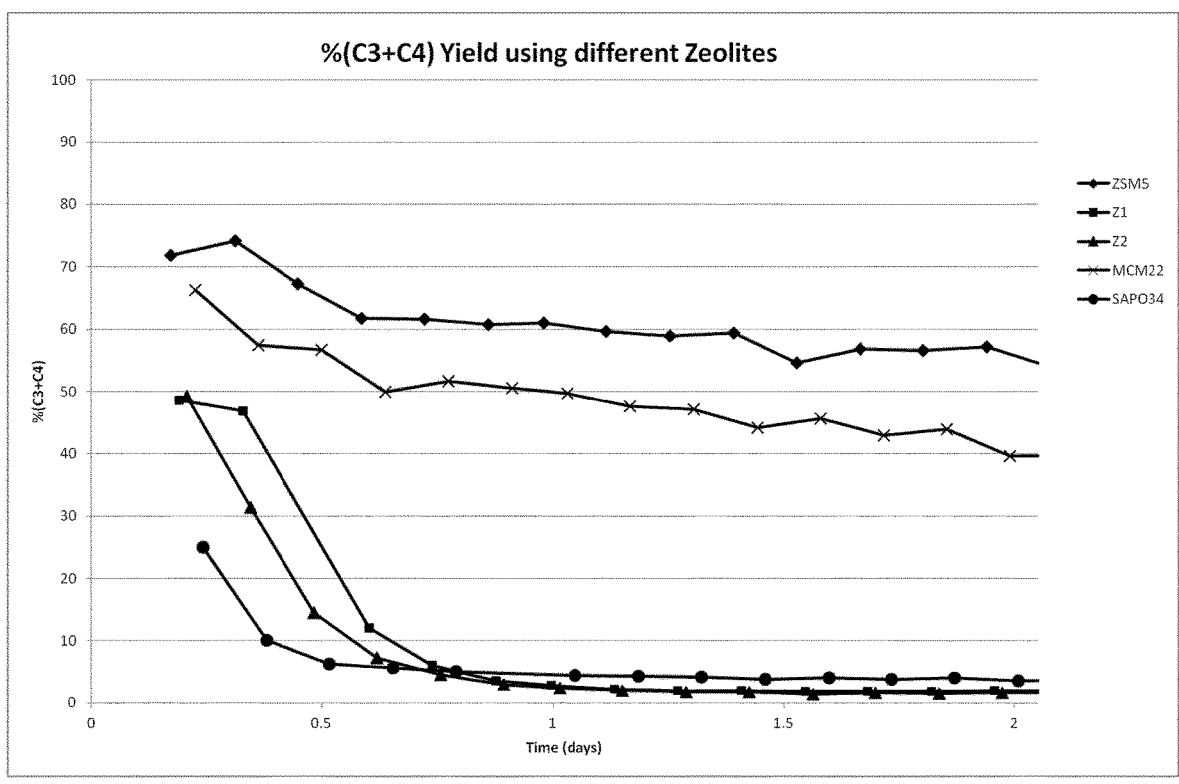
Figure 7:
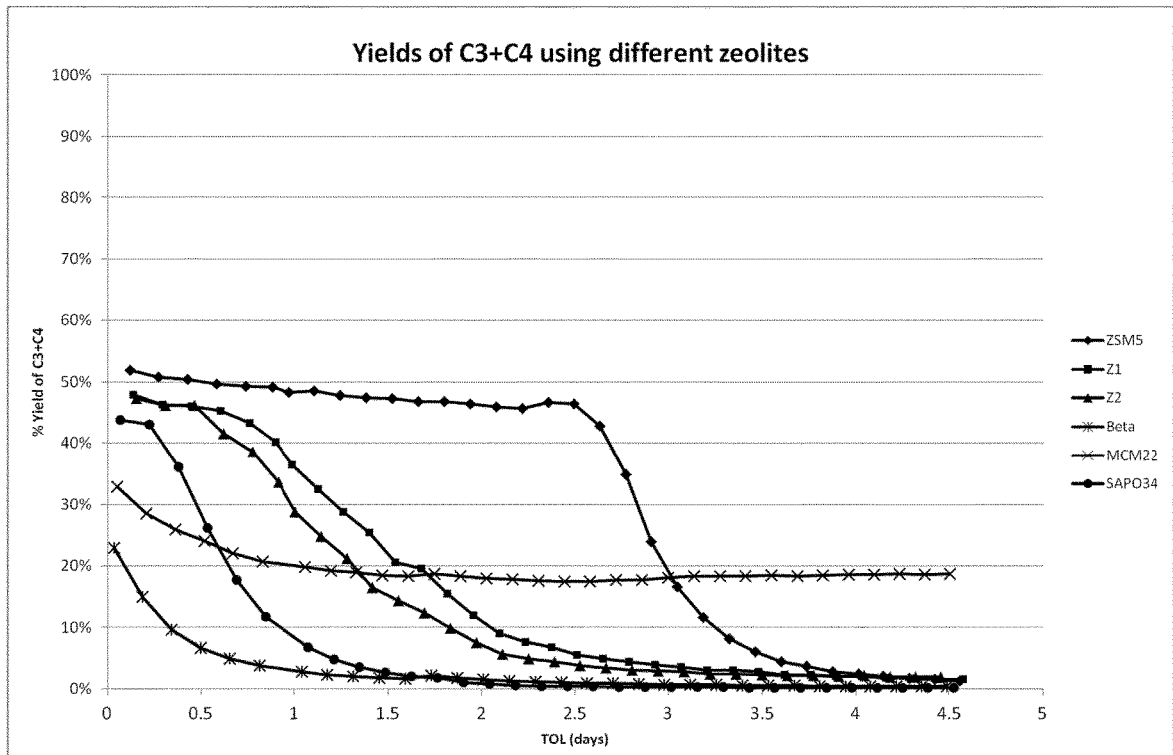
FIG. 7 shows the product selectivity of a process of converting ethene into hydrocarbons using ZSM5 as the catalyst.
Figure 8:
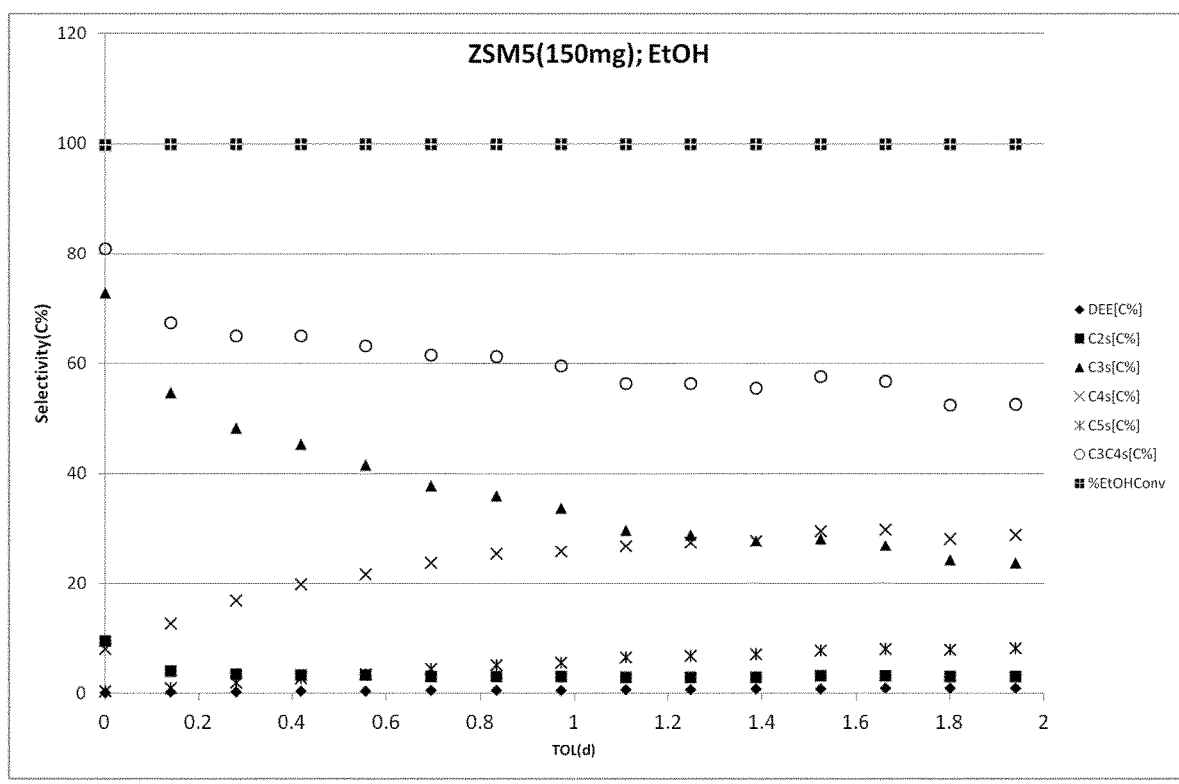
FIGS. 8 to 16 show the product selectivity of processes of the invention where the processes are carried out for different time periods, with differing amounts of catalyst.

The selectivity of each catalyst over time for formation of hydrocarbons of different chain length and diethyl ether are shown in FIGS. 1 to 7. FIG. 8 contrasts the selectivity over time for C3 and C4 aliphatic hydrocarbon formation of the different zeolites. FIG. 8 shows that the initial selectivity of the ZSM5 and MCM22 catalysts for C3 and C4 aliphatic hydrocarbon formation is significantly greater than the other zeolites. It can also be seen from FIG. 8 that after a short time period, the selectivity of all catalyst for formation of C3 and C4 aliphatic hydrocarbons decreases. However, this decrease in selectivity is significantly less for MCM22 and ZSM5 than it is for the other zeolites.

In all cases, very high ethanol to hydrocarbon product conversions were obtained of roughly 100%. For zeolite SAPO3, almost all ethanol was converted to ethylene and almost no other hydrocarbons were produced after several hours of running the reaction.

ZSM5 had a selectivity for C3 and C4 aliphatic hydrocarbons of around 55% to 60%. MCM22 had a selectivity for C3 and C4 aliphatic hydrocarbons of around 45% to 55%.

Figure 9:
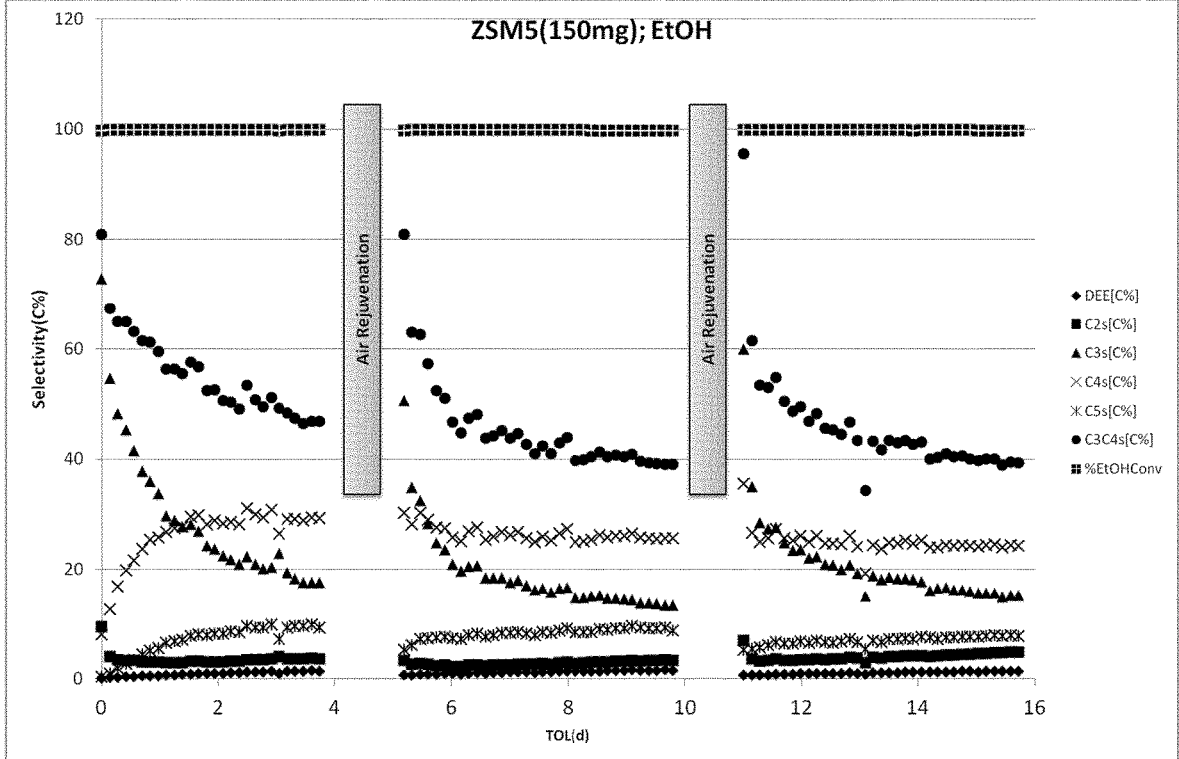

A similar experiment was carried out using ethene as a feedstream instead of ethanol. The results of this experiment with the different catalysts are shown in FIG. 9. It can be seen from FIG. 9 that the selectivities and lifetime for each catalyst are different when ethene is used as a feedstock instead of ethanol (as shown in FIG. 8). When using ethene as a feed, the zeolites suffered from much faster activation than when using ethanol as a feed. It can also be seen that C3/C4 (i.e. LPG) yields are higher when ethanol is used as a feed for the process than when ethene is used as a feed, for the MCM22 and ZSM5 zeolite catalysts.

Example 2

A similar experiment to Example 1 was carried out using only MCM22 and ZSM5 as catalysts, but investigating the effects of having the process online as a continuous process for a longer period of time.

Reaction vessels were loaded with the amounts of catalyst and silicon carbide shown in Table 2.

TABLE 2

| Reaction Vessel | Catalyst | Mass (mg) | SiC (mg) |
|---|---|---|---|
| 1 | Blank | 0 | 500 |
| 2 | ZSM5 | 150 | 150 |
| 3 | ZSM5 | 100 | 200 |
| 4 | ZSM5 | 50 | 300 |
| 5 | ZSM5 | 25 | 300 |
| 6 | MCM22 | 150 | 0 |
| 7 | MCM22 | 100 | 50 |
| 8 | MCM22 | 50 | 100 |

Prior to loading in the reaction vessels, all zeolites were exposed to air at 550° C. for 5 hours to make sure they were in the H-form. After loading of the reaction vessels, the reaction vessels were heated under air flow (35 ml/min/ block of eight tubes) to 470° C., and held for 7 hours. The tubes were cooled to 400° C. whilst purging with Argon and the reaction pressure set at 5 bar. Ethanol was then introduced to each reaction vessel at a rate of 2.5 μL/min at a temperature of 400° C. Argon was introduced at a rate of 0.625 ml/min per reaction vessel tube as the internal standard and nitrogen was introduced to each catalyst bed in each reaction vessel at a rate of 37.5 ml/min per reaction vessel tube as a diluent gas. The temperature was increased to 425° C. after the reaction had been online for 11 days. The purpose of the nitrogen diluent gas is simply to increase the space velocity for subsequent gas chromatography analysis.

In this experiment, different catalysts loadings were used to try and determine total ethanol conversion per gram of catalyst.

It was also investigated whether in situ rejuvenation of the catalysts could be achieved, which would extend the overall lifetimes of the catalysts. Accordingly, a first rejuvenation of the catalysts were carried out after 4 days online followed by another 4 days of catalysis prior to a second rejuvenation followed by a further 5 days of catalysis.

The results of the experiments are shown in FIGS. 10 to 18.

Figure 10:
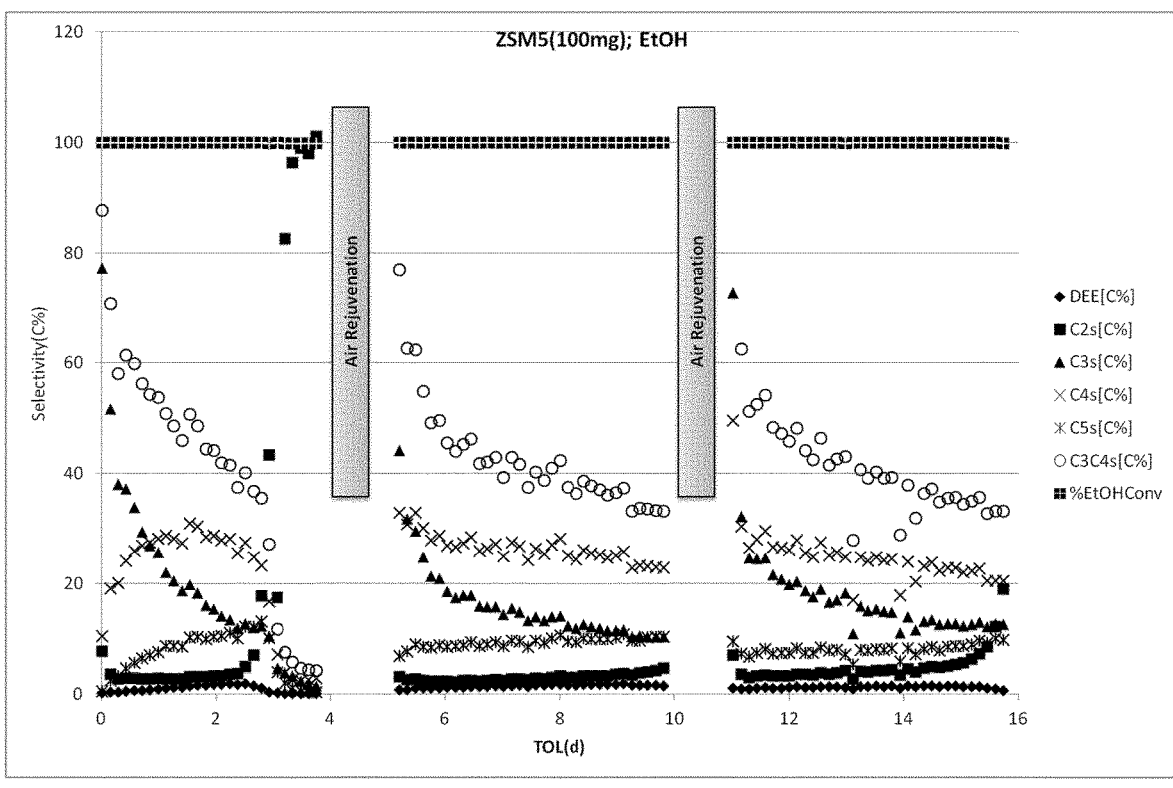
Figure 11:
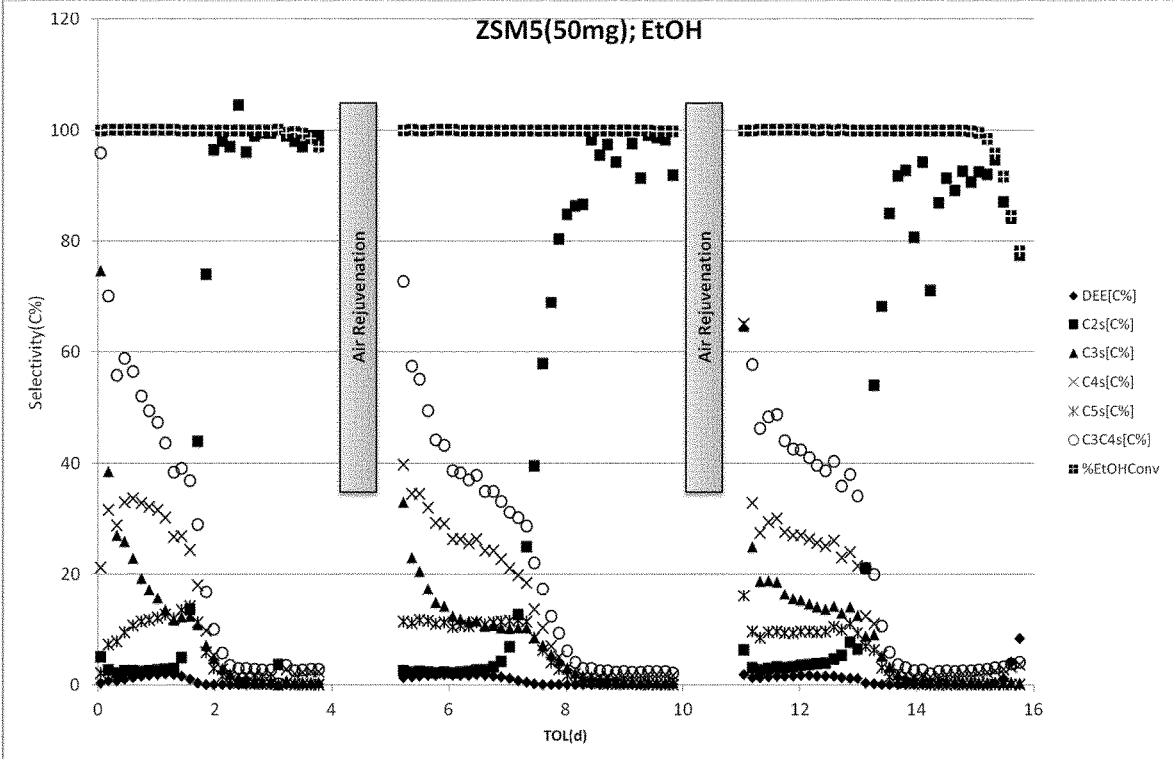
Figure 12:
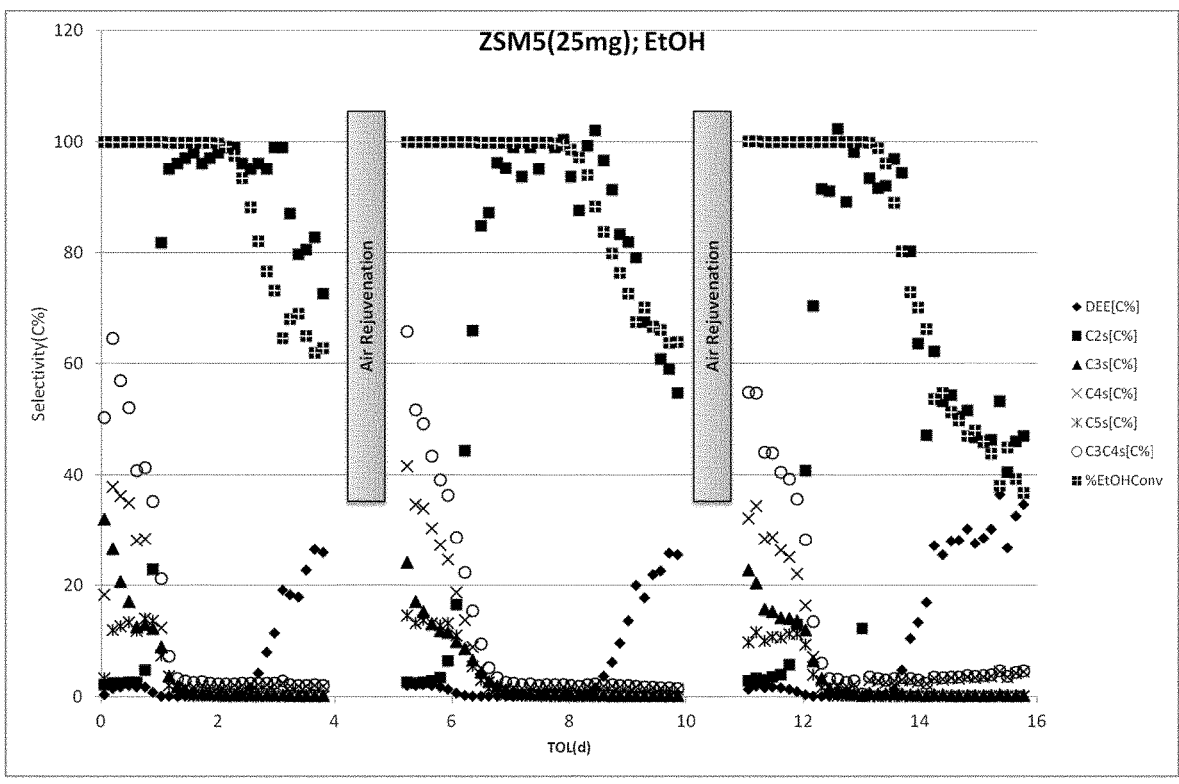
Figure 13:
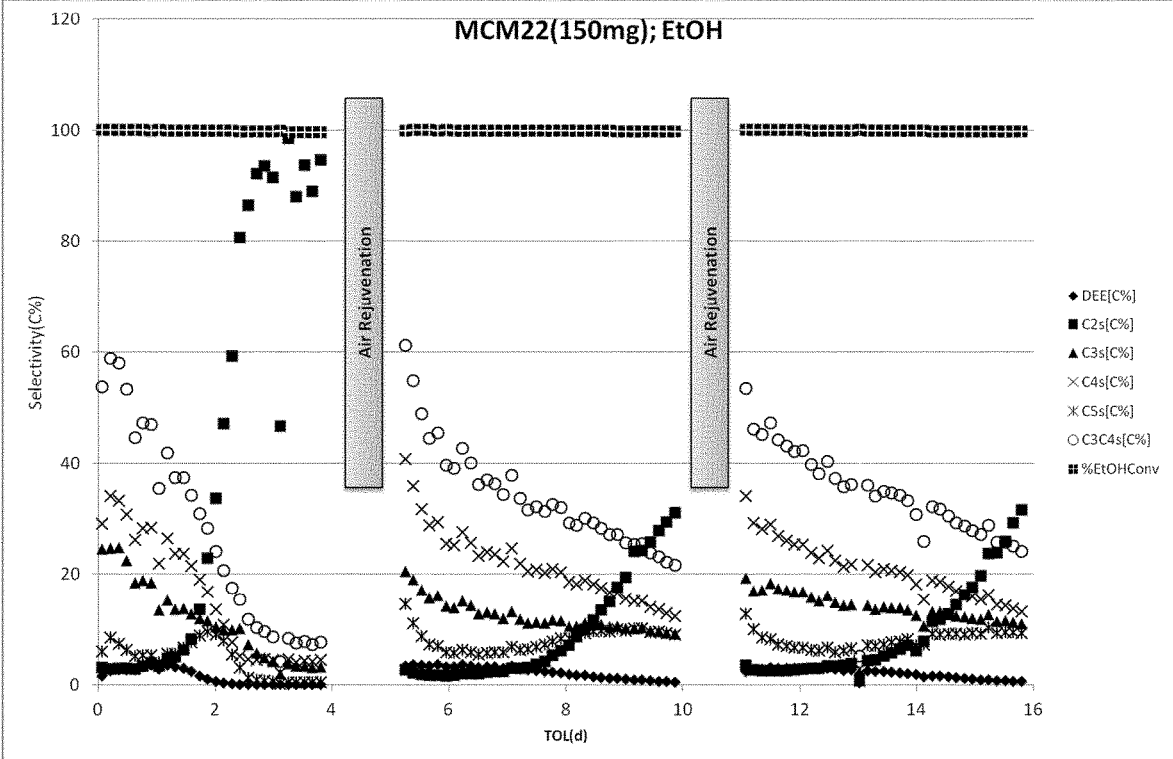
Figure 14:
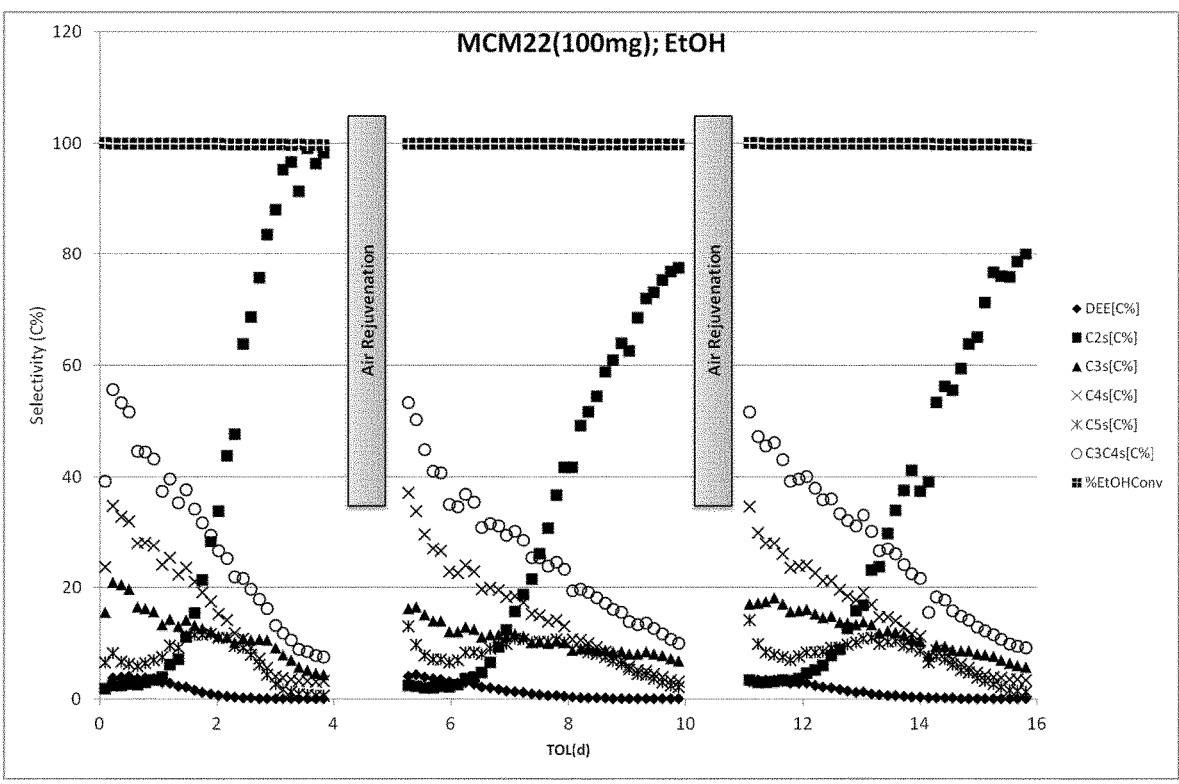

FIG. 10 shows that the initial selectivity for C3 and C4 hydrocarbons with ZSM5 is high at roughly 55% to 65%. It was also found that for the first 24 hours online the main fraction was C3 but that this ratio changes in favour of C4 compounds after 1 day online. FIG. 11 shows that the selectivity for C3 and C4 hydrocarbons gradually drops after several days online.

The data in FIGS. 11 to 14 which contrasts different loadings of ZSM5 catalyst shows the start of catalyst deactivation at different times online. This is indicative that catalyst deactivation is more affected by the total ethanol concentration than the time online. An indicator of catalyst deactivation is the sudden increase of C2 hydrocarbons as the zeolite starts to struggle to convert the C2 hydrocarbons to C3 and C4 hydrocarbons. If the appearance of C2 hydrocarbons is taken as the start of significant deactivation of the catalyst, then the data in Table 3 shows that ZSM5 deactivation starts after around 100 ml of ethanol has been converted per gram of ZSM5.

TABLE 3

| ZSM5 | Time online of ethene concentration occurrence (hours) | Total ethanol delivered (ml) at flow rate of 2.5 μL/min | Total ml ethanol per gram of ZSM5 |
|---|---|---|---|
| 25 mg | 18 | 2700 μL | 108 ml/g |
| 50 mg | 35 | 5250 μL | 105 ml/g |
| 100 mg | 62 | 9375 μL | 94 ml/g |

The data in FIGS. 11 to 14 also shows significant deactivation of ZSM5 for the experiments performed at lower catalyst loadings. However, in situ air rejuvenation at 470° C. afforded near complete recovery of ZSM5 activity and selectivity. In some cases (for example, in the data shown in FIG. 12), the first rejuvenation actually improved the activity and selectivity of the catalyst over the initial activity and selectivity. Similar rejuvenation of activity and selectivity was achieved after the second air rejuvenation.

Figure 15:
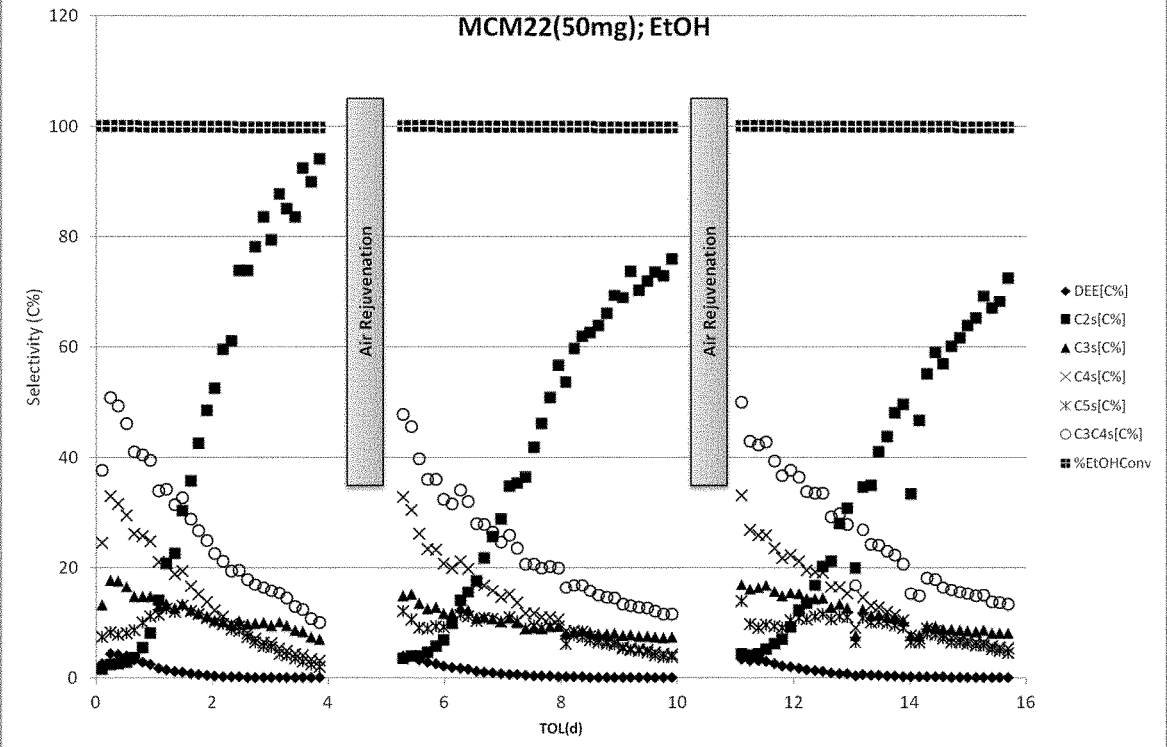
Figure 16:
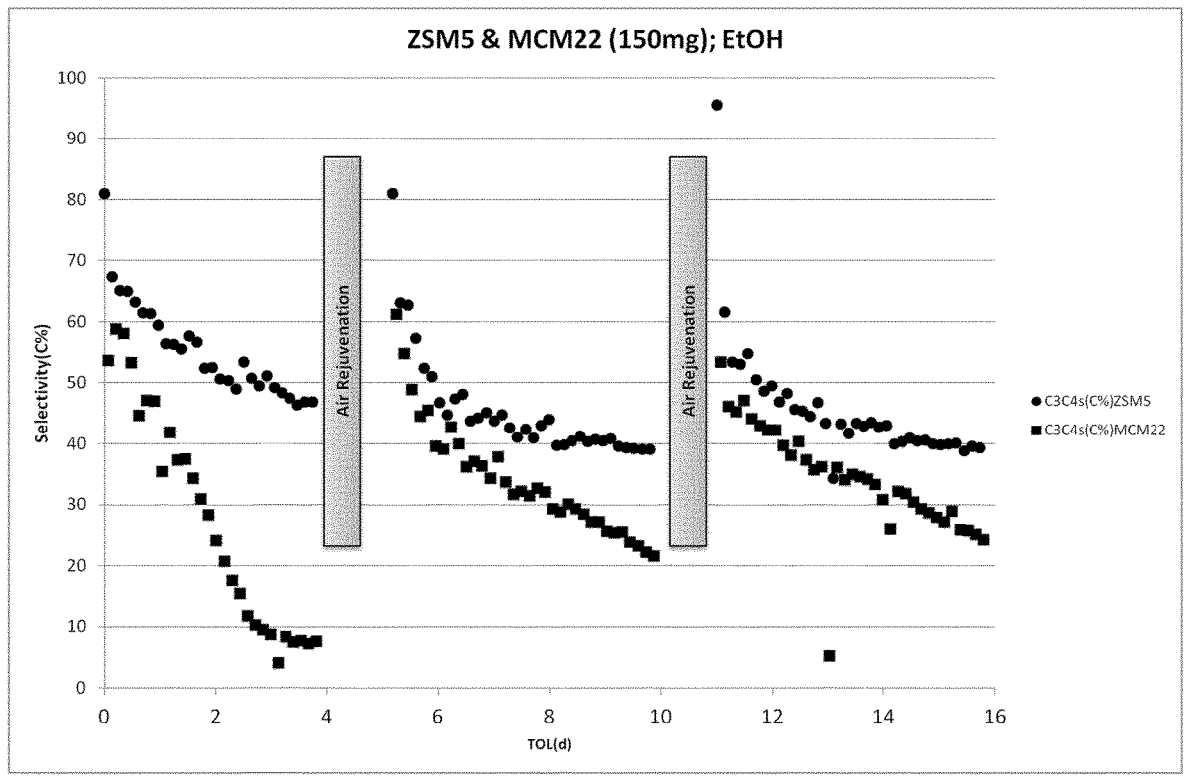
Figure 17:
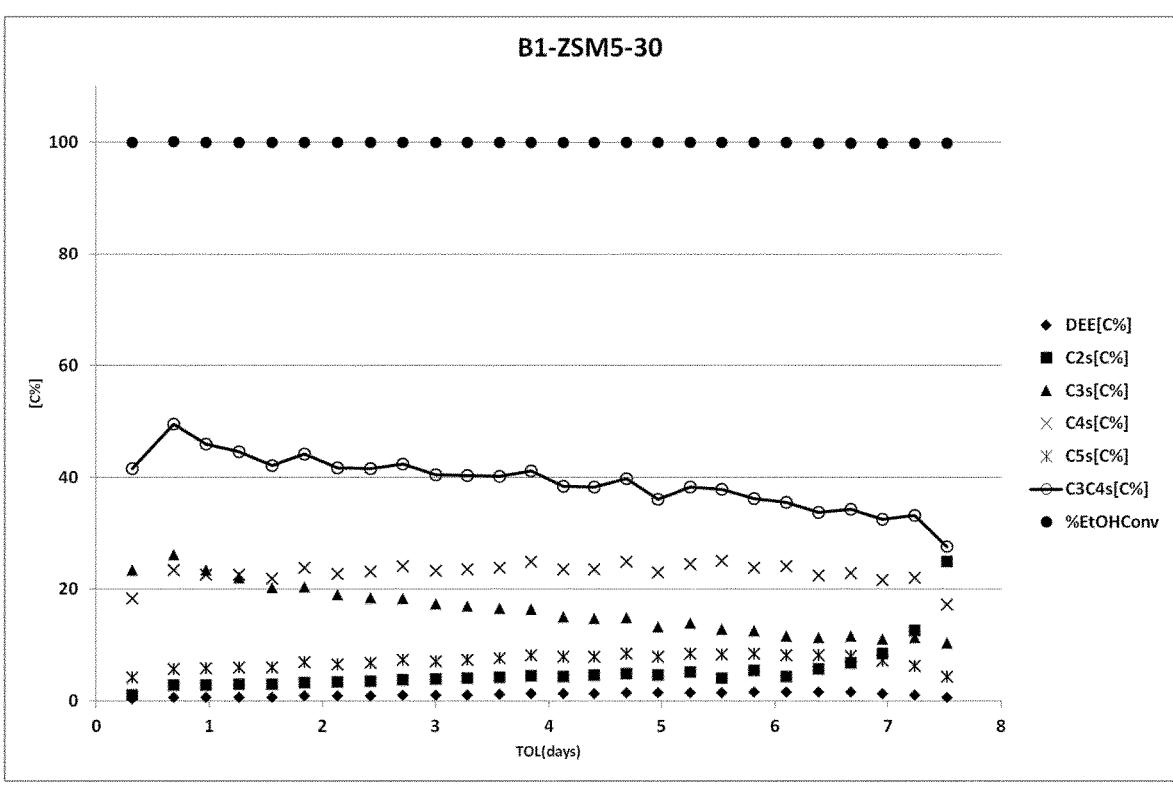
FIG. 17 shows the product selectivity of a process of the invention conducted using a boron promoted ZSM5 zeolite catalyst.

FIG. 15 shows that MCM22 shows a selectivity for C3 and C4 hydrocarbons over the first 24 hours online of about 45% to 55%. However after around 1 day online, the MCM22 catalyst starts to deactivate, as is shown by the increase in C2 hydrocarbon production. A similar comparison of the MCM22 data as done for the ZSM5 data discussed above shows that MCM22 deactivation starts after a total ethanol conversion of roughly 33 ml per gram of MCM22. However, advantageously, at all catalyst loadings, ethanol conversion was roughly 100%.

The deactivation of MCM22 was more marked than that of ZSM5 as ethene started to dominate after a shorter period online. Fortunately, once again an in-situ air rejuvenation at 470° C. afforded almost complete recovery of the MCM22 activity and selectivity. Furthermore, a similar recovery of activity and selectivity was observed after the second air rejuvenation. It was also noticeable that the MCM22 performance in terms of catalyst lifetime improved noticeably after the first and second rejuvenation relative to the fresh catalyst.

Figure 18:
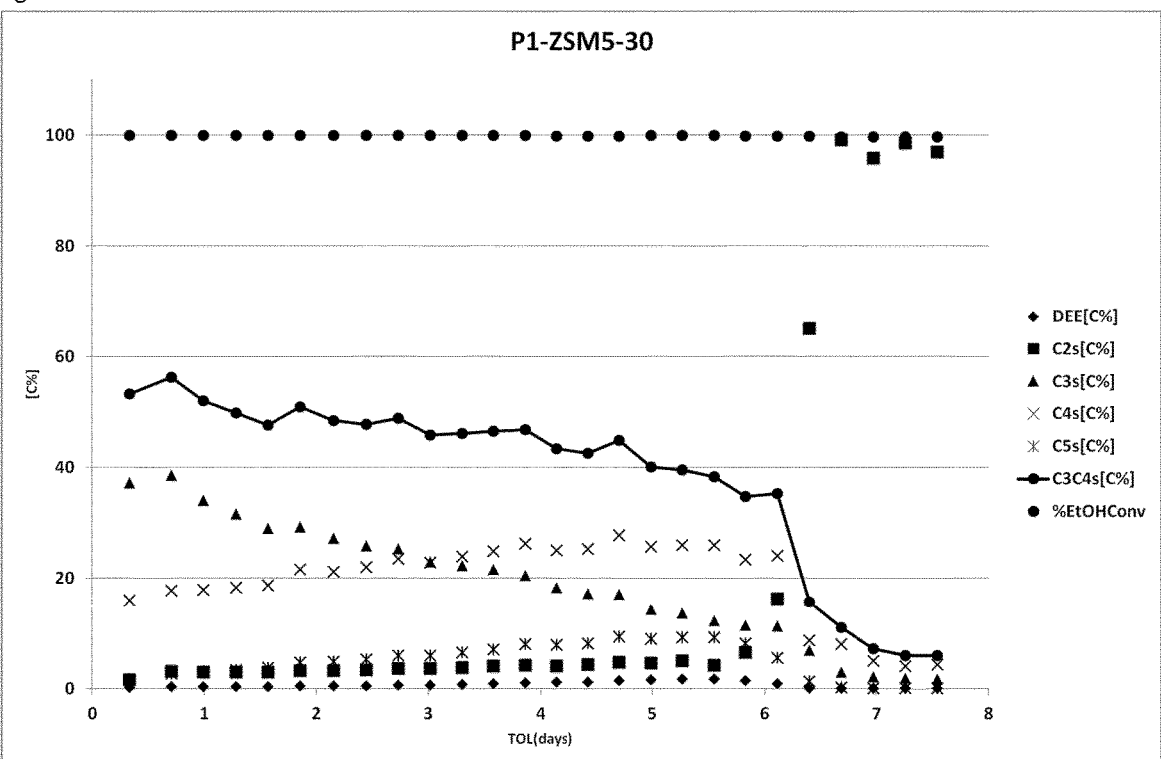
FIG. 18 shows the product selectivity of a process of the invention conducted using a phosphorus promoted ZSM5 zeolite catalyst.

FIG. 18 compares the C3 and C4 selectivity of ZSM5 and MCM22. The data in the graph clearly shows the superior performance of ZSM5 in terms of both C3/C4 selectivity and catalyst stability.

Example 3

In this experiment, it was decided to investigate the effects of including promoter elements in the zeolite catalysts on the catalytic activity and selectivity of the catalysts, as well as on the lifetime of the catalysts.

The catalyst chosen for modification with promoter elements was ZSM5-30 (ZSM5 with a Si/Al ratio of 30). This zeolite is commercially available from Alfa Aesar as the ammonium salt. The catalyst was modified with the promoter elements boron and phosphorus. The compounds B1/ZSM5-30 and P1/ZSM5-30 were synthesised. The number specified in the formula after the promoter element (for example, B1) denotes the weight percentage at which the promoter element is included in the compound.

The compounds were synthesised using methods described in the literature, such as in Wang et al., Ind. Eng. Chem. Res., 2009, 48, 10788-10795.

Firstly, the ammonium salts were converted to their H-form by calcination at 550° C. for 5 hours. The incipient wetness point (IW) of the H-ZSM5(30) was measured at 0.852 g/g with water.

Synthesis of B1/ZSM5-30

Boric acid (0.29 g) was dissolved in 4 mL of deionised water (IW quantity) and warmed to 25° C. to ensure complete dissolution. This was added dropwise to H-ZSM5 (30) with agitation, after complete addition of the solution the material was at the IW point, the material was left at room temperature for 1 hour then dried at 120° C. in air overnight followed by calcination at 550° C. for 4 hours.

Synthesis of P1/ZSM5-30

Ammonium Phosphate dibasic (0.206 g) was dissolved in 4 mL of deionised water (incipient wetness, IW quantity) and added to the H-ZSM5 (30) slowly with agitation until all the liquid had been adsorbed and a paste was obtained. The material was left at room temperature for 1 hour then dried at 120° C. in air overnight followed by calcination at 550° C. for 4 hours.

Testing of Catalytic Activity of Modified Zeolites

The catalytic activity of the boron and phosphorus modified ZSM5-30 catalysts was tested. The catalytic activity of unpromoted ZSM5-30 was tested, along with the catalytic activity of an unpromoted ZSM5-80 (Si/Al ratio=80) catalyst.

150 mg of each catalyst was mixed with 150 mg of silicon carbide, before being loaded into reaction vessel tubes.

After loading into the reaction vessel tubes, the tubes were heated under air flow to 475° C., and held for 3 hours. The tubes were cooled to 400° C. whilst purging with Argon and the reaction pressure set at 5 bar. Ethanol was then introduced to each reaction vessel at a rate of 2.0 μL/min at a temperature of 400° C. Argon was introduced at a rate of 0.625 ml/min per reaction vessel tube as the internal standard and nitrogen was introduced to each catalyst bed in each reaction vessel at a rate of 37.5 ml/min per reaction vessel tube as a diluent gas. These reaction conditions were maintained for the duration of the experiment. The purpose of the nitrogen diluent gas is simply to increase the space velocity for subsequent gas chromatography analysis.

Figure 19:
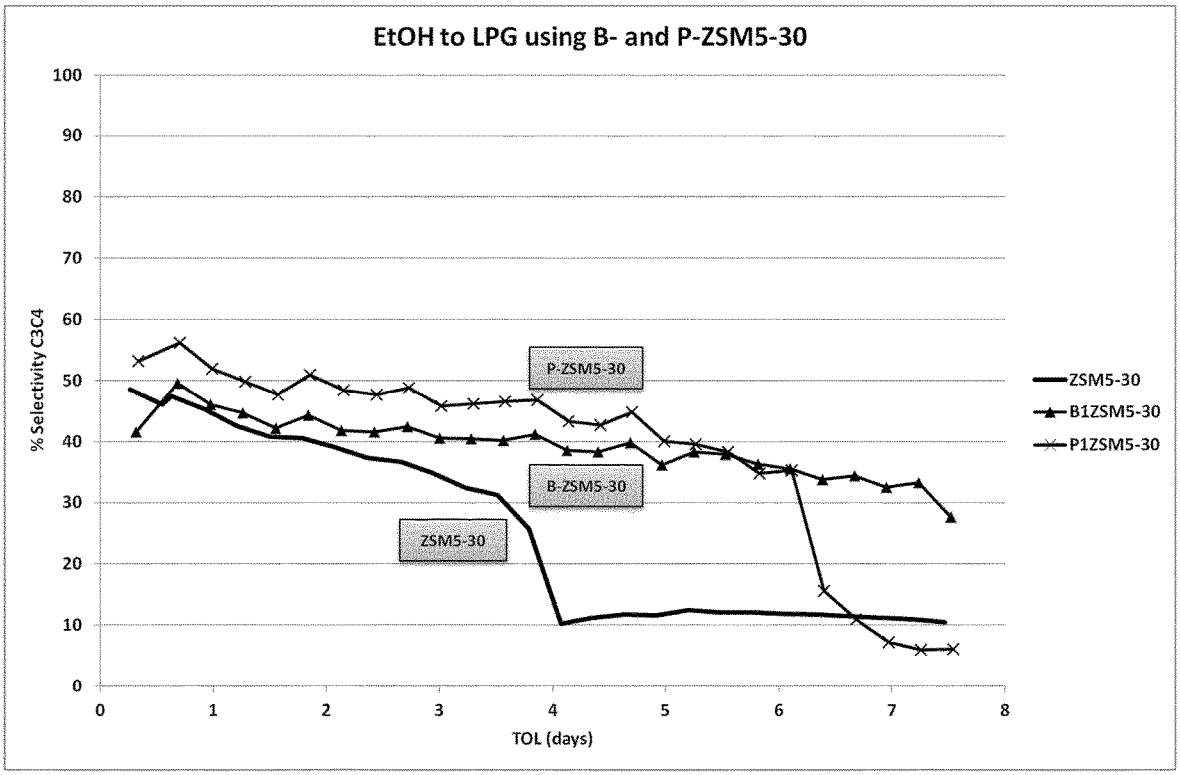
FIG. 19 contrasts the processes shown in FIGS. 17 and 18.
Figure 20:
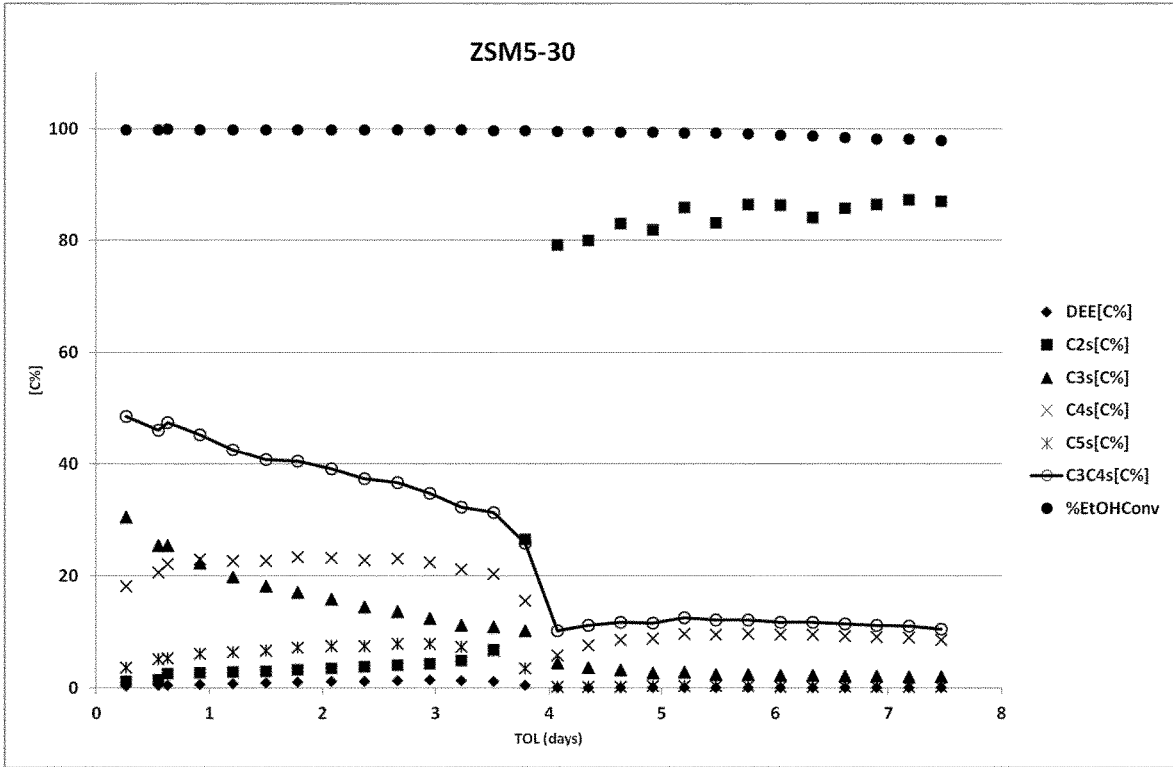
FIG. 20 shows the product selectivity of a process of the invention conducted using a ZSM5-30 catalyst.
Figure 21:
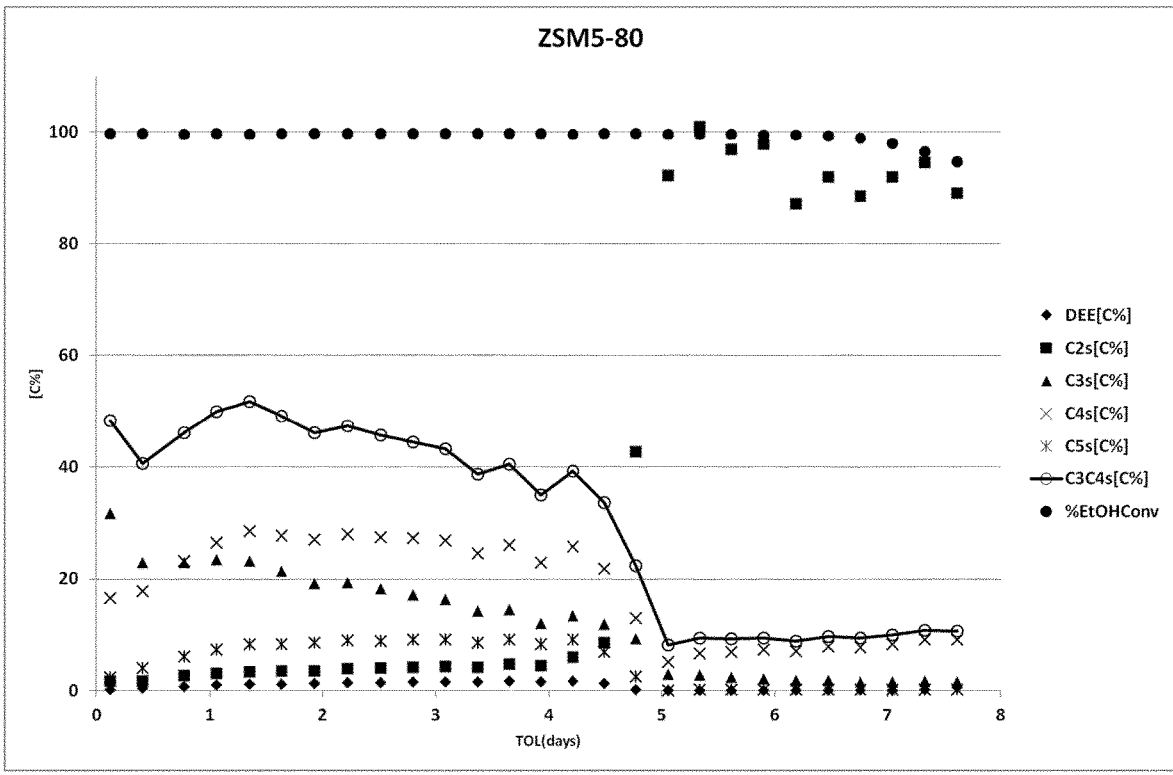
FIG. 21 shows the product selectivity of a process of the invention conducted using a ZSM5-80 catalyst.
Figure 22:
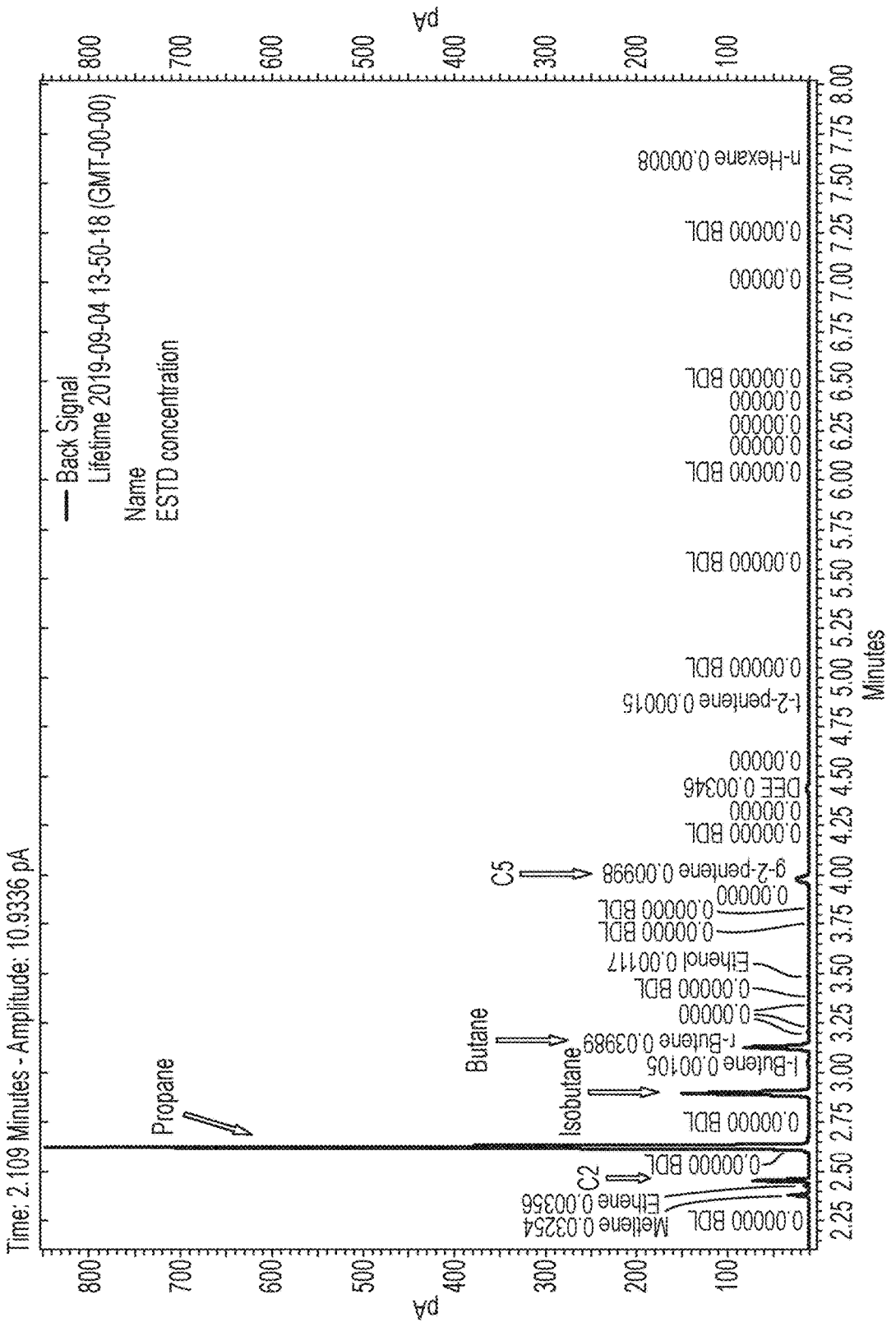
FIG. 22 shows the gas chromatography spectrum of the products of a process of the invention performed with a phosphorus promoted ZSM5-30 catalyst.
Figure 23:
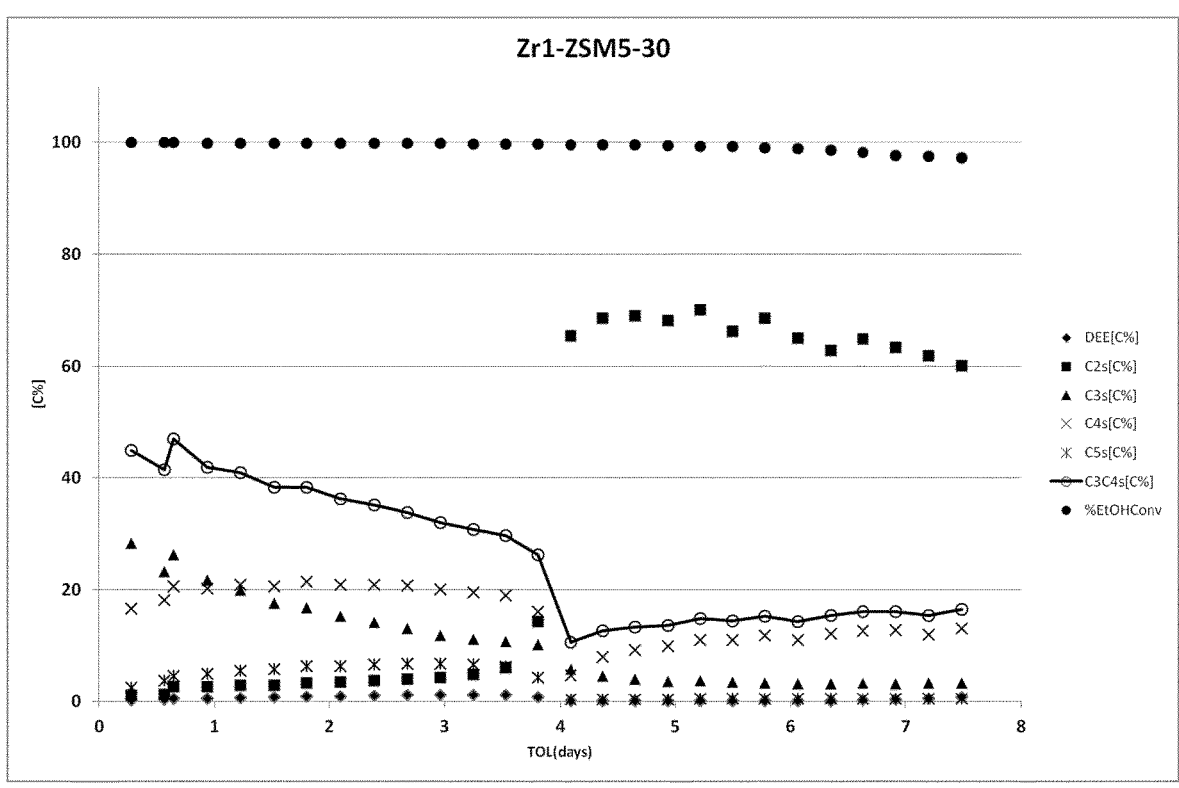
FIG. 23 shows the product selectivity of a process for converting ethanol into hydrocarbons using a zirconium promoted ZSM5-30 catalyst.
Figure 24:
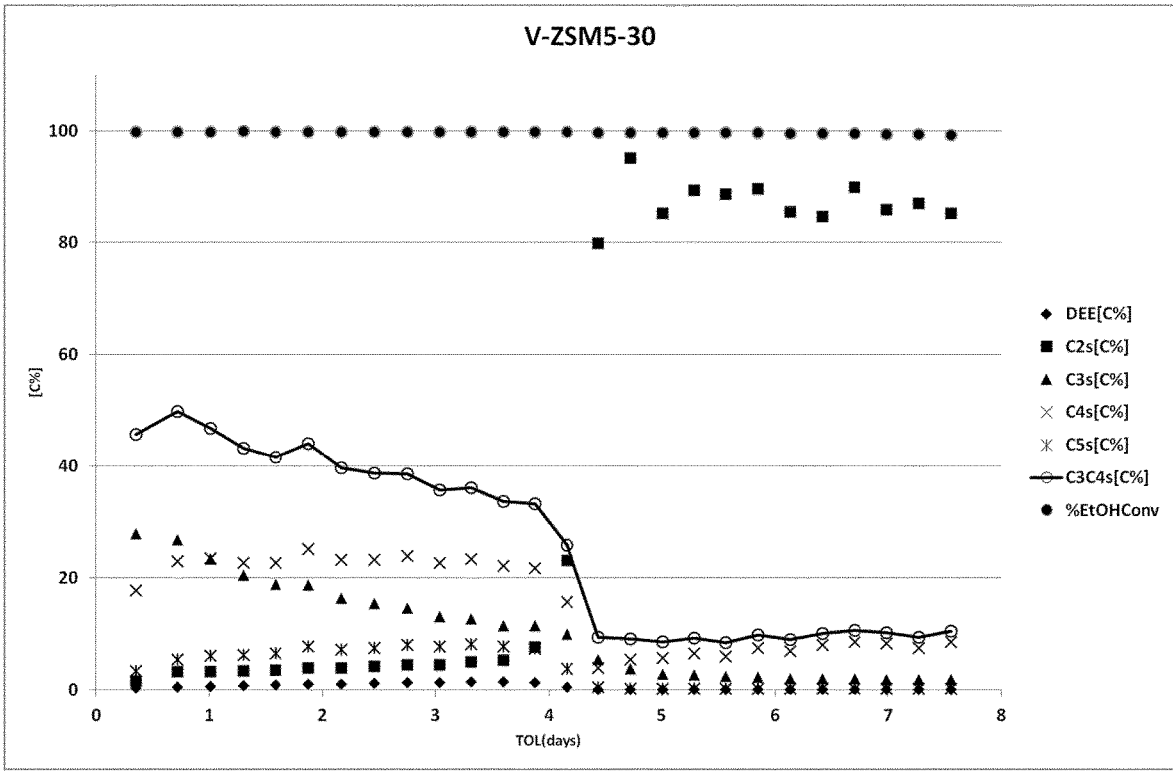
FIG. 24 shows the product selectivity of a process for converting ethanol into hydrocarbons using a vanadium promoted ZSM5-30 catalyst.

The results of the experiment for the boron and phosphorus promoted catalysts are shown in FIGS. 19 and 20. FIG. 21 shows a comparison of the results of unpromoted ZSM5-30 with those of B1/ZSM5-30 and P1/ZSM5-30. It can be seen in FIG. 21 that both the promoted catalysts B1/ZSM5-30 and P1/ZSM5-30 had higher selectivity for C3 and C4 hydrocarbons than the unpromoted ZSM5-30 material. Additionally, both promoted catalysts had longer catalyst lifetimes than the corresponding unpromoted material. Whilst the initial selectivity of the phosphorus promoted catalyst was higher than the boron promoted catalyst, the extension of the lifetime of the boron promoted catalyst was greater. The lifetime extension of the catalyst is very significant in zeolite chemistry, and significantly improves the efficiency of the process. FIGS. 22 and 23 show the results of unpromoted HZSM5-30 and HZSM5-80. The HZSM5-80 catalyst has increased C3/C4 hydrocarbon selectivity, and also longer catalyst lifetime (shown by decreasing C3/C4 selectivity and increased C2 hydrocarbon production). FIG. 24 shows the gas chromatography spectrum of the products after 3 hours online for the P1/ZSM5-30 catalyst. It can be seen that C3 and C4 hydrocarbon compounds dominate the product spectrum with large peaks corresponding to propane, butane and isobutene.

Ammonia Programmed Desorption Spectra

Ammonia temperature programmed desorption ($NH_3$-TPD) experiments were carried out on the zeolites to determine how the introduction of promoter elements into the zeolites affected their acidity properties.

Experimental Protocol

NH3-TPD experiments were carried out in a Micromeritics 2920, which is equipped with a TCD detector coupled to a Pfeiffer ThermoStar quadrupole mass spectrometer which allows the analysis and monitoring of gaseous products as a function of time or sample temperature.

Around 80 mg of sample was loaded into the U-shaped tube and attached to the instrument. The sample was dried under a flow of argon in a two-step process, at 120° C. for 30 min and 500° C. for 20 min. Then, the sample is cooled down to 100° C. and saturated with NH3 by flowing 5% NH3/He for 1 h at this temperature, followed by an evacuation step lasting 1 h. The sample is then heated up to 500° C. to desorb NH3, with both TCD and MS monitoring the effluent gas during the desorption step.

The ions m/z 18, 17 and 14 were followed to monitor $H2O^+$, $OH^+$ and $NH3^+$ and N+ ions profiles.

The data in Table 4 shows the total ammonia desorption values for the zeolites. The lower the total ammonia desorption value, the lower the acid site density of the zeolite. The acid site density is correlated to the total acidity of the zeolite (although it is not the sole determinant thereof). It can be seen that both the boron and phosphorus promoted zeolites both exhibited reduced acid site density compared to the unpromoted zeolite catalyst. This reduced acid site density is indicated by the lower values for total ammonia desorption. An analysis of the TPD spectrum of the zeolites also showed that the acid site distribution had shifted in the promoted zeolites such that the promoted zeolites had a higher ratio of weak acid sites to strong acid sites than the corresponding unpromoted zeolite material. This finding, in combination with the reduced acid site density, concludes that the promoted zeolite materials had a reduced acidity compared to the corresponding unpromoted zeolite material.

TABLE 4

| Sample | Desorption lower temperature m/z17 Norm. Area (×10−10) | Desorption higher temperature m/z17 Norm. Area (×10−10) | Total Desorption m/z Norm. Area (×10−10) |
|---|---|---|---|
| H-ZSM5-30 | 2.59 | 2.05 | 4.64 |
| B1ZSM5-30 | — | — | 4.24 |
| P1ZSM5-30 | 2.10 | 1.46 | 3.56 |

It is believed by the inventors of the present invention that the increased selectivity of the promoted catalysts for C3 and C4 hydrocarbons is due, at least in part, to the reduced acidity of the promoted zeolite catalysts compared to the baseline corresponding unpromoted catalyst materials. To further investigate this, analysis of the porosity and pore structure of the catalysts was undertaken, and is described in further detail below.

Porosity Measurements

The porosity of all zeolite catalyst samples was measured on a Micromeritics Gemini VI instrument. With the surface area being calculated using the Brunauer, Emmett and Teller (BET) transformation. The Pore volume and area distribution are calculated using the Barret, Joyner and Helnda (BJH) method. The measurements are shown in Table 5 below. All samples show a very similar isotherm typical of ZSM5 zeolites with a hysteresis loop confirming type-IV behaviour. A number of features can be observed from the data collected. The ZSM5(80) has a higher surface area than the ZSM5(30) which is consistent with the manufacturers data and upon calcination of $NH_4$-ZSM5(30) and removal of the ammonium counteranion the surface area is increased as would be expected.

TABLE 5

| Sample | BET Surface Area (m2/g) | Pore Volume (cm3/g) | Pore Size (Angstroms) |
|---|---|---|---|
| $NH_4$ ZSM5-80 | 516 | 0.30 | 34 |
| $NH_4$ ZSM5-30 | 370 | 0.22 | 39 |
| H ZSM5-30 | 393 | 0.24 | 35 |
| B1 ZSM5-30 | 332 | 0.21 | 42 |
| P1 ZSM5-30 | 312 | 0.19 | 36 |

The addition of modifiers to the zeolites resulted in the surface area and pore volumes dropping slightly, however there are no large changes indicating that there is no pore blocking or significant structural changes in the material caused by the reaction conditions or ion exchange of the ammonium. This is also confirmed by the consistent nature of the isotherm for all samples showing the same underlying structure upon modification.

Without being limited by theory, the lack of significant change in pore structure of the zeolite catalysts upon promotion indicates it is likely that the changes in catalytic performance are primarily due to the reduction of the acid strength of the catalysts, as opposed to surface or structural properties of the catalyst.

Figure 25:
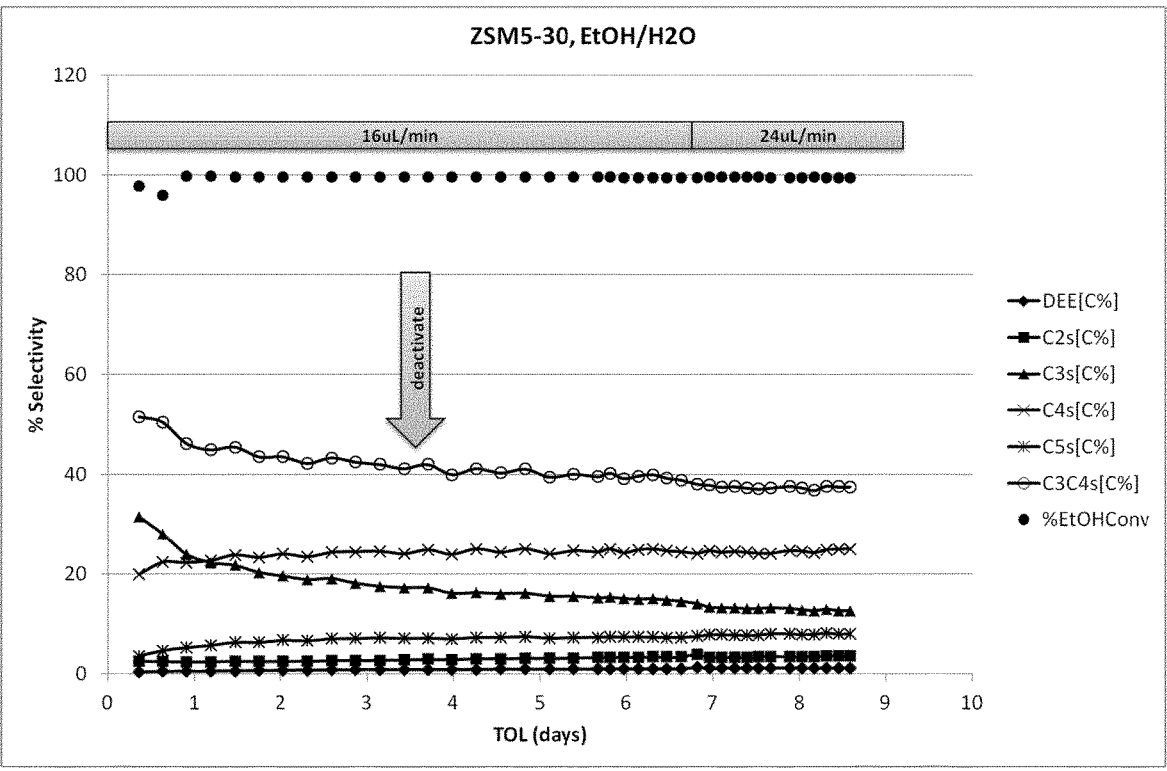
FIGS. 25 to 28 show the product selectivities of catalysts of the invention in processes of the invention where the feedstream comprises a mixture of water and ethanol.
Figure 26:
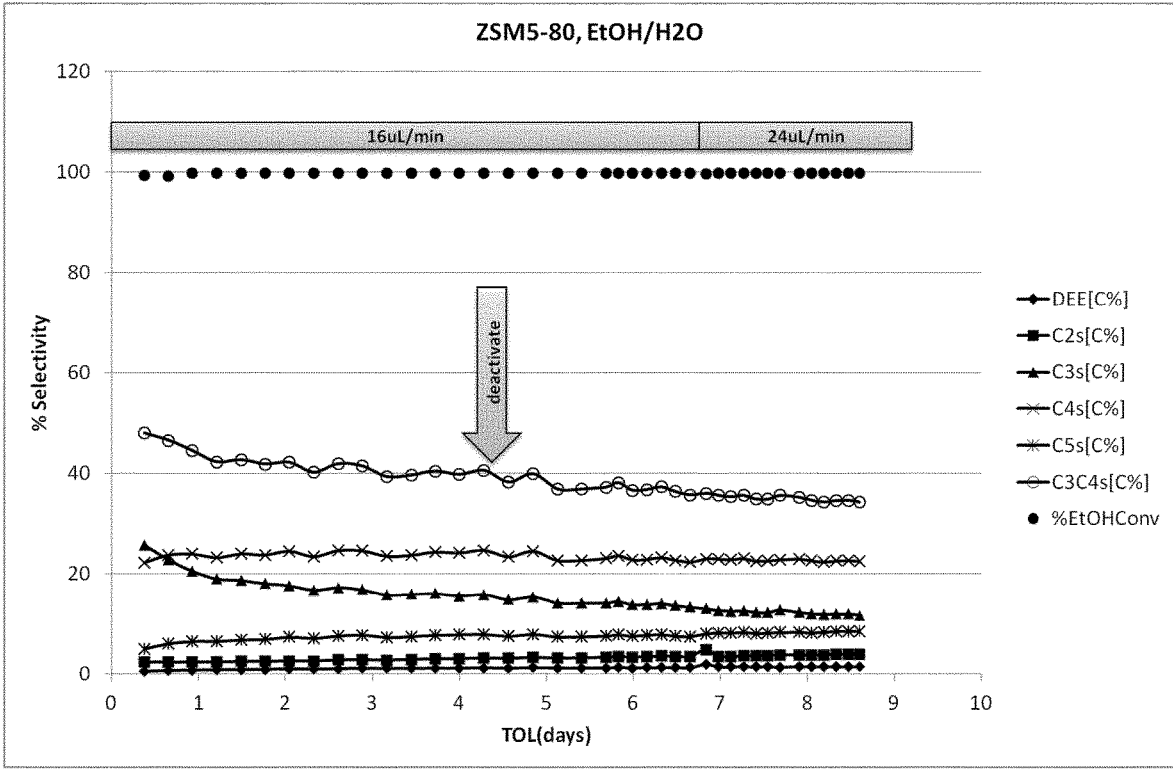
Figure 27:
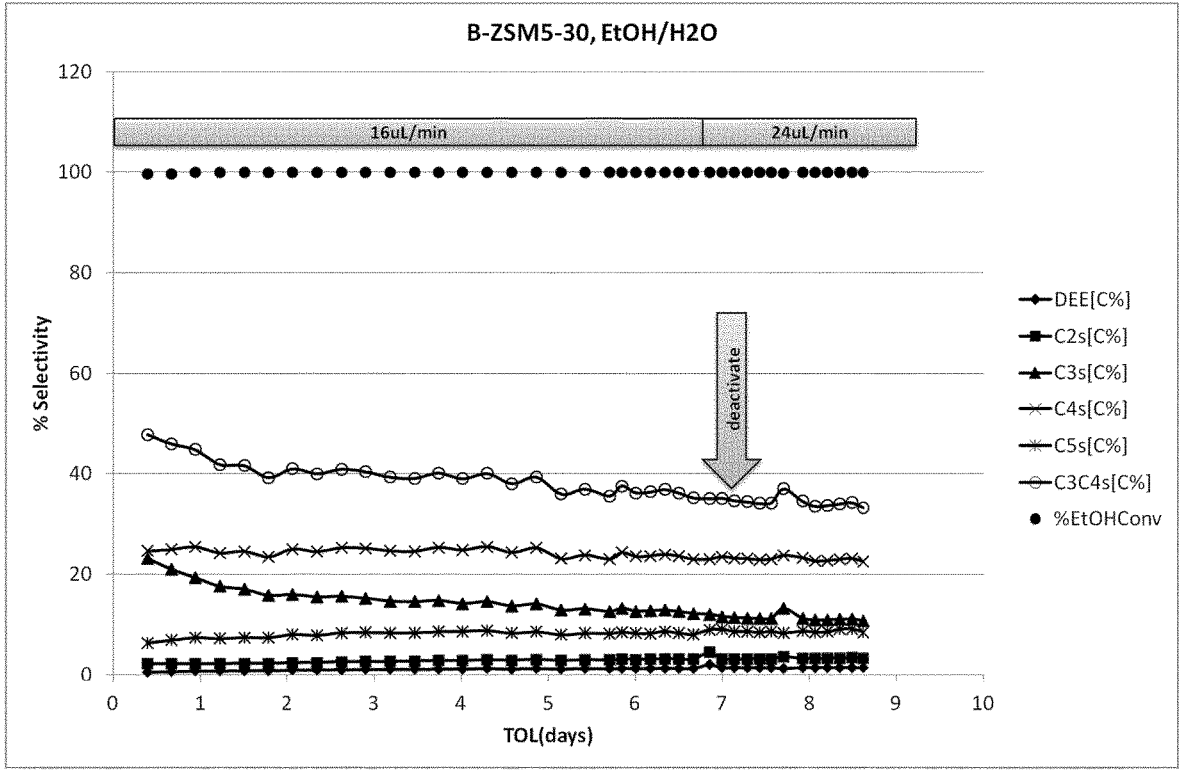
Figure 28:
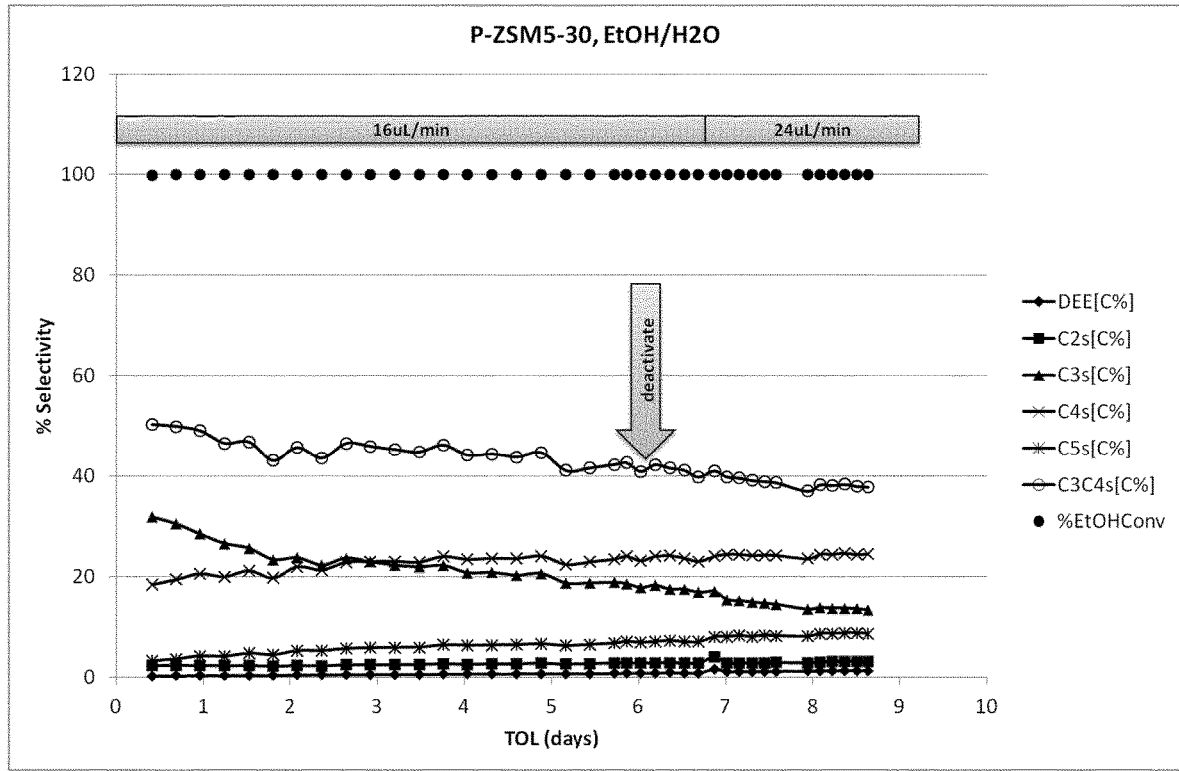
Figure 29:
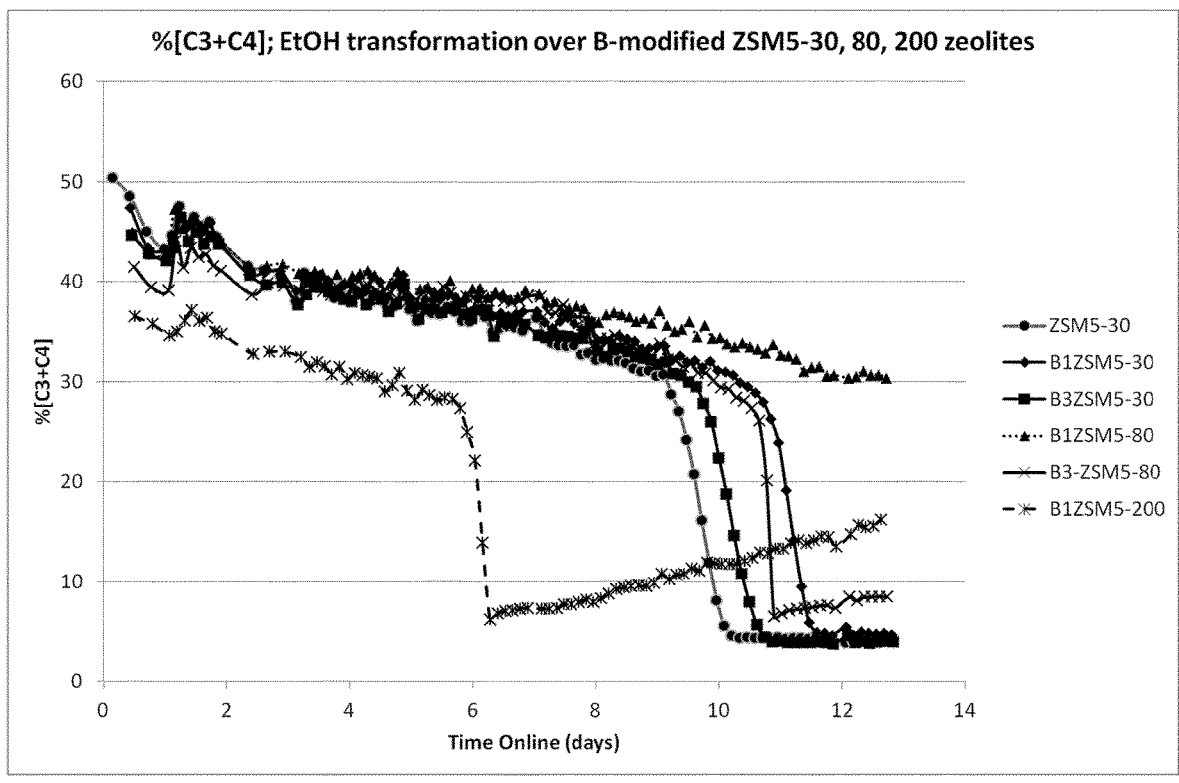
FIGS. 29 to 35 show the product selectivities of various phosphorus and boron promoted catalysts of the invention when used in various processes of the invention.
Figure 30:
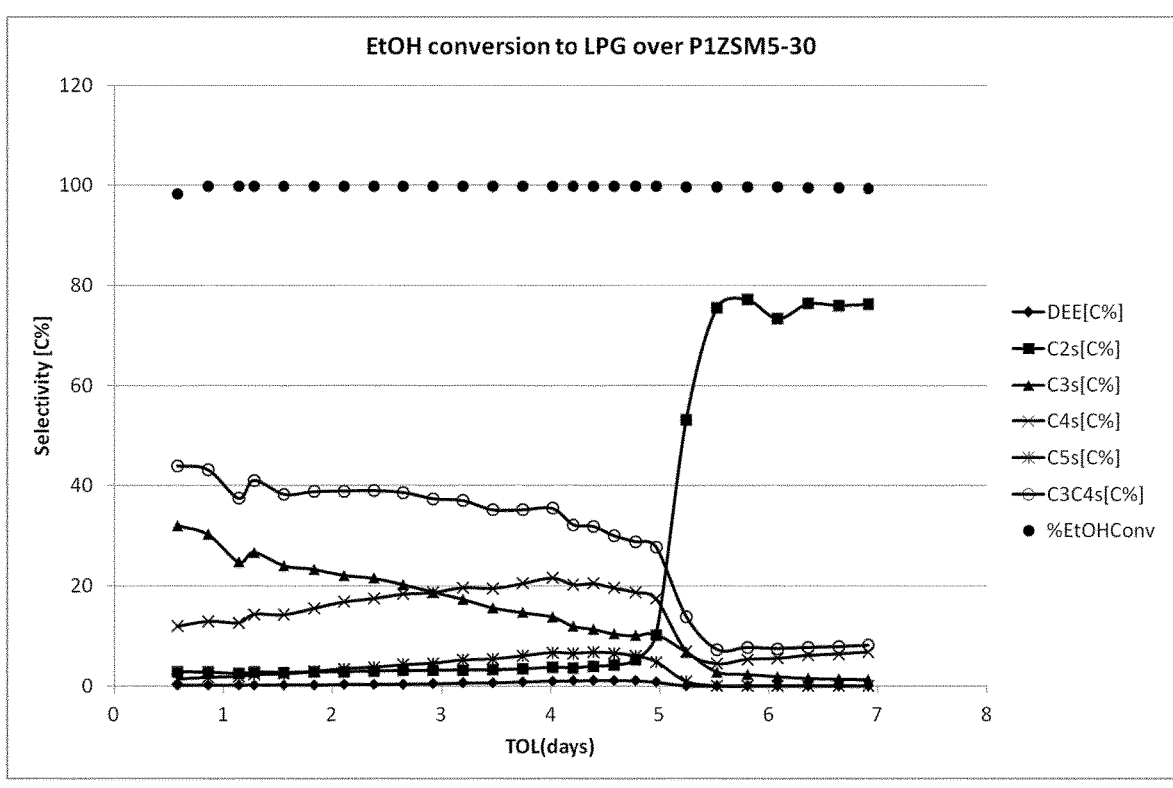

To further investigate the effect of reducing the acidity of the zeolite catalysts, the promoted zeolite catalysts Zr1 ZSM5-30 and V ZSM5-30 were synthesised (ZSM5 promoted with 1 weight % zirconium and vanadium respectively). The total desorption (m/z 17 Norm. Area (×10-10) of these catalysts was 4.72 and 5.69 respectively. The catalysts thus had a higher acid site density than the corresponding unpromoted zeolite catalyst which had a total desorption of 4.64 as shown above in Table 4. These catalysts did not show the improved C3/C4 hydrocarbon selectivity or improved catalyst lifetime associated with the boron and phosphorus promoted catalysts, as can be seen from a comparison of FIGS. 25 and 26 with FIGS. 22, 23 and 24.

Example 4

Example 4 was undertaken to investigate the effect on the process of using an ethanol feedstream with water vapour present therein. The feedstream used comprised around 12% water and around 88% ethanol.

The catalysts shown in Table 6 were tested.

TABLE 6

| Sample | Catalysts | Mass (mg) | SiC (mg) |
|---|---|---|---|
| 1 | Blank ethanol/$H_2O$ | 0 | 500 |
| 2 | ZSM5-30 | 150 | 150 |
| 3 | ZSM5-80 | 150 | 150 |
| 4 | B1/ZSM5-30 | 150 | 150 |
| 5 | P1/ZSM5-30 | 150 | 150 |

Reaction Conditions

Each catalyst was placed in a separate reaction vessel. After loading the each reaction vessel with catalyst, the reaction vessels were heated under air flow to 475° C. and held for 3 hours. The reaction vessels were cooled to 400° C. whilst purging with Argon and the reaction pressure set at 5 bar. An ethanol/water mixture (~88:12) (2.0 µL/min/ reaction vessel) was introduced at 400° C. and Argon (8 ml/min) was used as internal standard.

The results of these experiments are shown in FIGS. 27 to 30. The arrows displayed in these graphs indicate the time period after which the catalysts start deactivating when anhydrous ethanol is used. It can be seen from the graphs that none of the catalysts deactivate in the time period tested when 12% water is included in the feedstream, and that catalyst lifetime far exceeds that when anhydrous ethanol is used as the feedstream. When the process was stopped after nine days online, not one of the catalysts showed deactivation. The phosphorus promoted catalyst showed notably better C3 and C3/C4 selectivity when compared to the corresponding unpromoted zeolite material.

Example 5

A further study was undertaken to investigate the effects of including different levels of promoter elements in the zeolites.

The following catalysts were synthesised for testing: B1/ZSM5-30; B3/ZSM5-30; B1/ZSM5-80; B3/ZSM5-80;

P1/ZSM5-30; P3/ZSM5-30; P1/ZSM5-80; and P3/ZSM5-80; P1/ZSM5-200; P2/ZSM5-30; P2/ZSM5-80; B1/ZSM5-200 and P1/ZSM5-200.

The Si/Al ratio of ZSM5-30, ZSM5-80 and ZSM5-200 is 30, 80 and 200 respectively.

The number specified in the formula after the promoter element corresponds to the weight percentage of the promoter element in the zeolite material.

Synthesis of Zeolites

The ZSM5 zeolites were obtained from Alfa Aesar.

The compounds were synthesised using methods described in the literature, such as in Wang et al., Ind. Eng. Chem. Res., 2009, 48, 10788-10795.

The zeolites used in the following procedures were in the protonated rather than the ammonium form, i.e. H-ZSM-5 and not NH4-ZSM-5. H-ZSM-5 materials were prepared by air calcination of the parent NH4-ZSM-5 zeolite at 550° C. for 5 hours. The incipient wetness points (IW) for the materials were measured in order that the incipient wetness impregnations can be carried out effectively.

Boron Promoted Zeolites

Modification with Boron is carried out using Boric acid which has a limited solubility of 5.7 g/100 mL. This required the 3% B to be prepared by multiple impregnations as opposed to a single impregnation.

B1/ZSM5-30

| H-ZSM5(30) | 5 g |
|---|---|
| H3BO3 | 290 mg |

Boric acid (0.29 g) was dissolved in 4 mL of deionised water (IW quantity) and warmed to 25° C. to ensure complete dissolution. This was added dropwise to H-ZSM5 (30) with agitation, after complete addition of the solution the material was at the IW point, the material was left at room temperature for 1 hour then dried at 120° C. in air overnight followed by calcination at 550° C. for 4 hours.

B3/ZSM5-30

| B1/ZSM5-30 | 2.5 g |
|---|---|
| H3BO3 | 145 mg |

Boric acid (0.145 g) was dissolved in 2 mL of deionised water (IW quantity) and warmed to 25° C. to ensure complete dissolution. This was added dropwise to the 1% boron promoted catalyst with manual mixing followed by drying in the fume cupboard, dried at 120° C. in air overnight followed by calcination at 550° C. for 4 hours. This calcined material was then subjected to the same procedure of Boron addition drying and calcination to produce the 3% boron on H-ZSM-5 (30).

B1/ZSM5-80

| H-ZSM5(80) | 5 g |
|---|---|
| H3BO3 | 290 mg |

Boric acid (0.29 g) was dissolved in 4 mL of deionised water (IW quantity) and warmed to 25° C. to ensure complete dissolution. This was added dropwise to H-ZSM5 (80) with agitation, after complete addition of the solution the material was at the IW point, the material was left at room temperature for 1 hour then dried at 120° C. in air overnight followed by calcination at 550° C. for 4 hours.
B3/ZSM5-80

| B1/ZSM5-30 | 2.5 g |
|---|---|
| H3BO3 | 145 mg |

Boric acid (0.145 g) was dissolved in 1 mL of deionised water (IW quantity) and warmed to 25° C. to ensure complete dissolution. This was added dropwise to the 1 weight % boron promoted catalyst with manual mixing followed by drying in the fume cupboard, dried at 120° C. in air overnight followed by calcination at 550° C. for 4 hours. This calcined material was then subjected to the same procedure of Boron addition drying and calcination to produce the 3% boron on H-ZSM-5 (80).
B1/ZSM5-200

Due to the limited pore volume of ZSM5-200 and the low solubility of boric acid the 1 wt % boron on ZSM5-200 was achieved by a double impregnation.

| ZSM5-200 | 2.5 g |
|---|---|
| H3BO3 | 73 mg |

Boric acid (0.073 g) was dissolved in 1 mL of deionised water (IW quantity) and warmed to 25° C. to ensure complete dissolution. This was added dropwise to ZSM5-200 with agitation, after complete addition of the solution the material was at the IW point, the material was left at room temperature for 1 hour then dried at 120° C. in air overnight followed by calcination at 550° C. for 4 hours. This calcined material was then subjected to the same procedure of Boron addition drying and calcination to produce the 1% boron on ZSM5-200.

Phosphorus Promoted Zeolites

Ammonium dihydrogen phosphate was used to modify the zeolites in this section, as the solubility of this material is 40 g/L at 25° C. the 3 wt % materials were produced in a single impregnation.
P1/ZSM5-30

| H-ZSM5-30 | 5 g |
|---|---|
| (NH4)H2PO4 | 179 mg |

Ammonium dihydrogen phosphate (0.179 g) was dissolved in 3 mL of deionised water (IW quantity) and warmed to 25° C. to ensure complete dissolution. This was added dropwise to ZSM5-30 with agitation, after complete addition of the solution the material was at the IW point, the material was left at room temperature for 1 hour then dried at 120° C. in air overnight followed by calcination at 550° C. for 4 hours.
P3/ZSM5-30

| H-ZSM5-30 | 5 g |
|---|---|
| (NH$_4$)H$_2$PO$_4$ | 555 mg |

Ammonium dihydrogen phosphate (0.555 g) was dissolved in 3 mL of deionised water (IW quantity) and warmed to 25° C. to ensure complete dissolution. This was added dropwise to ZSM5-30 with agitation, after complete addition of the solution the material was at the IW point, the material was left at room temperature for 1 hour then dried at 120° C. in air overnight followed by calcination at 550° C. for 4 hours.
P1/ZSM5-80

| H-ZSM5-80 | 5 g |
|---|---|
| (NH4)H2PO4 | 179 mg |

Ammonium dihydrogen phosphate (0.179 g) was dissolved in 3 mL of deionised water (IW quantity) and warmed to 25° C. to ensure complete dissolution. This was added dropwise to ZSM5-80 with agitation, after complete addition of the solution the material was at the IW point, the material was left at room temperature for 1 hour then dried at 120° C. in air overnight followed by calcination at 550° C. for 4 hours.
P3/ZSM5-80

| H-ZSM5-80 | 5 g |
|---|---|
| (NH$_4$)H$_2$PO$_4$ | 555 mg |

Ammonium dihydrogen phosphate (0.555 g) was dissolved in 3 mL of deionised water (IW quantity) and warmed to 25° C. to ensure complete dissolution. This was added dropwise to ZSM5-80 with agitation, after complete addition of the solution the material was at the IW point, the material was left at room temperature for 1 hour then dried at 120° C. in air overnight followed by calcination at 550° C. for 4 hours.
P1/ZSM5-200

| H-ZSM5-200 | 5 g |
|---|---|
| (NH$_4$)H$_2$PO$_4$ | 179 mg |

Ammonium dihydrogen phosphate (0.179 g) was dissolved in 2 mL of deionised water (IW quantity) and warmed to 25° C. to ensure complete dissolution. This was added dropwise to ZSM5-200 with agitation, after complete addition of the solution the material was at the IW point, the material was left at room temperature for 1 hour then dried at 120° C. in air overnight followed by calcination at 550° C. for 4 hours.

The following two materials in this study were prepared from Phosphoric acid (85%) and the amounts needed to yield 2 wt % P calculated from the properties of the acid.
P2/ZSM5-30

| H-ZSM5-30 | 5 g |
|---|---|
| H$_3$PO$_4$ (85%) | 0.223 mL |

Phosphoric acid (0.223 mL) was dissolved in 3 mL of deionised water (IW quantity) and warmed to 25° C. to ensure complete dissolution. This was added dropwise to ZSM5-30 with agitation, after complete addition of the solution the material was at the IW point, the material was left at room temperature for 1 hour then dried at 120° C. in air overnight followed by calcination at 550° C. for 4 hours.
P2/ZSM5-80

| H-ZSM5-30 | 5 g |
|---|---|
| H$_3$PO$_4$ (85%) | 0.223 mL |

Phosphoric acid (0.223 mL) was dissolved in 3 mL of deionised water (IW quantity) and warmed to 25° C. to ensure complete dissolution. This was added dropwise to ZSM5-30 with agitation, after complete addition of the solution the material was at the IW point, the material was left at room temperature for 1 hour then dried at 120° C. in air overnight followed by calcination at 550° C. for 4 hours.

Catalyst Testing Experiments

Certain catalysts were tested by being loaded into separate reaction vessels. Each reaction vessel comprised 150 mg of catalyst and 150 mg of silicon carbide.

Reaction Conditions

After loading into the reaction vessel tubes, the tubes were heated under air flow to 475° C., and held for 3 hours. The tubes were cooled to 400° C. whilst purging with Argon and the reaction pressure set at 5 bar. Ethanol was then introduced to each reaction vessel at a rate of 2.0 µL/min at a temperature of 400° C. Argon was introduced at a rate of 1 ml/min per reaction vessel tube as the internal standard and nitrogen was introduced to each catalyst bed in each reaction vessel at a rate of 37.5 ml/min per reaction vessel tube as a diluent gas. These reaction conditions were maintained for the duration of the experiment. The purpose of the nitrogen diluent gas is simply to increase the space velocity for subsequent gas chromatography analysis.

Figure 31:
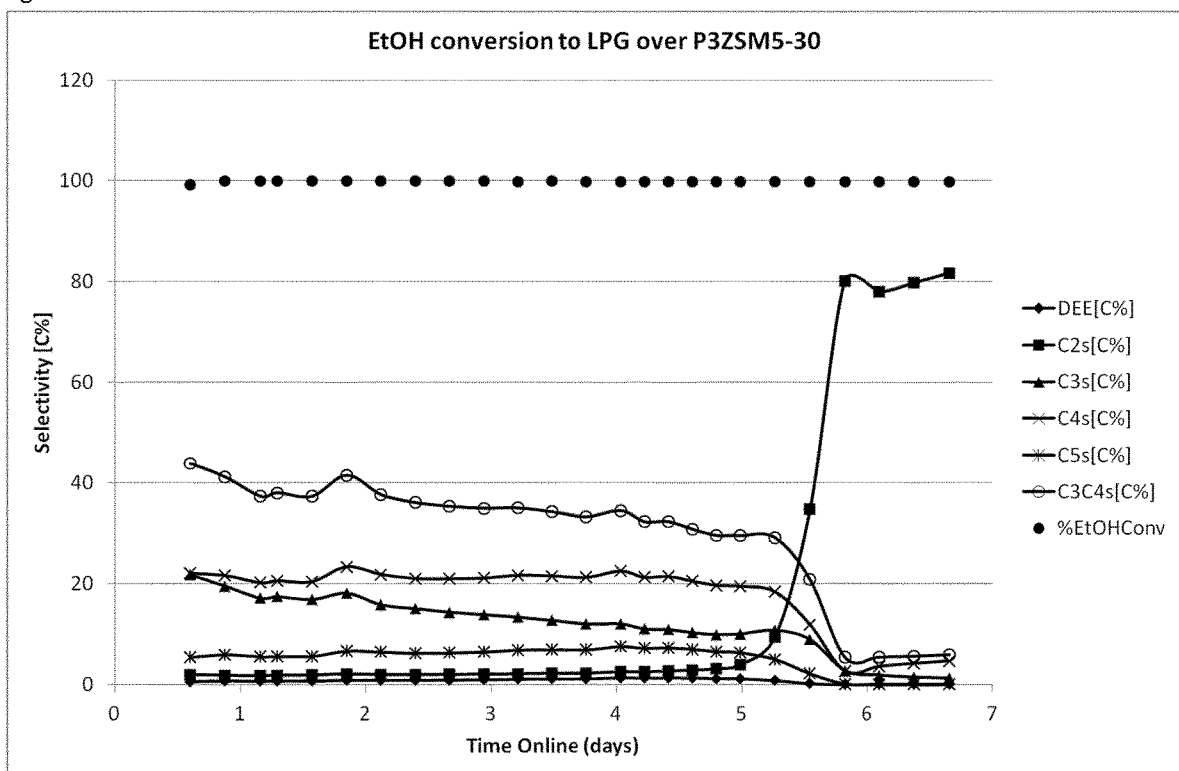
Figure 32:
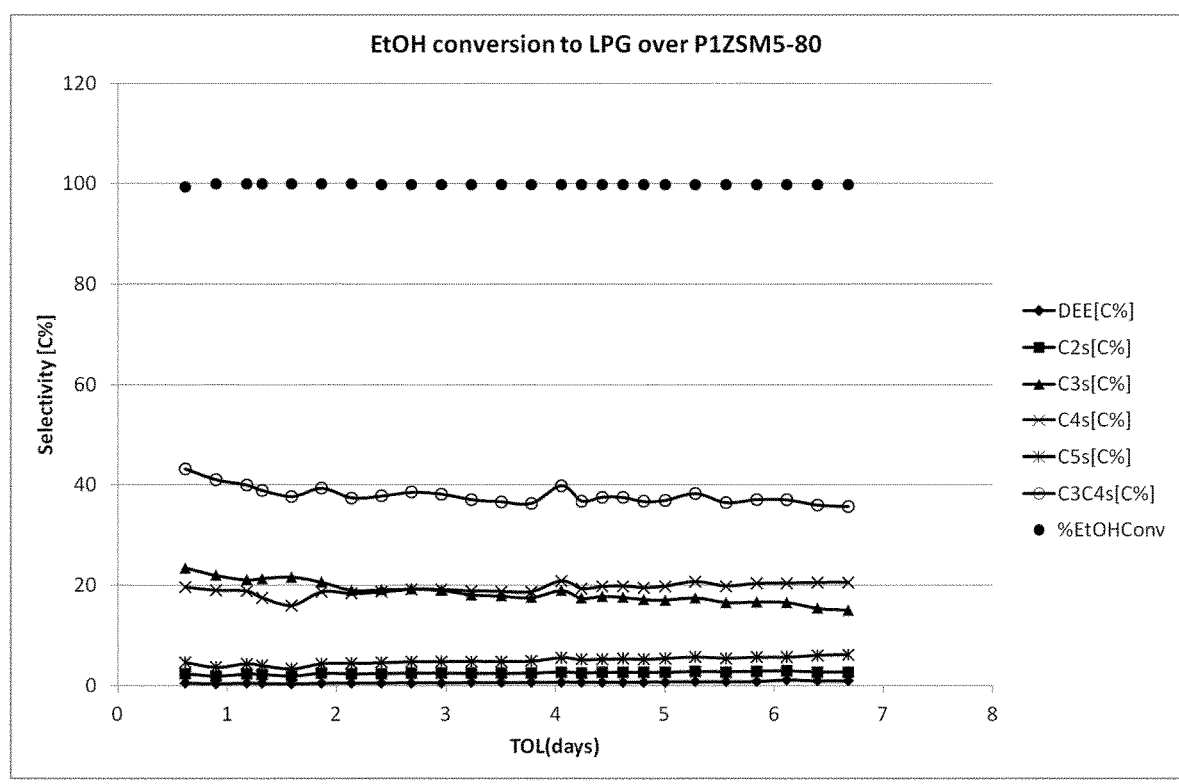
Figure 33:
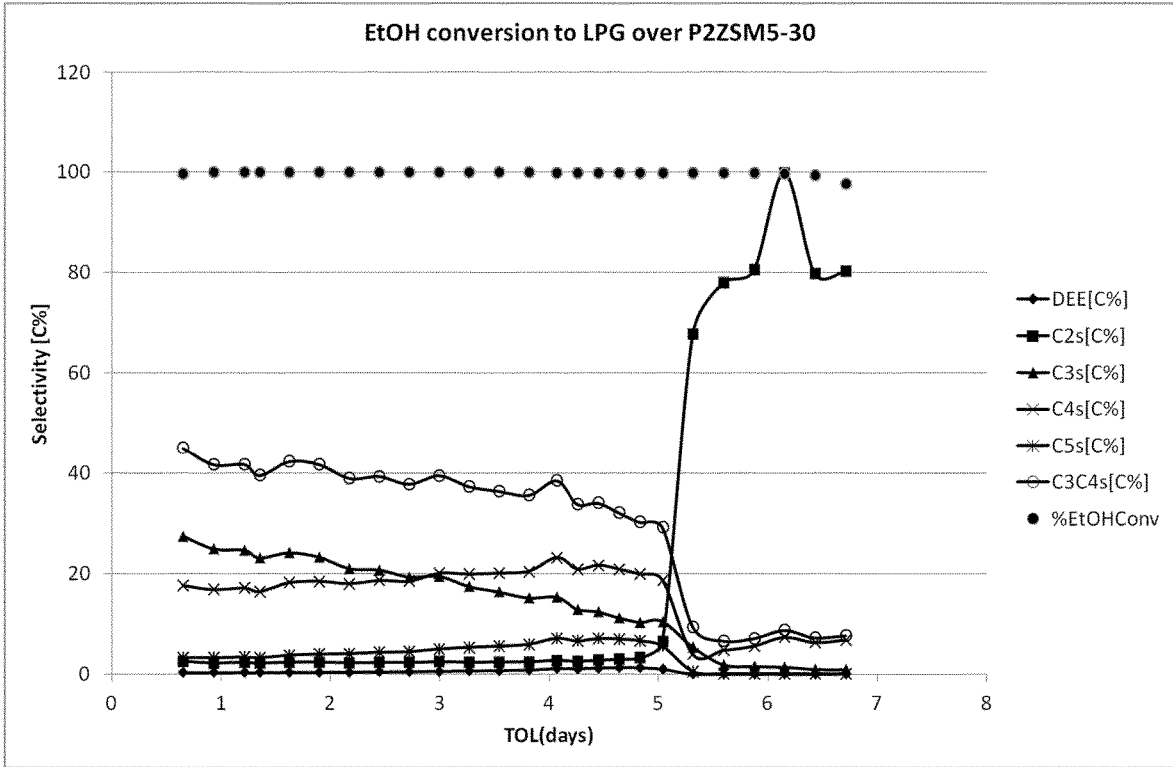
Figure 34:
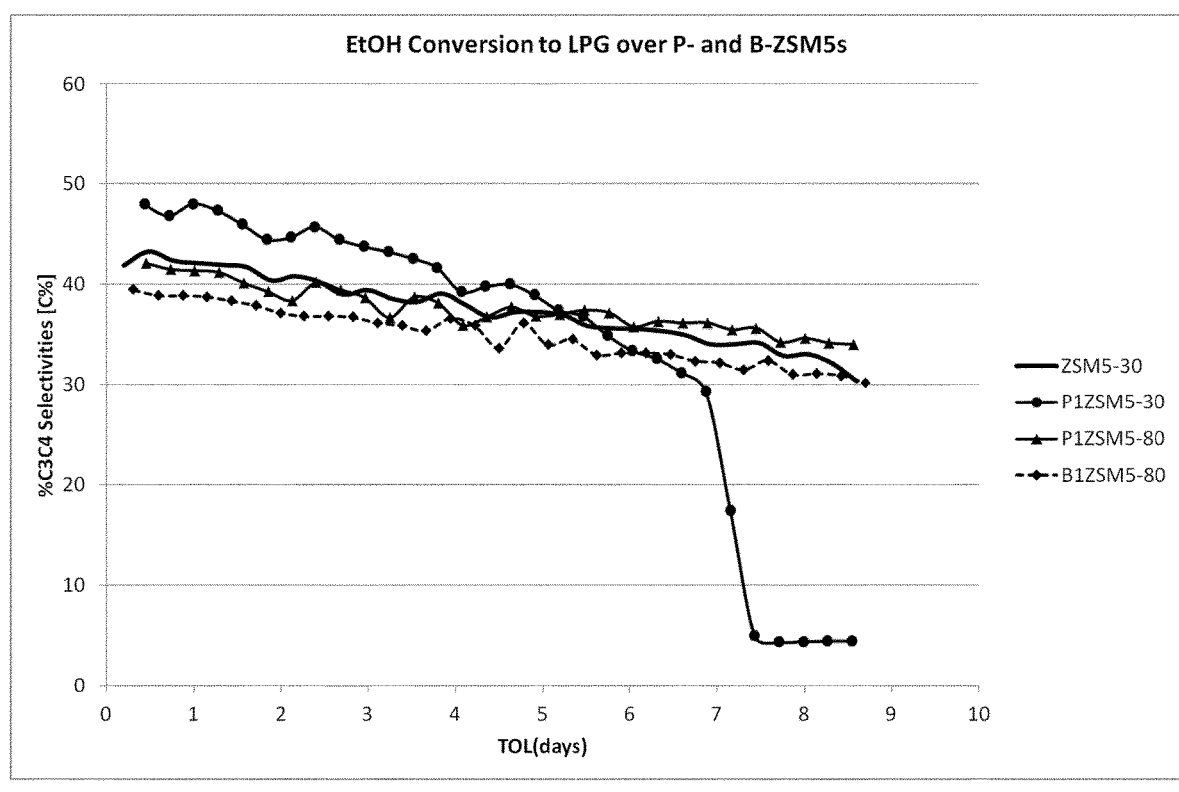
Figure 35:
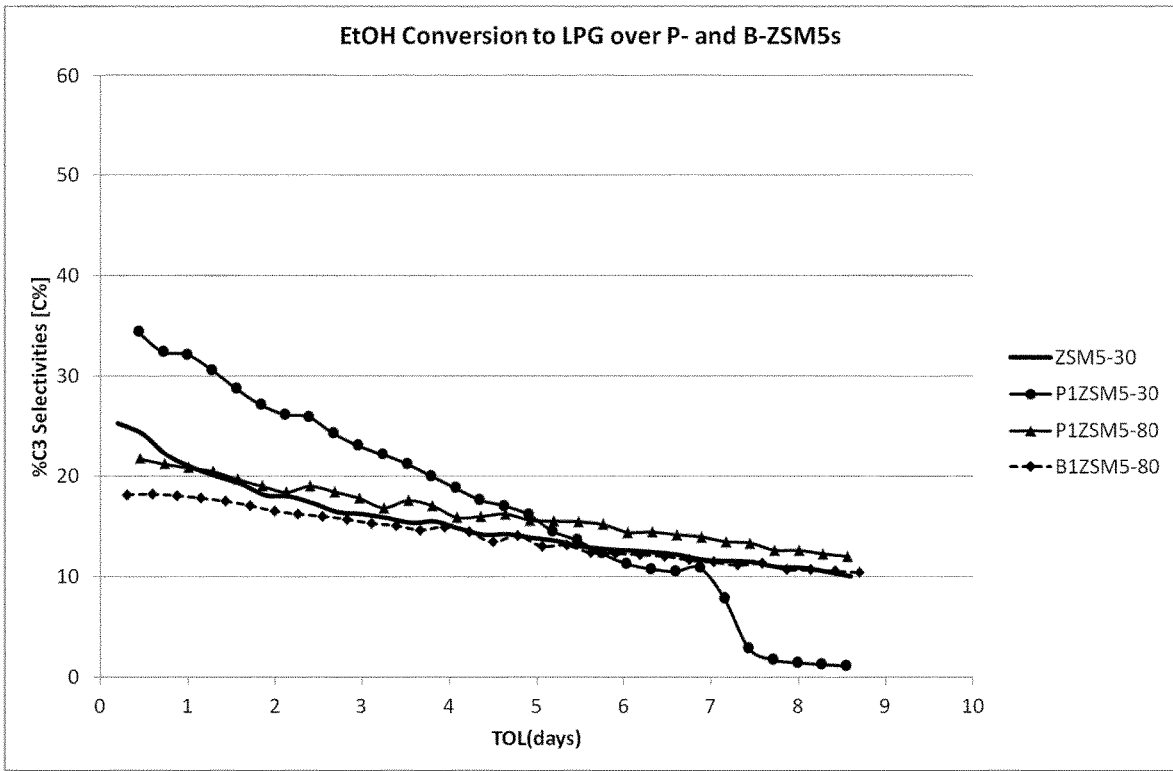

The results for the boron promoted zeolites are shown in FIG. 31. It can be seen that all boron promoted catalysts showed good initial selectivity for C3/C4 hydrocarbons. All boron promoted catalysts demonstrated increased catalyst lifetime when compared to the corresponding baseline unpromoted catalyst ZSM5-30, with the exception of the catalyst B1-ZSM5-200. All boron promoted catalysts showed similar initial selectivity for C3/C4 hydrocarbons as the unpromoted ZSM5-30 catalyst, with the exception of B1ZSM5-200.

The results for the phosphorus promoted catalysts are shown in FIGS. 32 to 35. All of these phosphorus promoted catalysts had a higher initial C3/C4 selectivity than the unpromoted ZSM5-30. All of the phosphorus promoted catalysts showed a longer catalyst lifetime compared to unpromoted zeolite ZSM5-30. The catalysts with the longest lifetimes were P3ZSM5-30 and P1ZSM5-80. In particular, P1ZSM5-80 showed no signs of deactivation after 7 days online.

Example 6

Figure 36:
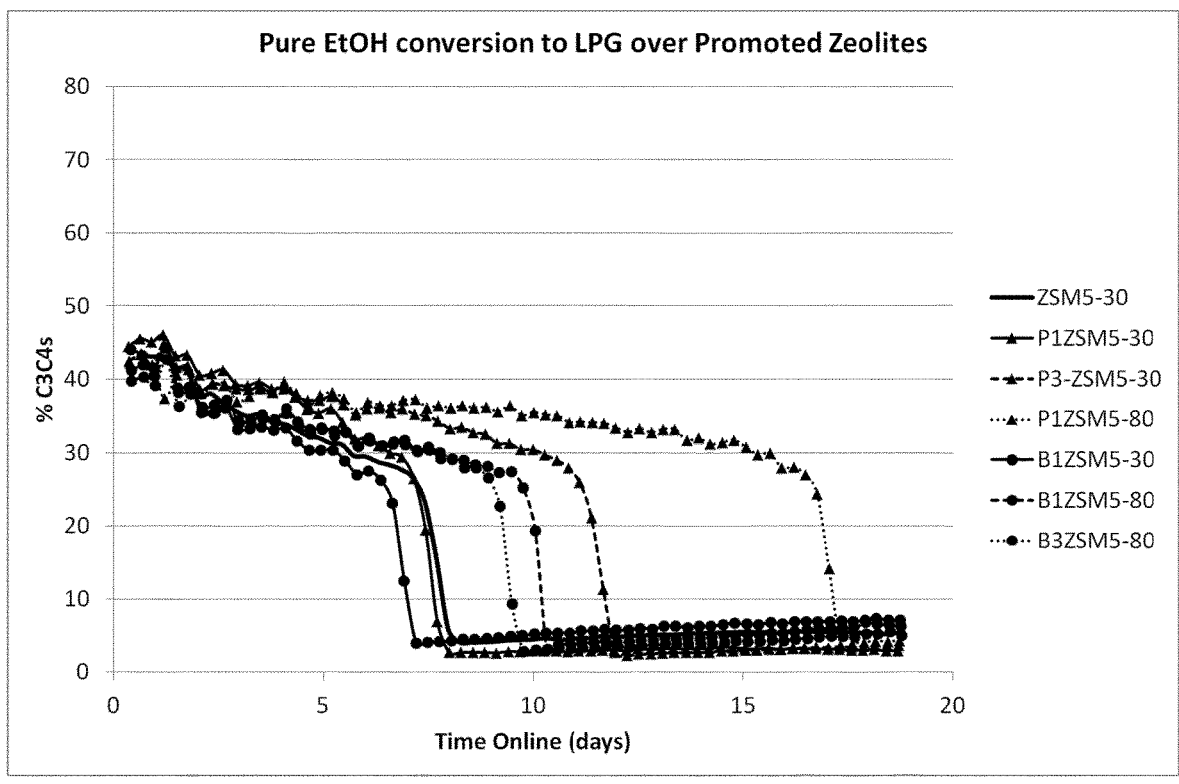
FIGS. 36 to 39 show the product selectivities of various processes of the invention with pure anhydrous ethanol feedstreams and feedstreams comprising mixtures of ethanol and water.
Figure 37:
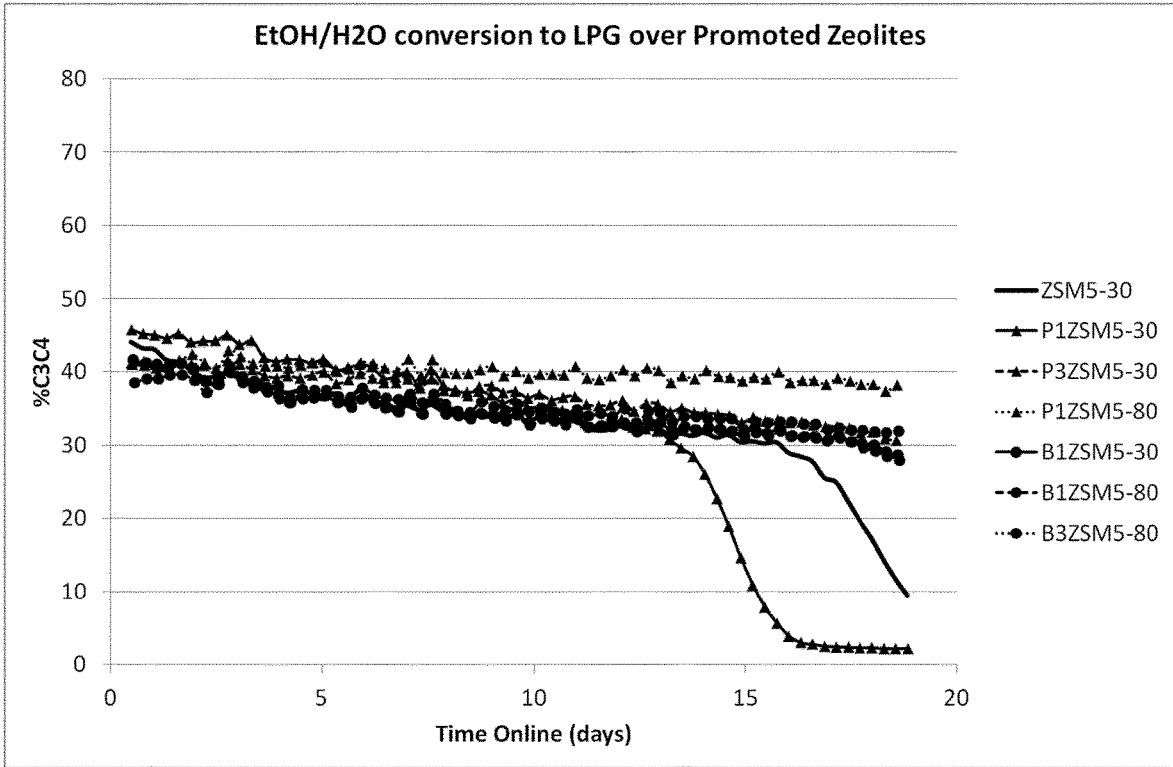
Figure 38:
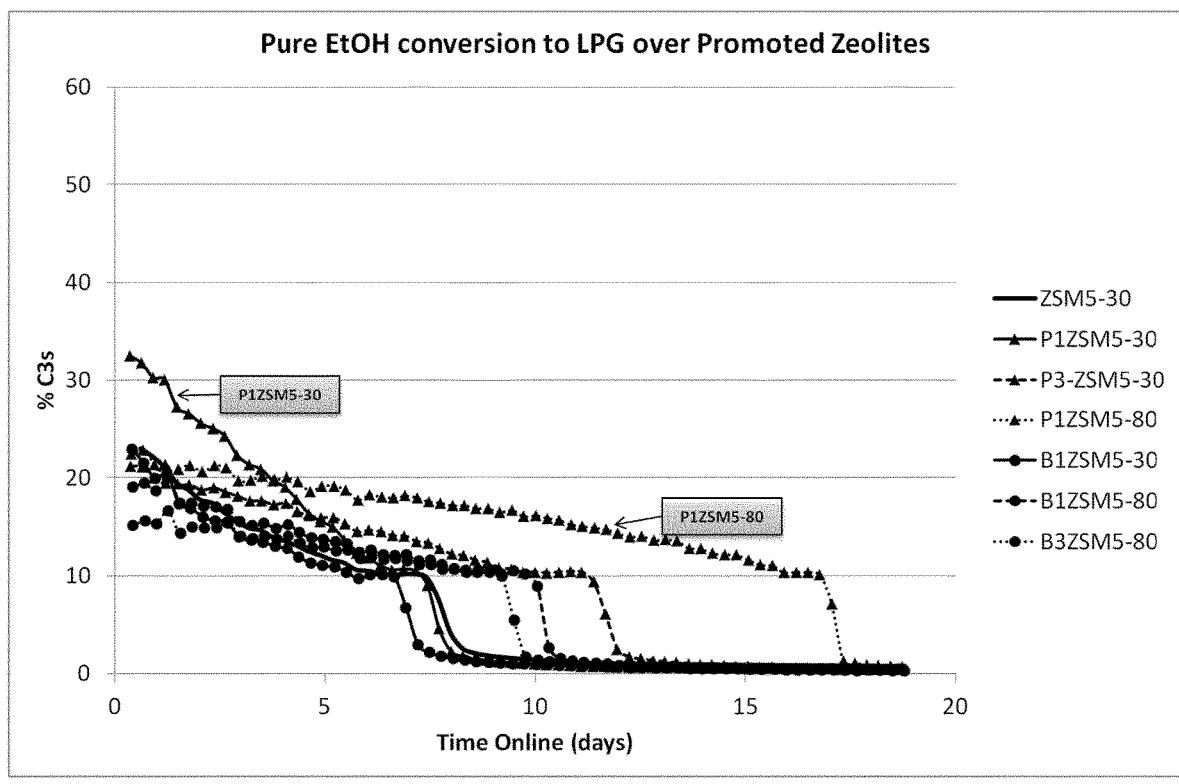
Figure 39:
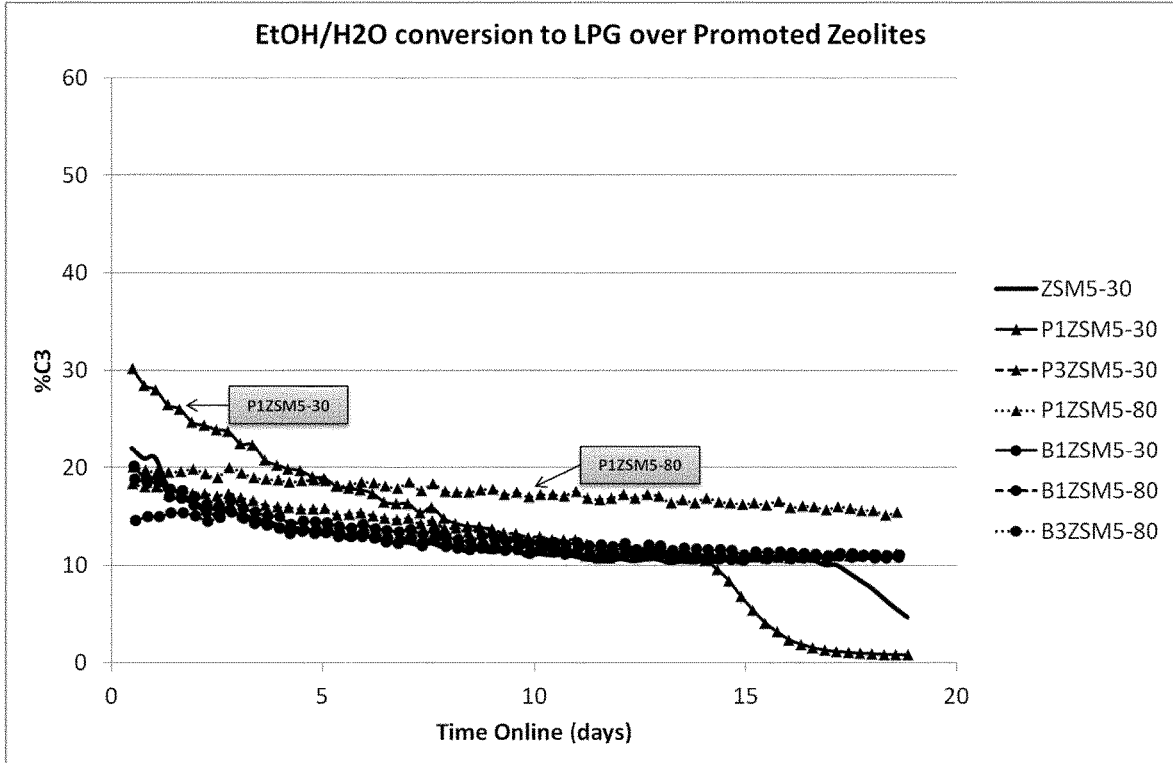
Figure 40:
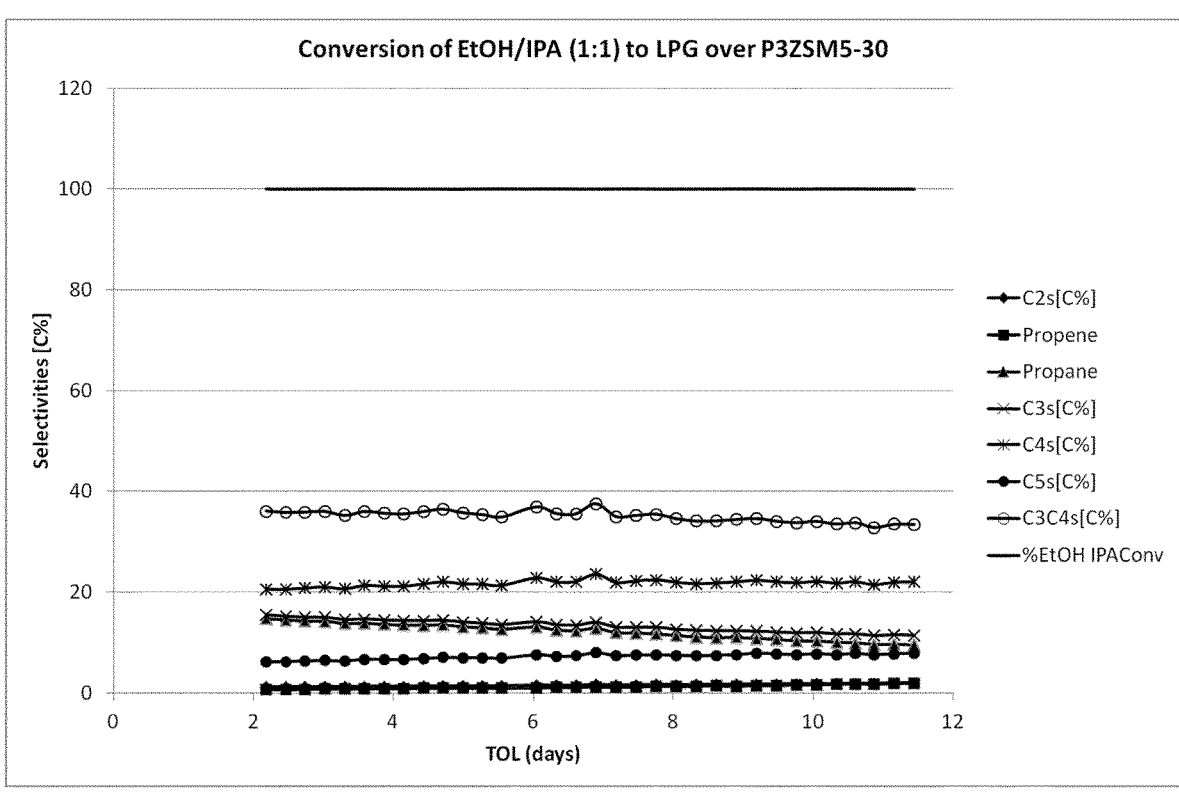
FIGS. 40 to 43 show the product selectivities of various processes of the invention with pure isopropanol feedstreams and feedstreams comprising isopropanol and ethanol mixtures.
Figure 41:
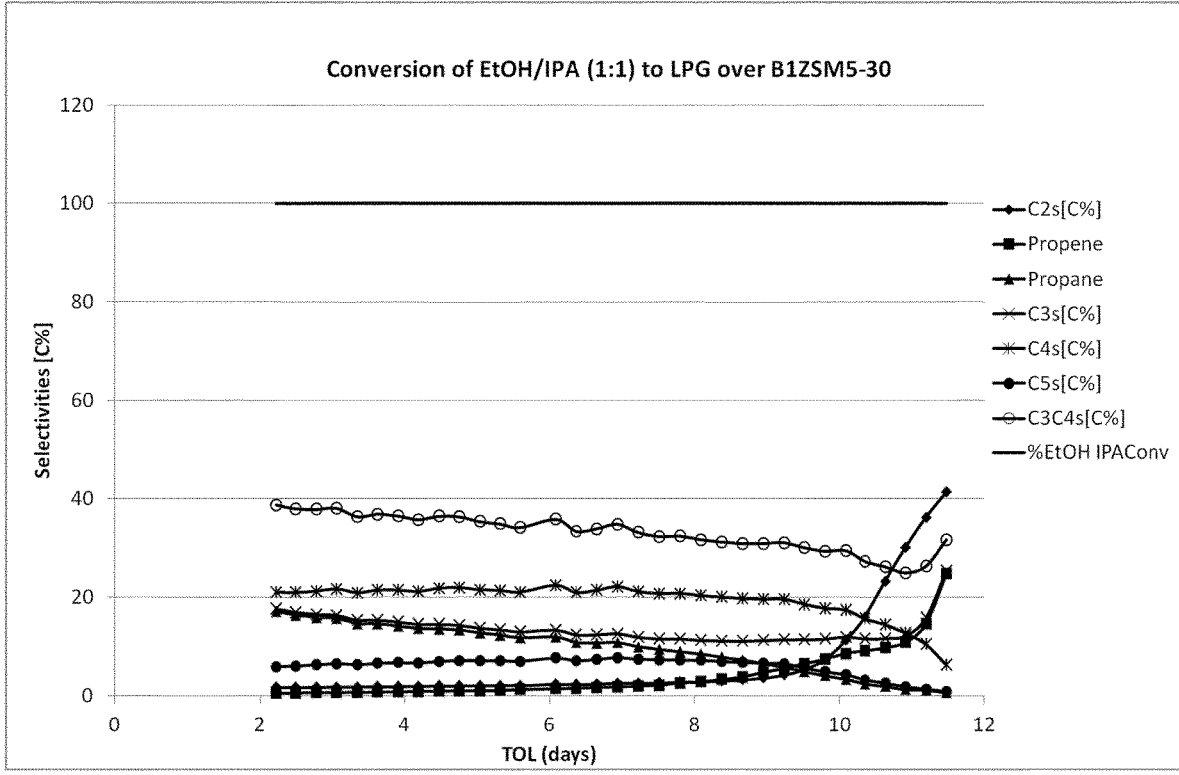

Further testing was performed upon the catalysts P1ZSM5-30, P1ZSM5-80 and B1ZSM5-80 synthesised in Example 5, and ZSM5-30, using the same reaction conditions as specified in Example 5. The results of these tests are shown in FIGS. 36 and 37.

It can be seen that both promoted ZSM5-80 catalysts had a similar initial C3/C4 and C3 selectivities to unpromoted ZSM5-30. However, P1ZSM5-30 had a higher initial C3/C4 and C3 selectivity than all other catalysts. However, the P1ZSM5-30 catalyst deactivated the fastest out of all of the catalysts.

Example 6

A further experiment was undertaken to investigate using the promoted zeolite catalyst in processes of the invention where the feedstream comprised both ethanol and water. The catalysts shown below in Table 7 were tested with both a pure anhydrous ethanol feedstream, and a feedstream comprising 85% ethanol and 15% water.

TABLE 7

| Catalyst | Mass of catalyst (mg) | Mass of SiC (mg) |
|---|---|---|
| P1/ZSM5-30 | 150 | 50 |
| P3/ZSM5-30 | 150 | 150 |
| P1/ZSM5-80 | 150 | 150 |
| B1/ZSM5-30 | 150 | 150 |
| B1/ZSM5-80 | 150 | 150 |
| B3/ZSM5-80 | 150 | 150 |

Reaction Conditions

Each catalyst was placed in a separate reaction vessel tube. After loading into the reaction vessel tubes, the tubes were heated under air flow to 475° C., and held for 3 hours. The tubes were cooled to 400° C. whilst purging with Argon and the reaction pressure set at 5 bar. Ethanol (or the ethanol/water mixture) was then introduced to each reaction vessel at a rate of 2.0 µL/min at a temperature of 400° C. Argon was introduced at a rate of 1 ml/min per reaction vessel tube as the internal standard and nitrogen was introduced to each catalyst bed in each reaction vessel tube at a rate of 37.5 ml/min as a diluent gas. The purpose of the nitrogen diluent gas is simply to increase the space velocity for subsequent gas chromatography analysis. These reaction conditions were maintained for the duration of the experiment.

The results of the experiments are shown in FIGS. 38 to 41. The figures show the C3/C4 selectivities and the C3 selectivities of each of the different catalysts tested when an anhydrous ethanol feedstream is used, and when a 85:15 mixture of ethanol and water is used.

In the pure anhydrous ethanol experiments, all promoted catalysts showed improved catalyst lifetime over the baseline unpromoted ZSM5-30 catalyst with the exception of B1/ZSM5-30 and P1/ZSM5-30. However, these catalysts showed improved initial selectivity when compared to the baseline unpromoted ZSM5-30 catalysts. P1ZSM5-80 afforded very good catalyst stability with deactivation onset only after 16 days. B1ZSM5-80, B3ZSM5-80 and P3-ZSM5-30 also all afforded considerably better lifetime than the baseline zeolite.

For the aqueous ethanol experiments, all promoted catalysts showed improved catalyst lifetime in comparison to the unpromoted baseline ZSM5-30 catalyst, with the exception of P1-ZSM5-30. However, this catalyst showed improved initial selectivity than the unpromoted baseline ZSM5-30 catalyst. All of the zeolite catalysts showed improved catalyst lifetime when using aqueous ethanol instead of pure anhydrous ethanol. The two outstanding zeolite catalysts were P1ZSM5-80 which showed remarkable catalyst stability and lifetime, and P1ZSM5-30 which showed excellent C3 selectivity.

Example 7

It was decided to investigate the catalytic activity of the catalyst using a different alcohol in the feedstream. Tests were undertaken on a pure iso-propanol (IPA) feedstream and a mixture of ethanol and iso-propanol. The same catalysts as listed above in Table 7 were tested under the same reaction conditions as specified in Example 6.

Results for a 1:1 Mixture of IPA and Ethanol

Figure 42:
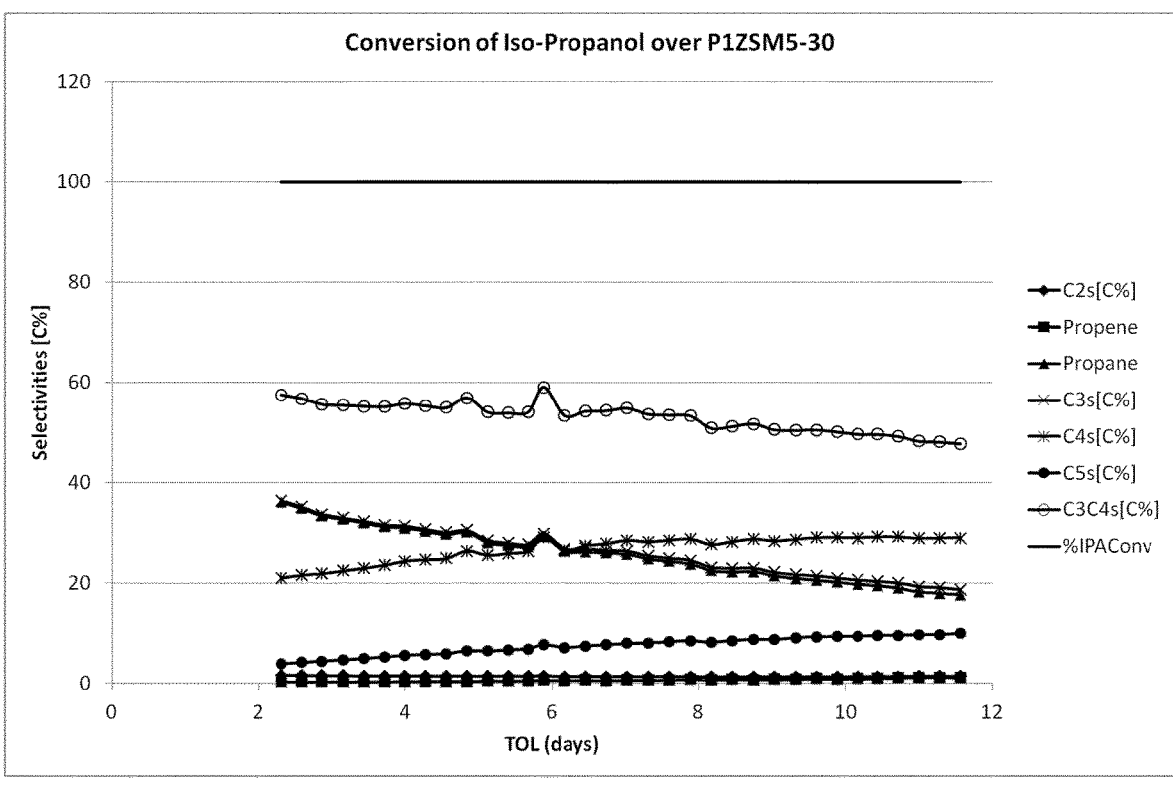
Figure 43:
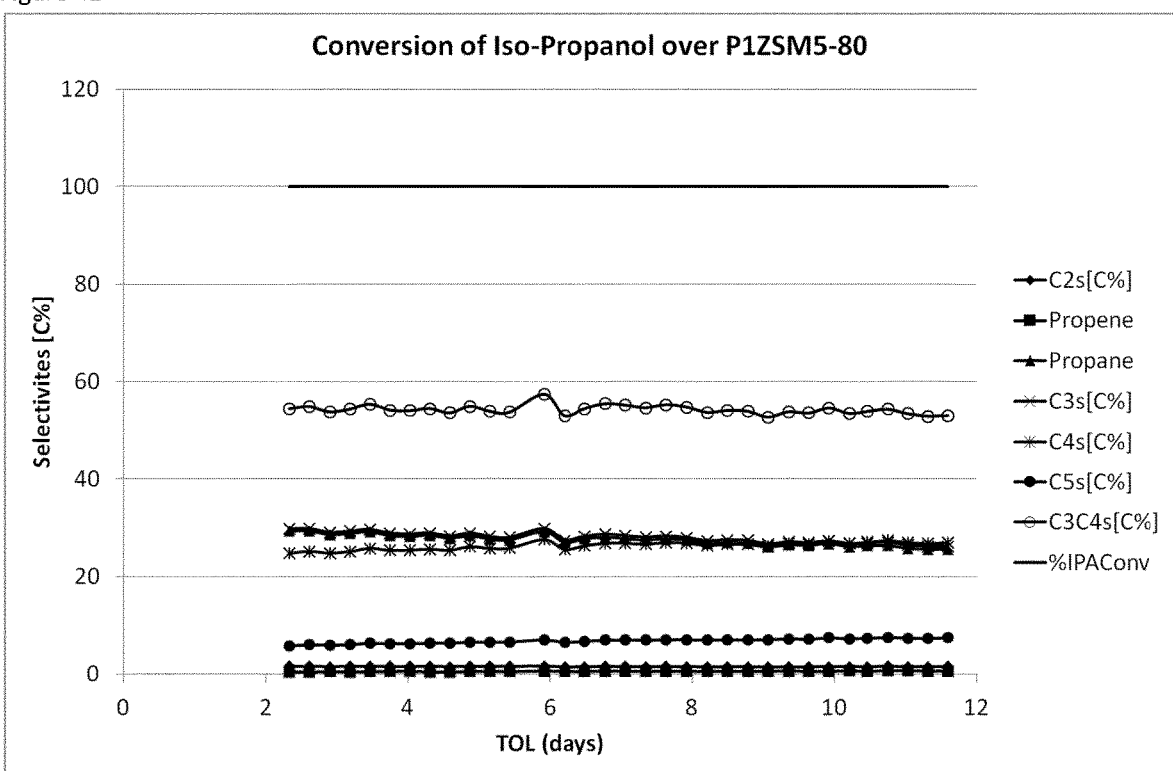

The results for P3ZSM5-30 and B1ZSM5-30 are shown in FIGS. 42 and 43 respectively. The results for the other zeolites (not shown) were broadly the same. It can be seen that both zeolites showed C3 and C4 hydrocarbon selectivity. The phosphorus promoted catalyst did not deactivate during the test period, whereas the boron promoted catalyst started to deactivate after around 10 days. Overall the use of ethanol/IPA for LPG formation showed results at least on par with when pure ethanol was used and therefore show that an IPA/ethanol mixture be a viable alternative bio-feedstock.

Results for Pure IPA

Figure 44:
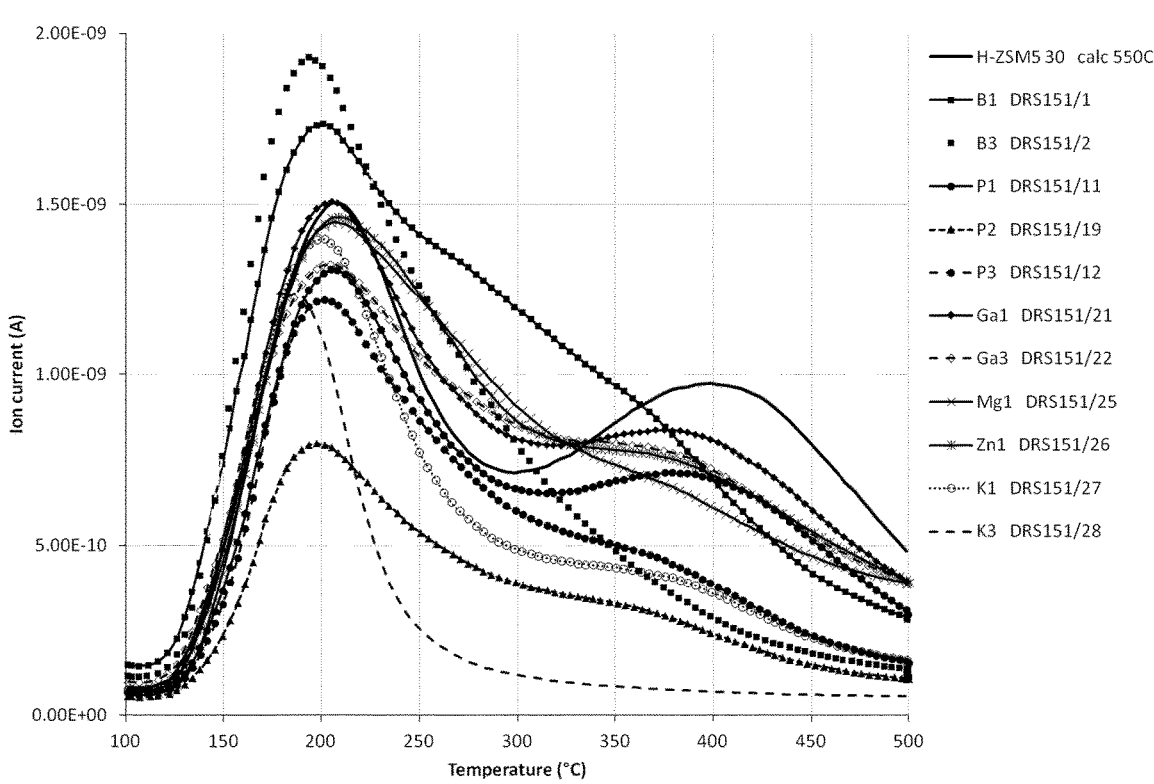
FIGS. 44 to 46 show the ammonia temperature programmed desorption (NH3 TPD) spectra of various zeolite catalysts.
Figure 45:
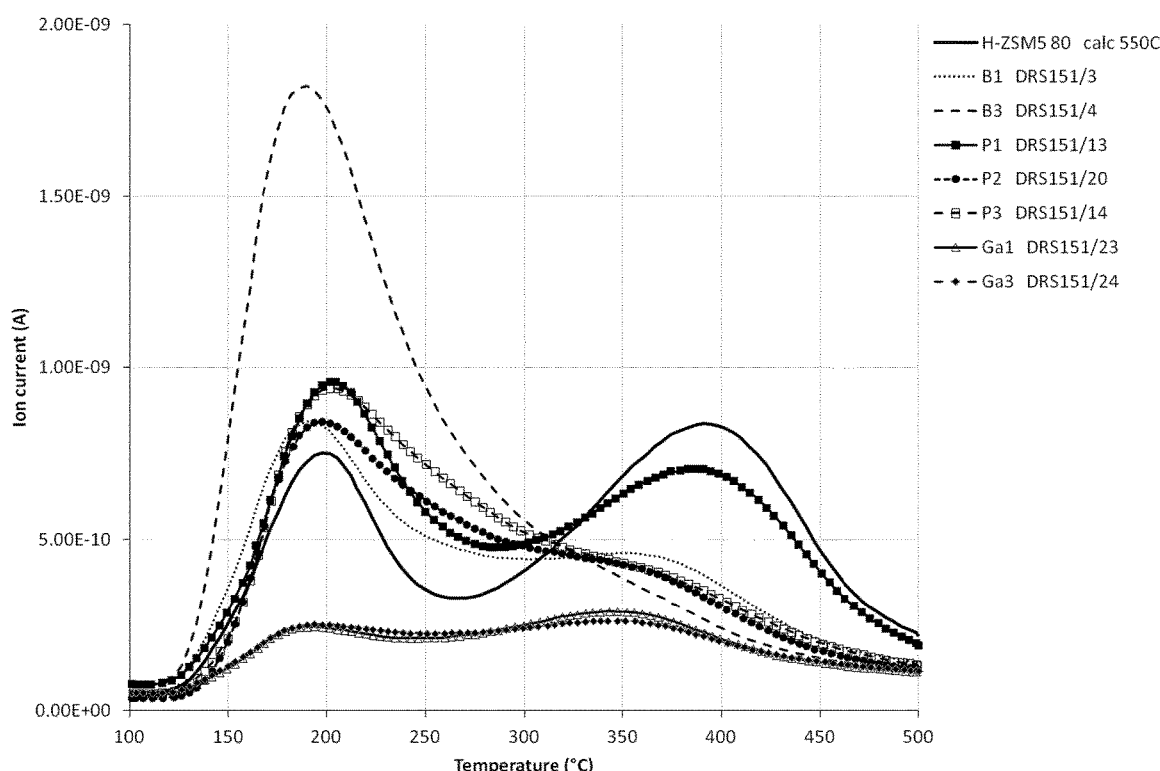

The results for P1ZSM5-30 and P1ZSM5-80 are shown in FIGS. 44 and 45 respectively. The results for the other zeolites (not shown) were broadly the same. The overall C3C4 selectivities (~50-57%) when using IPA was higher than the corresponding ethanol/IPA (~35-43%) and pure ethanol (35-43%) reactions. It is postulated that this may be due to the C3 feed being less likely to convert to heavier hydrocarbons and aromatics and hence a larger proportion of feed is converted to propane and iso-butane. None of the catalyst showed any signs of deactivation whatsoever over the twelve day testing period. The P1ZSM5-80 catalyst provided the best propane selectivity over the time online. In conclusion, the experiments have shown that pure IPA can be used as a conversion feedstock for LPG formation.

Example 8

Characterisation of various promoted zeolite catalyst materials was carried out using ammonia temperature programmed desorption ($NH_3$-TPD), using the following experimental protocol.

Experimental Protocol

Ammonia temperature programmed desorption (NH3-TPD) experiments were carried out in a Micromeritics 2920, which is equipped with a TCD detector and coupled to a Balzers Thermostar quadrupole mass spectrometer which allows the analysis and monitoring of gaseous products as a function of time or sample temperature. Around 80 mg of sample were loaded in the U-shaped tube and attached to the instrument. The sample was then dried under a flow of argon in a two steps process, at 120° C. for 30 min and 500° C. for 20 min. Then, the sample is cooled down to 100° C. and saturated with NH3 by flowing 5% NH3/He for 1 hour at this temperature, followed by an evacuation step of 1 hour. Then, the sample is heated up to 500° C. to desorb NH3, with both TCD and MS monitoring the effluent gas during the desorption step. The cation m/z 17 was detected to monitor $NH_3^+$ ions profiles.

Results

Figure 46:
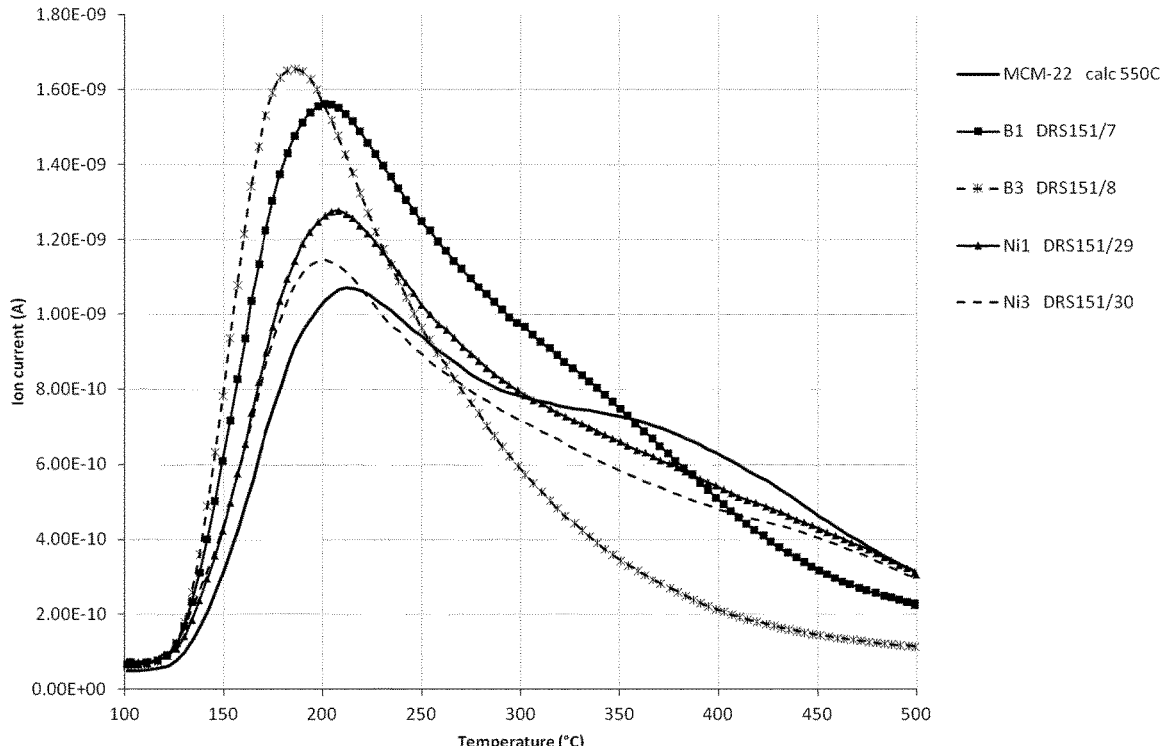

FIG. 46 shows the NH3-TPD profile of unpromoted zeolite H-ZSM5-30 contrasted with those of various promoted H-ZSM5-30 materials that were synthesised. FIG. 47 shows the NH3-TPD profile of unpromoted zeolite H-ZSM5-80 contrasted with those of various promoted H-ZSM5-80 materials that were synthesised.

It can be seen that the addition of promoter elements affects the TPD spectra of the zeolites. For the phosphorus and boron promoted zeolites, it can be seen that the lower temperature peak increases and the higher temperature peak decreases relative to the corresponding unpromoted zeolite material. This is indicative of a change in the acid site distribution of the catalyst. Specifically, this is indicative of an increase in the number of weak acid sites and a decrease in the number of strong acid sites, relative to the corresponding unpromoted zeolite material.

The data in table 8 below shows the total desorption for various promoted zeolites.

TABLE 8

| H-ZSM5 (30) series | Total Desorption m/z 17 Norm. Area (×10–10) | H-ZSM5 (80) series | Total Desorption m/z 17 Norm. Area (×10–10) |
|---|---|---|---|
| H-ZSM5-30 | 2.49 | H-ZSM5-80 | 1.39 |
| B1/ZSM5-30 | 2.74 | B1/ZSM5-80 | 1.32 |
| B3/ZSM5-30 | 2.32 | B3/ZSM5-80 | 1.70 |
| P1/ZSM5-30 | 1.93 | P1/ZSM5-80 | 1.24 |
| P2/ZSM5-30 | 0.96 | P2/ZSM5-80 | 0.99 |
| P3/ZSM5-30 | 1.25 | P3/ZSM5-80 | 1.16 |

The data in Table 8 shows that all boron and phosphorus promoted zeolites with the exception of B1/ZSM5-30 and B3ZSM5-80 had a lower acid site density than the corresponding baseline unpromoted zeolite material. This, combined with the altered acid site distribution discussed above, means that these promoted zeolites all had reduced total acidity compared to the corresponding unpromoted baseline zeolite material. The promoted zeolites B1/ZSM5-30 and B3ZSM5-80 had increased acid site density compared to the baseline unpromoted zeolite material. However, these zeolites still had a lower overall total acidity compared to the corresponding unpromoted baseline zeolite material due to the shifted acid site distribution discussed above where the promoted zeolites have more weak acid sites and less strong acid sites than the corresponding baseline unpromoted zeolite materials.

FIG. 48 shows the TPD spectrum for various promoted MCM22 zeolites compared to the baseline unpromoted MCM22 zeolite. It can be seen that all promoted zeolites had a shifted acid site distribution such that there more weak acid sites and less strong acid sites compared to the corresponding unpromoted baseline zeolite material. The total desorption (m/z 17 Norm. Area (×10-10)) for unpromoted MCM22 was 2.15, whereas for the B1 and B3 promoted materials it was 2.20 and 2.17 respectively. This is a incremental increase in the total number of acid sites. However, the significantly shifted acid site distribution in favour of weak acid sites means that the overall acidity of the boron promoted zeolites will be lower.

Example 9

Figure 49:
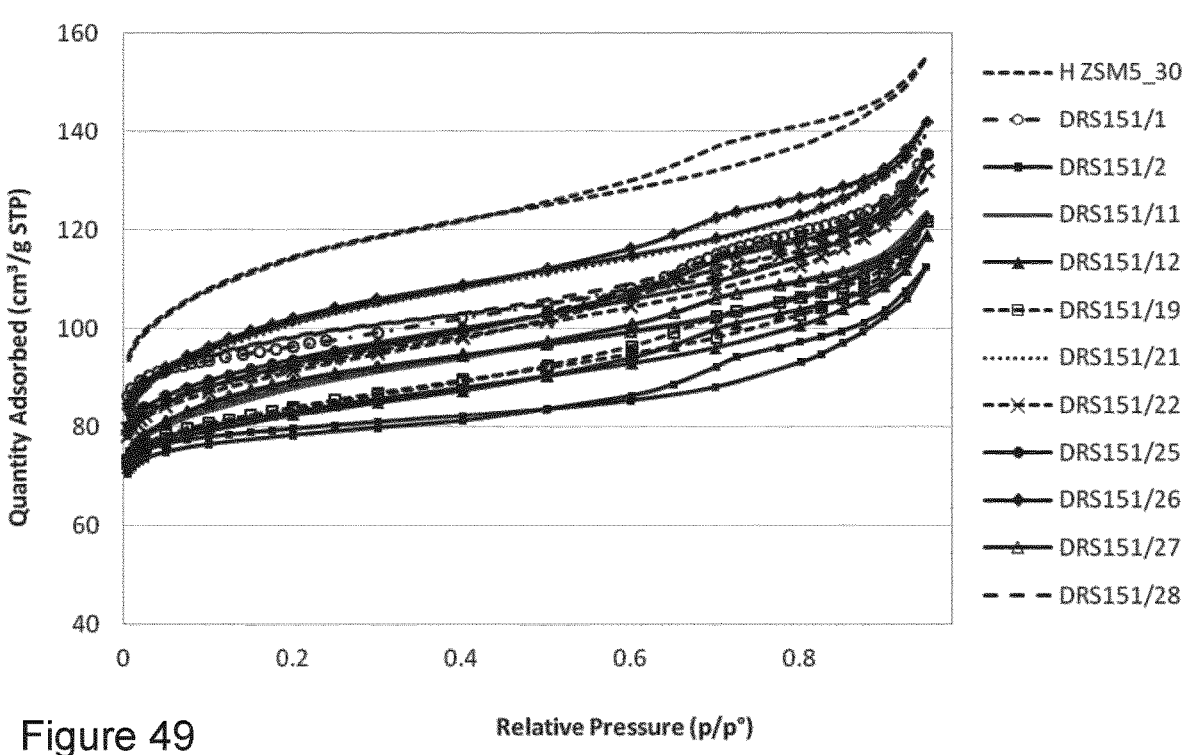
FIGS. 49 to 54 show the linear isotherm plots for various zeolite catalysts.
Figure 50:
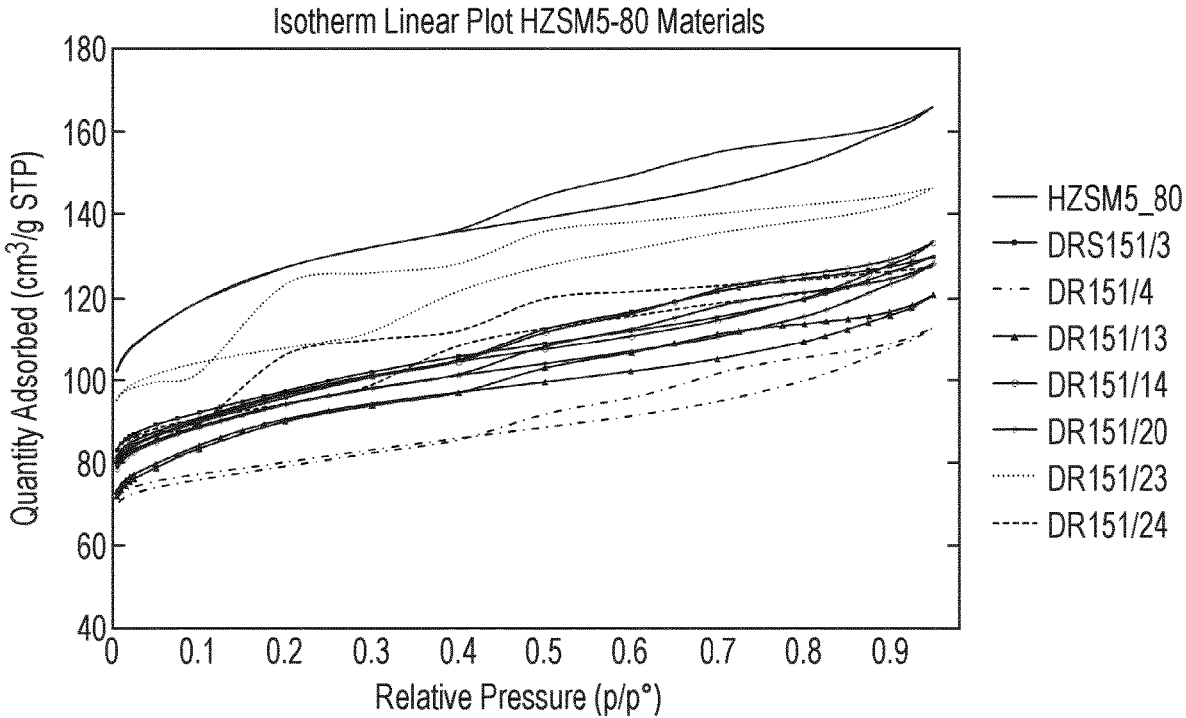
Figure 51:
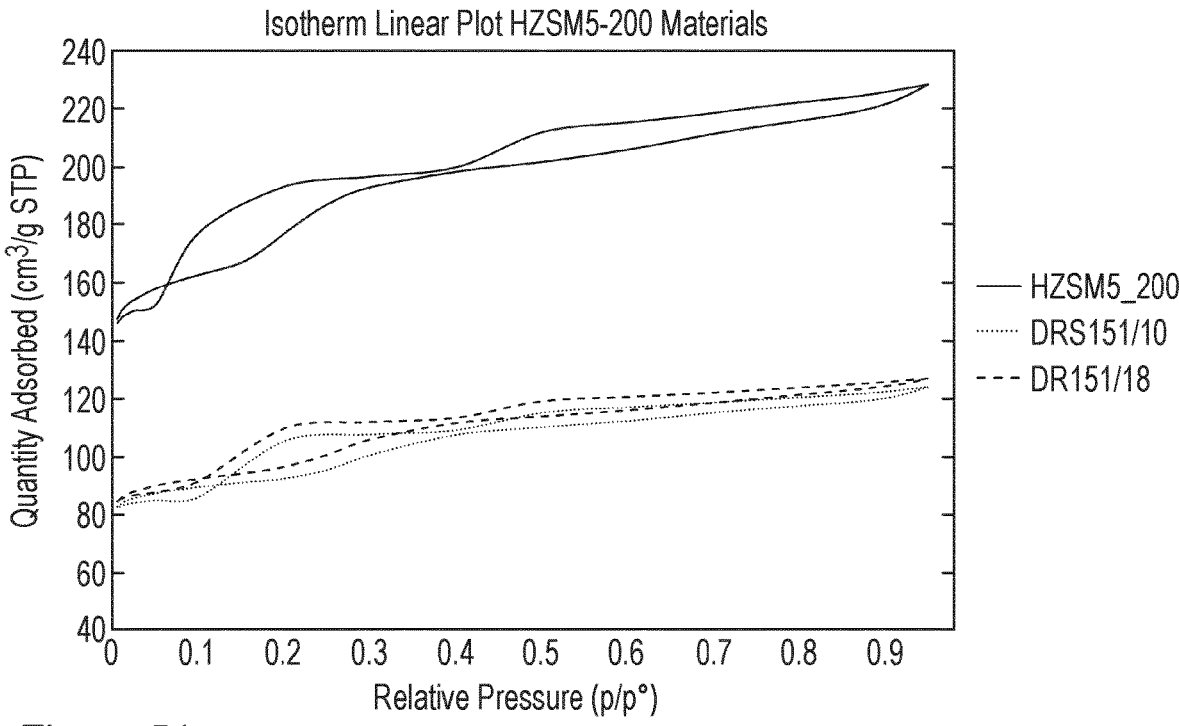
Figure 52:
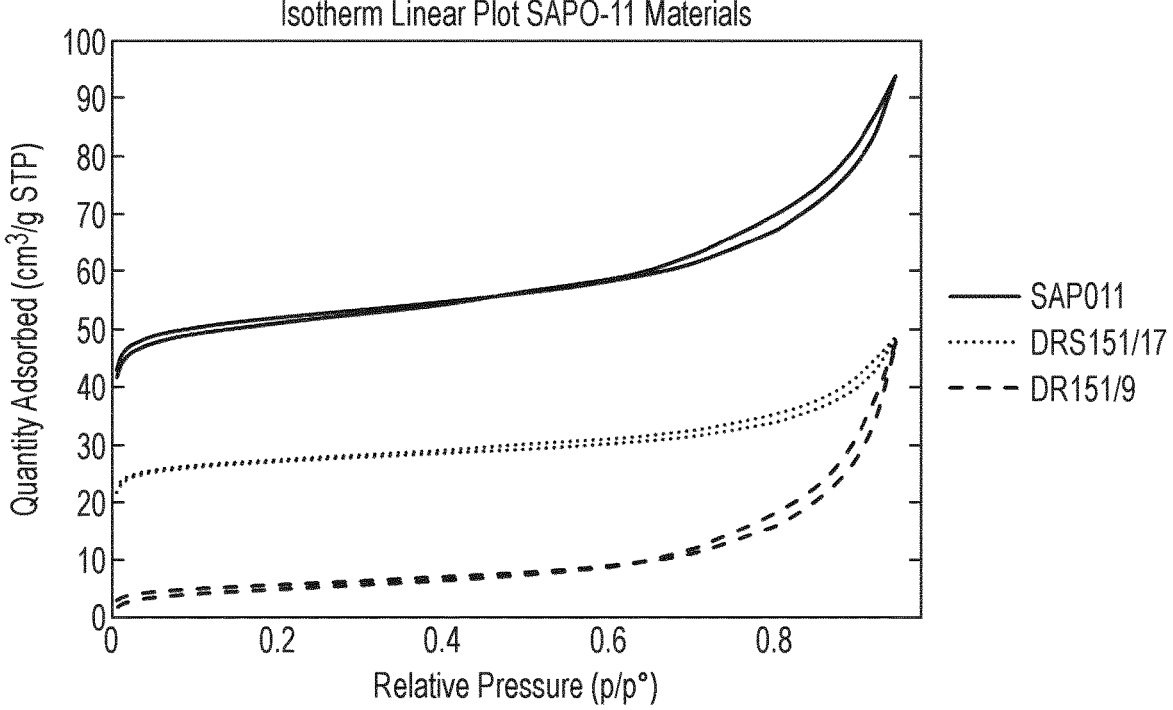
Figure 53:
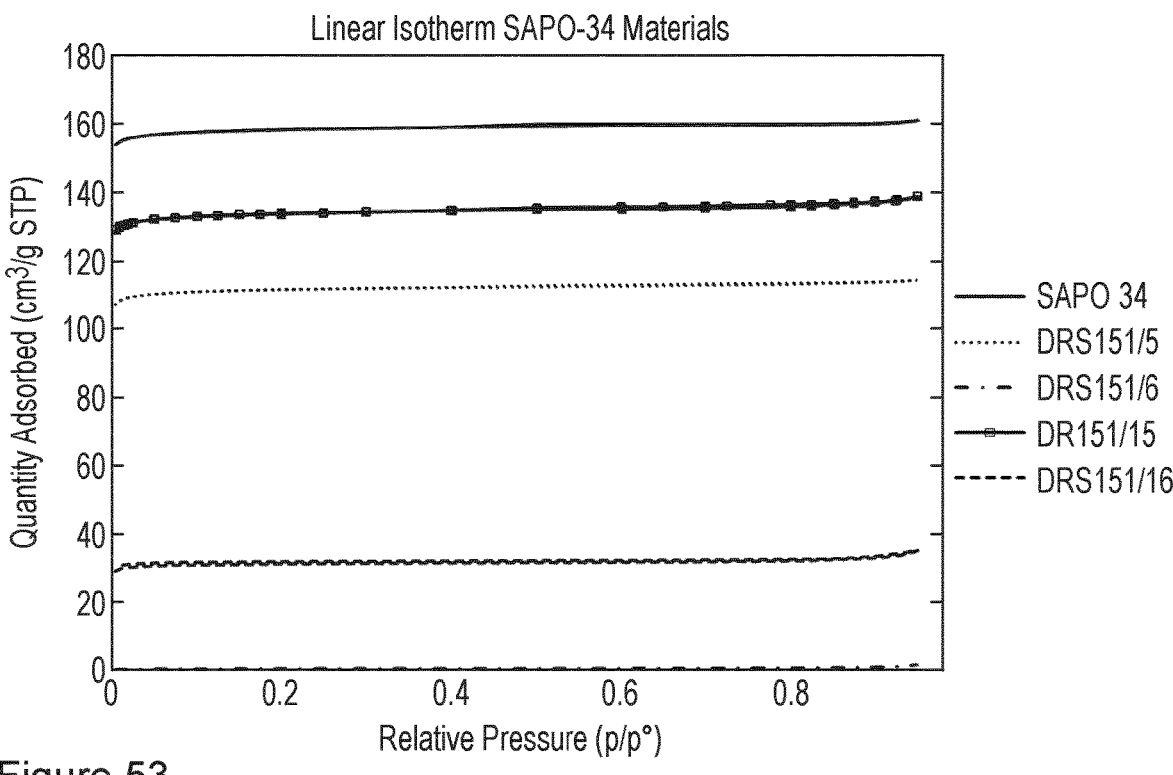
Figure 54:
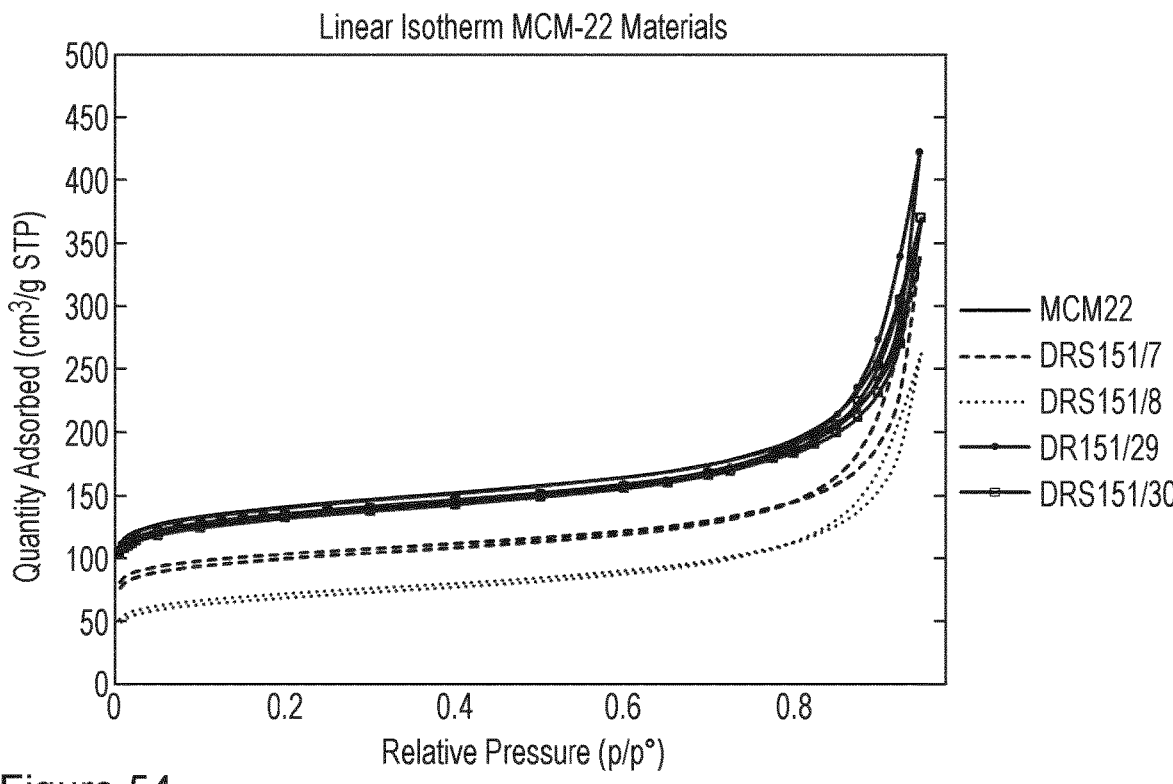

The porosity of a variety of unpromoted and promoted zeolite catalysts was investigated. All samples were measured with a Micromeritics Gemini VI instrument. The surface area was calculated using the Brunauer, Emmett and Teller (BET) transformation. The pore volume and area distribution were calculated using the Barret, Joyner and Helnda (BJH) method. The measurements are shown in the tables provided in FIGS. 49 and 50. All samples show a very similar isotherm typical of ZSM5 zeolites with a hysteresis loop confirming type-IV behaviour. FIGS. 51 to 56 show the linear isotherms of the zeolite materials.

Example 10

Further experiments were carried out to determine the performance of zeolite catalysts under different reaction conditions. The catalysts tested were ZSM5-80, P1ZSM5-30 and P1ZSM5-80.

The results of these experiments are shown in FIGS. 55 to 62.

Figure 55:
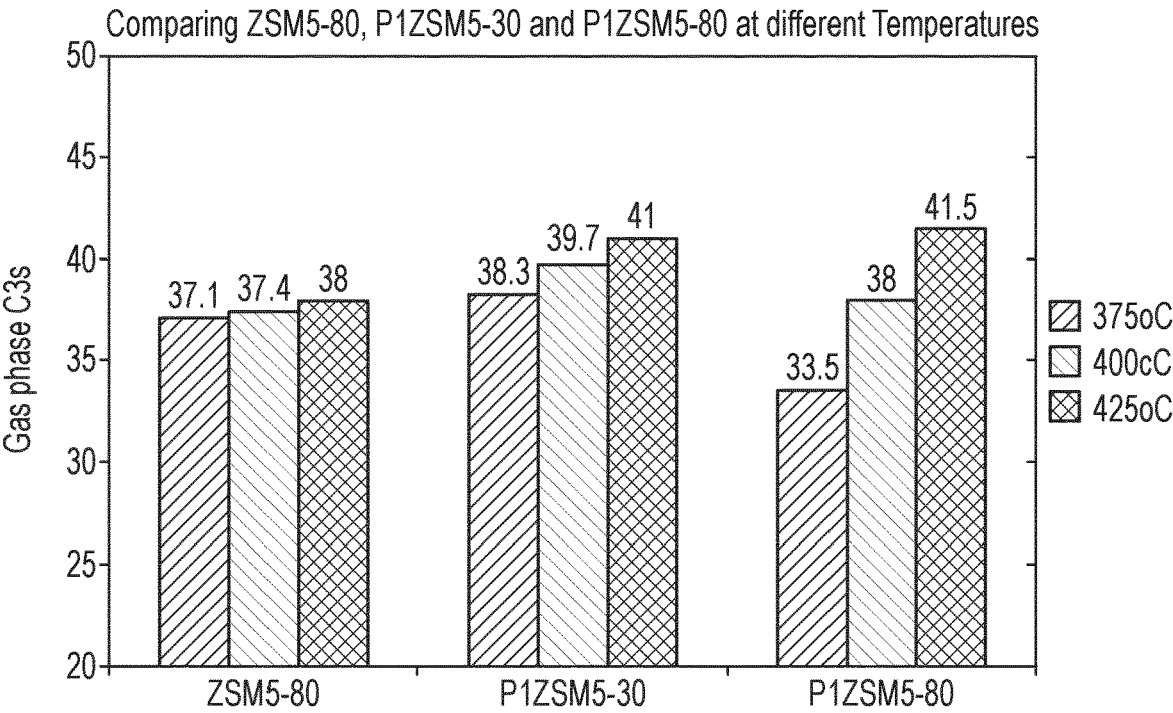
Figure 56:
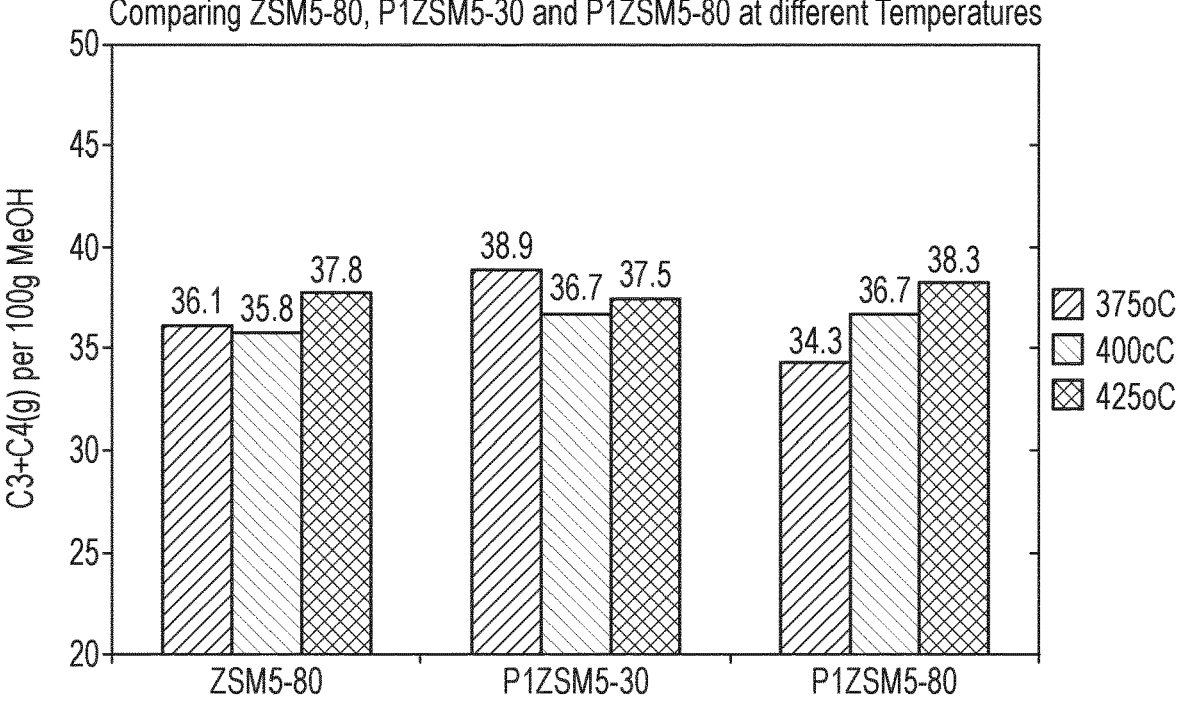

FIGS. 55 and 56 show the effect of different temperatures on the yield of C3 hydrocarbons and the sum of C3 and C4 hydrocarbons. Temperatures of 375° C., 400° C. and 425° C. are tested.

Figure 57:
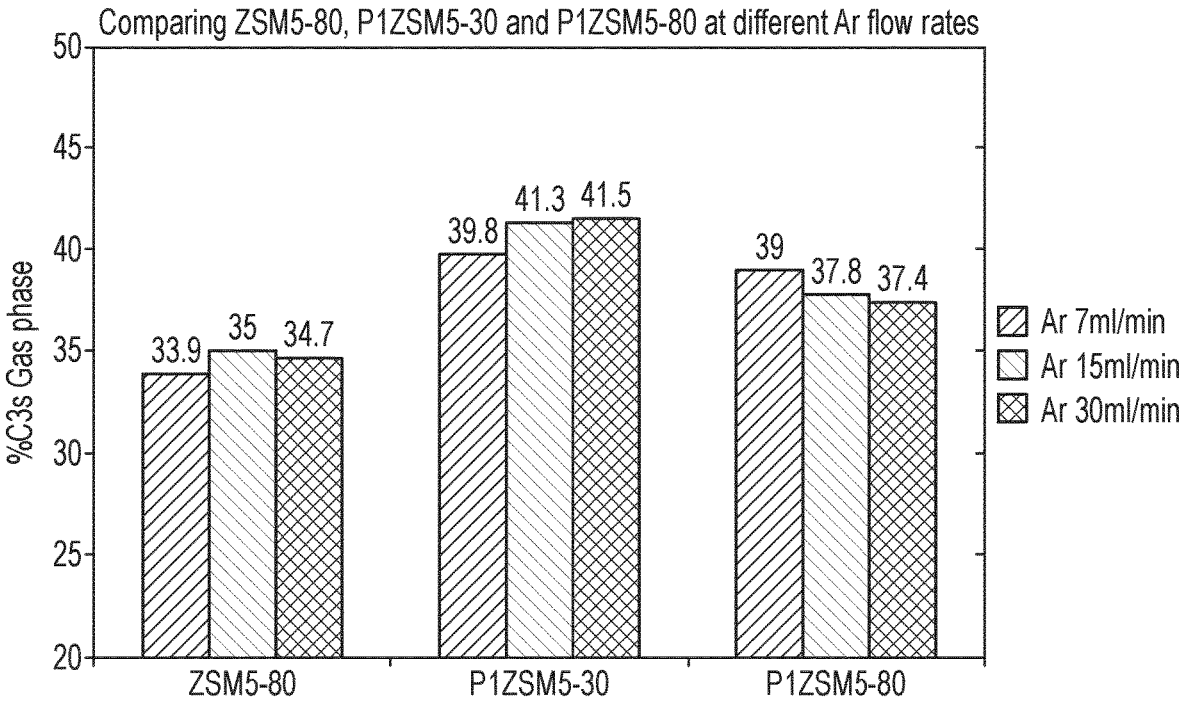
Figure 58:
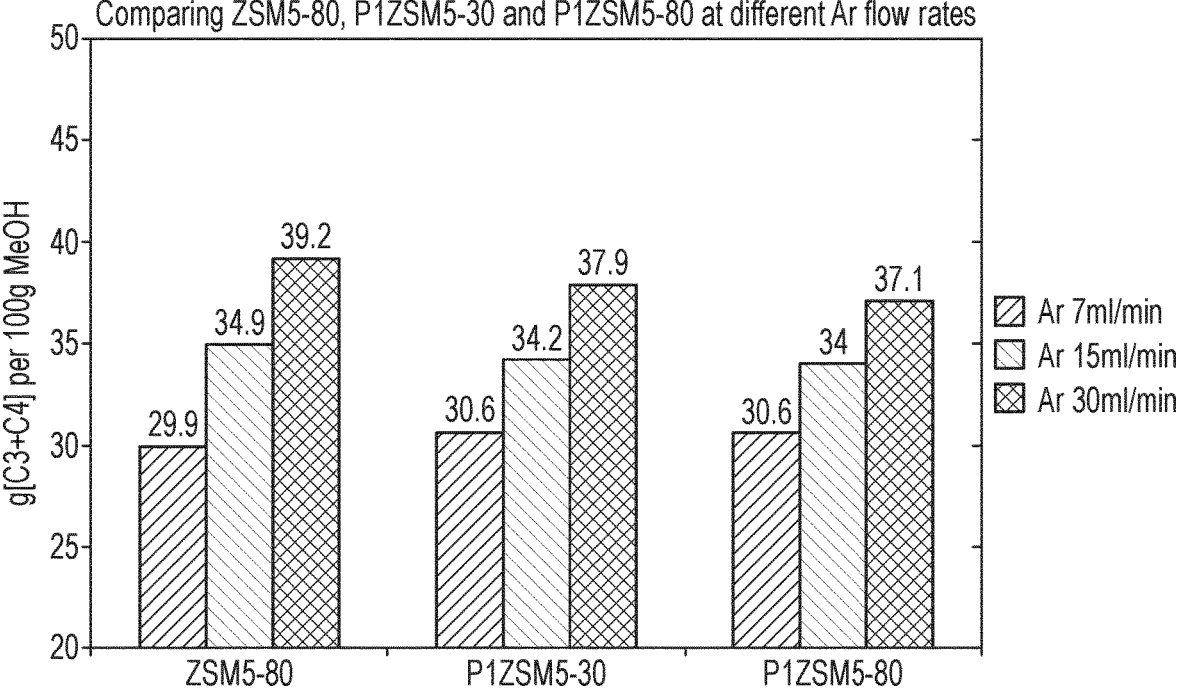

FIGS. 57 and 58 show the effect of different inert gas (argon) flow rates on the yield of C3 hydrocarbons and the sum of C3 and C4 hydrocarbons. Flow rates of 7 ml/minute/ gram of catalyst, 15 ml/minute per gram of catalyst and 30 ml/minute per gram of catalyst were tested. This corresponds to 1.05 ml/minute/150 mg of catalyst, 2.25 ml/min-ute/150 mg of catalyst and 4.5 ml/minute/150 mg of catalyst respectively.

FIGS. 59 and 60 show the effect of different alcohol flow rates on the yield of C3 hydrocarbons and the sum of C3 and C4 hydrocarbons. Flow rates of 10 µl/minute per gram of catalyst, 20 µl/minute per gram of catalyst, 40 µl/minute per gram of catalyst and 60 µl/minute per gram of catalyst were tested. This corresponds to 1.5 µl/min per 150 mg of catalyst, 3 µl/min per 150 mg of catalyst, 6 µl/min per 150 mg of catalyst and 9 µl/min per 150 mg of catalyst respectively.

Figure 61:
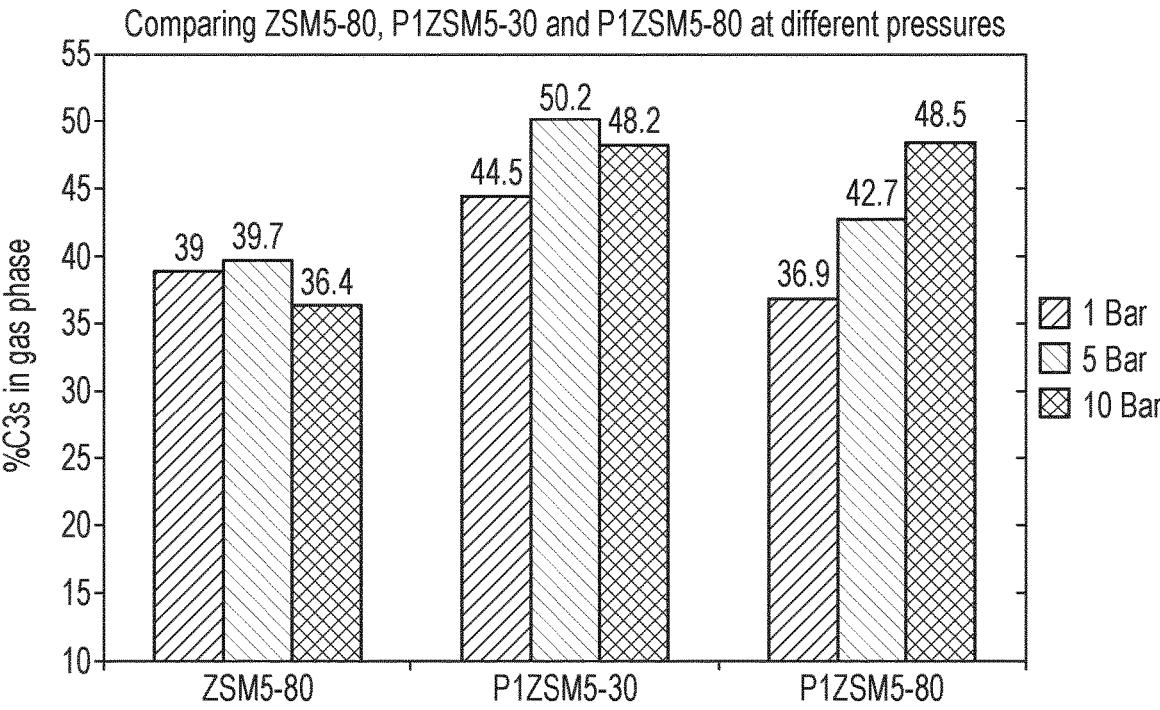
Figure 62:
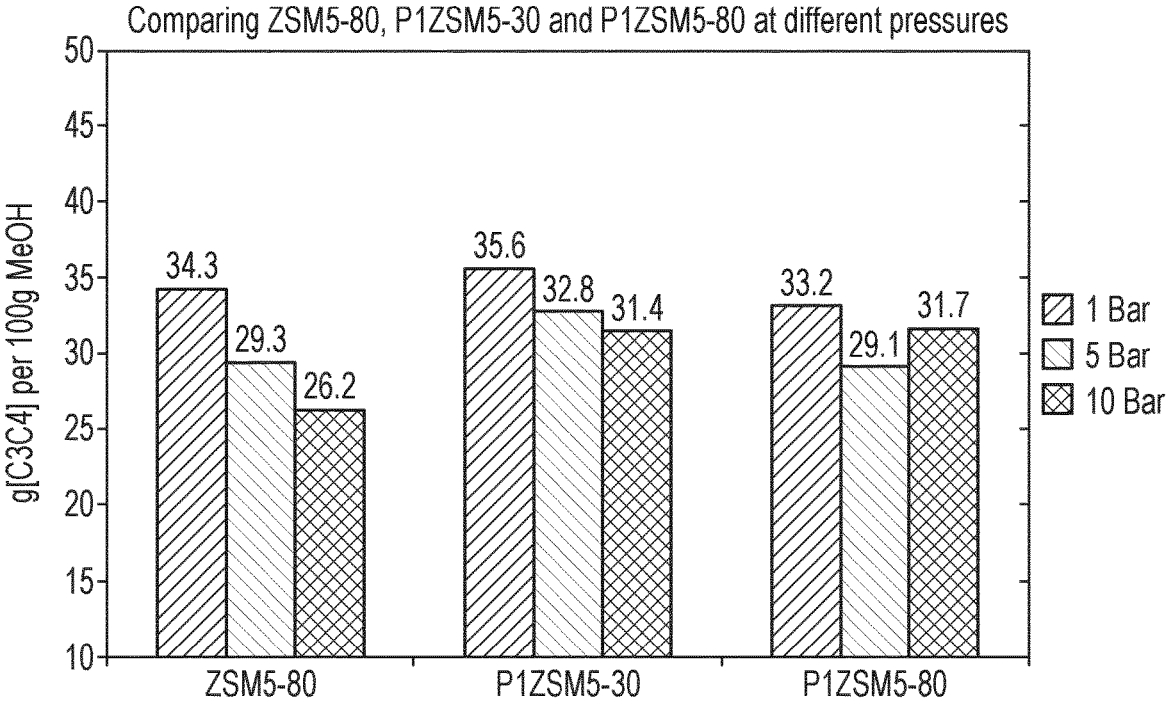

FIGS. 61 and 62 show the effect of different pressures on the yield of C3 hydrocarbons and the sum of C3 and C4 hydrocarbons. Pressures of 1 bar, 5 bar and 10 bar were tested.

The results of the experiments shown in FIGS. 55 to 62 demonstrate that the general trends in selectivities of the three tested catalysts at different operating conditions were similar. The following observations can be made:

Increased temperature produced higher overall yields for the sum of C3 and C4 hydrocarbons.

Higher inert gas flow rates over the catalyst bed also increased the yield of the sum of C3 and C4 hydrocarbons. The higher inert gas flow rates also caused lower amounts of aromatics to be produced as a by-product.

A lower ethanol flow rate increased the yield of both C3 hydrocarbons, and the sum of C3 and C4 hydrocarbons.

A higher reaction pressure desirably increased the amount of propane in the product stream. However, higher pressure also caused increased aromatics formation. As a result, the yield for the sum of C3 and C4 hydrocarbons was still highest at lower pressures.

The invention claimed is:

1. A process for the selective production of BioLPG from C2 or C3 aliphatic alcohols, wherein the process comprises:

(a) introducing a feedstream comprising one or more C2 or C3 aliphatic alcohols into a reaction vessel comprising a catalyst, wherein the catalyst comprises a ZSM5 zeolite material, an MCM22 zeolite material, or a combination thereof;

(b) contacting the feedstream and catalyst within the reaction vessel at a temperature of from 250° C. to 750° C. and a pressure of from 0.5 atm to 50 atm;

(c) recovering a product stream comprising C3 and/or C4 aliphatic hydrocarbons from the reaction vessel; and wherein the ZSM5 zeolite material or the MCM22 zeolite material are promoted zeolite materials that have reduced acidity as determined by temperature programmed desorption of ammonia, relative to the corresponding unpromoted zeolite material with equivalent Si/Al ratio, wherein the ZSM5 zeolite material or the MCM22 zeolite material have one or both of: i) a different acid site strength distribution as determined by temperature programmed desorption of ammonia, as the corresponding unpromoted zeo-lite material with equivalent Si/Al ratio; and ii) a different total number of acid sites as determined by temperature programmed desorption of ammonia, as the corresponding unpromoted zeolite material with equivalent Si/Al ratio.

2. A process according to claim 1, wherein (i) the con-tacting is carried out at a temperature of from 350° C. to 600° C., (ii) the contacting is carried out at a temperature of from 375° C. to 500° C.; (iii) the contacting is carried out at a pressure of from 1 atm to 20 atm; (iv) the contacting is carried out at a pressure of from 1 atm to 15 atm; (v) the contacting is carried out at a pressure of from 1 atm to 10 atm; (vi) the contacting is carried out at a pressure of from 3 atm to 50 atm; (vii) the contacting is carried out at a pressure of from 3 atm to 20 atm; (viii) the contacting is carried out at a pressure of from 3 atm to 15 atm; or (ix) the contacting is carried out at a pressure of from 3 atm to 10 atm.

3. A process according to claim 1, wherein process steps a) to c) are carried out continuously as a continuous flow process; wherein the continuous flow process comprises introducing the feedstream to the reactor vessel at a flow rate of from 1 µL to 10 µL per minute per 150 mg of catalyst present in the reactor vessel; at a flow rate of from 1 µL to 7.5 µL per minute per 150 mg of catalyst present in the reactor vessel; at a flow rate of from 1 µL to 5 µL per minute per 150 mg of catalyst present in the reactor vessel; at a flow rate of from 1 µL to 3 µL per minute per 150 mg of catalyst present in the reactor vessel; at a flow rate of from 1.5 µL to 2.5 µL per minute per 150 mg of catalyst present in the reactor vessel; or at a flow rate of from 1.75 µL to 2.25 µL per minute per 150 mg of catalyst present in the reactor vessel.

4. A process according to claim 3, wherein the process further comprises passing an inert gas through the reaction vessel during contacting step b), wherein the inert gas is introduced into the reaction vessel at a flow rate of from 0.5 ml/min to 10 ml/min per 150 mg of catalyst, from 0.5 ml/min to 5 ml/min per 150 mg of catalyst, from 1.5 ml/min to 5 ml/min per 150 mg of catalyst, or from 2 ml/min to 5 ml/min per 150 mg of catalyst.

5. A process according to claim 1, wherein contacting step b) further comprises contacting the catalyst with an inert diluent gas.

6. A process according to claim 1, wherein prior to step a), the catalyst is contacted with air or oxygen at a temperature of from 400° C. to 650° C. for a time period of from 1 hour to 10 hours; wherein prior to step a), but after the catalyst has been contacted with air or oxygen at a temperature of from 400° C. to 650° C. for a time period of from 1 hour to 10 hours, the reaction vessel is heated to a temperature of from 400° C. to 500° C. under air or oxygen flow for a time period of from 5 hours to 10 hours, before purging with an inert gas.

7. A process according to claim 1, wherein (i) the one or more C2 or C3 aliphatic alcohols comprise ethanol, isopro-pyl alcohol, or a combination thereof; or (ii) the one or more C2 or C3 aliphatic alcohols are derived from fermentation, derived from bio-generation, derived from fermentation of flue gases, or derived from fermentation of bio-generated syngas.

8. A process according to claim 1, wherein the feedstream comprising one or more C2 or C3 aliphatic alcohols com-prises the one or more C2 or C3 aliphatic alcohols in an amount of from 70% by weight to 100% by weight, or from 80% to 100% by weight of the total weight of components of the feedstream.

9. A process according to claim 7, wherein the feedstream comprising one or more C2 or C3 aliphatic alcohols further comprises water; wherein the feedstream comprising one or more C2 or C3 aliphatic alcohols further comprises water in an amount of from 1% by weight to 30% by weight of the total weight of components of the feedstream; or wherein the feedstream comprising one or more C2 or C3 aliphatic alcohols further comprises water in an amount of from 10% by weight to 20% by weight of the total weight of components of the feedstream.

10. A process according to claim 9, wherein the feedstream comprises ethanol in an amount of from 70% by weight to 99% by weight, or from 80% by weight to 90% by weight of the total weight of components of the feedstream.

11. A process according to claim 3, wherein the process has a selectivity for C3 and C4 aliphatic hydrocarbons after two days of at least 30%, when the flow rate of the feedstream is from 1.75 µL to 2.25 µL per minute per 150 mg of catalyst present in the reactor vessel.

12. A process according to claim 1, wherein the reaction vessel comprises a fixed bed reactor or a fluidised bed reactor; or wherein the catalyst further comprises a carrier, binder, or support material.

13. A process according to claim 1, wherein the catalyst comprises a ZSM5 zeolite material, wherein the ZSM5 zeolite material has a Si/Al ratio of from 20 to 150, from 25 to 100, from 25 to 90, or from 30 or 80.

14. A process according to claim 1, wherein the catalyst comprises MCM22 with a Si/Al ratio of from 10 to 70.

15. A process according to claim 1, wherein the promoted ZSM5 zeolite material or the promoted MCM22 zeolite material comprise one or more promoter elements selected from boron, phosphorus, gallium, magnesium, zinc, potassium and zirconium.

16. A process according to claim 15, wherein the one or more promoter elements are present in the promoted zeolite material in an amount of from 0.5 wt % to 5 wt %, or from 0.75 wt % to 3.25 wt %.

17. A process according to claim 1, wherein the catalyst comprises a ZSM5 zeolite material, wherein the promoted ZSM5 zeolite material is promoted with the elements boron or phosphorus.

18. A process according to claim 17, wherein (i) the boron or phosphorus are present in the ZSM5 material in an amount of from 0.75% to 3.25% by weight, (ii) the boron or phosphorus are present in the ZSM5 material in an amount of from 1% to 3% by weight; (iii) the ZSM5 zeolite material has a Si/Al ratio of from 25 to 90; (iv) the ZSM5 zeolite material has a Si/Al ratio of from 25 to 35; or (v) the ZSM5 zeolite material has a Si/Al ratio of from 75 to 85.

19. A process according to claim 18, wherein (i) the ZSM5 zeolite material has an Si/Al ratio of 75 to 85, and wherein the ZSM5-zeolite material comprises from 0.75% by weight phosphorus to 1.25% by weight phosphorus; (ii) wherein the ZSM-5 zeolite material has an Si/Al ratio of 80 and wherein the ZSM5-zeolite material comprises 1% by weight phosphorus; (iii) wherein the ZSM5 zeolite material has an Si/Al ratio of 25 to 30, and wherein the ZSM5-zeolite material comprises from 0.75% by weight phosphorus to 3.25% by weight phosphorus; (iv) wherein the ZSM-5 zeolite material has an Si/Al ratio of 30 and wherein the ZSM5-zeolite material comprises 1% by weight phosphorus, 2% by weight phosphorus, or 3% by weight phosphorus; (v) wherein the ZSM5 zeolite material has an Si/Al ratio of 75 to 85, and wherein the ZSM5-zeolite material comprises from 0.75% by weight boron to 3.25% by weight boron; (vi) wherein the ZSM-5 zeolite material has an Si/Al ratio of 80 and wherein the ZSM5-zeolite material comprises 1% by weight boron, 2% by weight boron, or 3% by weight boron; (vii) wherein the ZSM5 zeolite material has an Si/Al ratio of 25 to 35, and wherein the ZSM5-zeolite material comprises from 0.75% by weight boron to 3.25% by weight boron; or (viii) wherein the ZSM-5 zeolite material has an Si/Al ratio of 30 and wherein the ZSM5-zeolite material comprises 1% by weight boron, 2% by weight boron, or 3% by weight boron.

20. A process according to claim 3, wherein the process further comprises stopping the continuous process of steps a) to c); and contacting the catalyst with air or oxygen under conditions sufficient to rejuvenate the catalyst.

21. A process according to claim 3, wherein (i) the process further comprises stopping the continuous process of steps a) to c); and contacting the catalyst with air or oxygen at a temperature of from 300° C. to 600° C. for a time period of from 1 hour to 20 hours; (ii) wherein the process further comprises stopping the continuous process of steps a) to c) and contacting the catalyst with air or oxygen at a temperature of from 400° C. to 550° C. for a time period of from 5 hours to 15 hours; (iii) wherein the catalyst is rejuvenated such that the catalyst has an activity and selectivity equivalent to an initial activity and selectivity of the catalyst; (iv) wherein the catalyst is rejuvenated such that the catalyst has an activity and selectivity equivalent to 70% or more of an initial activity and selectivity of the catalyst; (v) wherein the catalyst is rejuvenated such that the catalyst has an activity and selectivity equivalent to 80% or more of an initial activity and selectivity of the catalyst; or (vi) wherein the catalyst is rejuvenated such that the catalyst has an activity and selectivity equivalent to 90% or more of an initial activity and selectivity of the catalyst.

22. A process for the selective production of BioLPG from C2 or C3 aliphatic alcohols, wherein the process comprises:

(a) introducing a feedstream comprising one or more C2 or C3 aliphatic alcohols into a reaction vessel comprising a catalyst, wherein the catalyst comprises a ZSM5 zeolite material, an MCM22 zeolite material, or a combination thereof;

(b) contacting the feedstream and catalyst within the reaction vessel at a temperature of from 250° C. to 750° C.; and (c) recovering a product stream comprising C3 and/or C4 aliphatic hydrocarbons from the reaction vessel;

wherein the process is a continuous flow process, and wherein the process comprises introducing the feedstream to the reactor vessel at a flow rate of from 1 µL to 10 µL per minute per 150 mg of catalyst present in the reactor vessel, and wherein the process further comprises passing an inert gas through the reaction vessel during contacting step b), wherein the inert gas is introduced into the reaction vessel at a flow rate of from 0.5 ml/min per 150 mg of catalyst to 10 ml/min per 150 mg of catalyst, from 0.5 ml/min per 150 mg of catalyst to 5 ml/min per 150 mg of catalyst, from 1.5 ml/min to 5 ml/min, per 150 ml of catalyst or from 2 ml/min to 5 ml/min per 150 mg of catalyst.

* * * * *